(12) United States Patent
Tuschl et al.

(10) Patent No.: US 7,772,389 B2
(45) Date of Patent: Aug. 10, 2010

(54) ANTI-MICRORNA OLIGONUCLEOTIDE MOLECULES

(75) Inventors: Thomas Tuschl, New York, NY (US); Markus Landthaler, New York, NY (US); Gunter Meister, New York, NY (US); Sebastien Pfeffer, Strasbourg (FR)

(73) Assignee: Rockefeller University, New York, NY (US)

( * ) Notice: Subject to any disclaimer, the term of this patent is extended or adjusted under 35 U.S.C. 154(b) by 592 days.

(21) Appl. No.: 10/589,449

(22) PCT Filed: Feb. 11, 2005

(86) PCT No.: PCT/US2005/004714

§ 371 (c)(1),
(2), (4) Date: Apr. 27, 2007

(87) PCT Pub. No.: WO2005/079397

PCT Pub. Date: Sep. 1, 2005

(65) Prior Publication Data

US 2007/0287179 A1 Dec. 13, 2007

(51) Int. Cl.
*C07H 21/04* (2006.01)
(52) U.S. Cl. .................. 536/24.5; 536/24.31; 536/24.1; 514/44
(58) Field of Classification Search ........................ None
See application file for complete search history.

(56) References Cited

U.S. PATENT DOCUMENTS

| | | | |
|---|---|---|---|
| 7,217,807 | B2 | 5/2007 | Bentwich |
| 7,365,058 | B2 | 4/2008 | Stoffel et al. |
| 2003/0108923 | A1 | 6/2003 | Tuschl et al. |
| 2005/0222067 | A1 | 10/2005 | Pfeffer et al. |
| 2006/0166910 | A1 | 7/2006 | Tuschl et al. |
| 2006/0257851 | A1 | 11/2006 | Bentwich |
| 2007/0039072 | A1 | 2/2007 | Khvorova et al. |
| 2007/0042381 | A1 | 2/2007 | Bentwich et al. |
| 2008/0114162 | A1 | 5/2008 | Khvorova et al. |
| 2008/0188428 | A1 | 8/2008 | Bentwich |
| 2008/0318210 | A1 | 12/2008 | Bentwich |

FOREIGN PATENT DOCUMENTS

| | | | |
|---|---|---|---|
| WO | WO03029459 | A2 | 4/2003 |
| WO | WO2004007718 | A2 | 1/2004 |
| WO | WO2004044123 | A2 | 5/2004 |
| WO | WO2004048511 | A2 | 6/2004 |
| WO | WO2005013901 | A2 | 2/2005 |
| WO | WO2005079397 | A2 | 9/2005 |
| WO | WO2006119266 | A2 | 11/2006 |

OTHER PUBLICATIONS

Hua et al. MIRNA directed regulation of VEGF and other angiogenic factors under hypoxia. PLoS One: Dec. 2006, Issue 1, e116 pp. 1-13.*

U.S. Appl. No. 10/604,945, filed Aug. 27, 2003.
U.S. Appl. No. 10/604,984, filed Aug. 29, 2003.
Avavin et al., "The Small RNA Profile During *Drosophila melanogaster* Development", Developmental Cell, vol. 5, p. 337-350 (2003).
Beigelman et al., "Chemical Modification of Hammerhead Ribozymes", The Journal of Biological Chemistry, vol. 270, No. 43, p. 25702-25708 (1995).
Liang et al., "Inhibitor RNA Blocks the Protein Translation Mediated by Hepatitis C Virus Internal Ribosome Entry Site in Vivo", World J. Gastroenterol, 10(5), p. 664-667 (2004).
Amarzguioui, Mohammed, et al., "Tolerance for mutations and chemical modifications in a siRNA", Nucleic Acids Research 2003, 31(2):589-595.
Bartel, David P., "MicroRNAs: Genomics, Biogenesis, Mechanism, and Function", Cell 2004, 116:281-297.
Elbashir, Sayda M., et al., "Duplexes of 21-nucleotide RNAs mediate RNA interference in cultured mammalian cells", Nature 2001, 411:494-498.
Holen, Torgeir, et al., "Positional effects of short interfering RNAs targeting the human coagulation trigger Tissue Factor", Nucleic Acids Research 2002, 30(8):1757-1766.
Holen, Torgeir, et al., "Similar behaviour of single-strand and double-strand siRNAs suggests they act through a common RNAi pathway", Nucleic Acids Research 2003, 31(9):2401-2407.
Howard, Ken, "Unlocking the money-making potential of RNAi", Nature Biotechnology 2003, 21(12):1441-1446.
Kurreck, Jens, "Antisense technologies Improvement through novel chemical modifications", Eur. J. Biochem. 2003, 270:1628-1644.
Meister, Gunter, et al., "Sequence-specific inhibition of microRNA- and siRNA-induced RNA silencing", RNA 2004, 10:544-550.
Nelson, Peter, et al., "The microRNA world: small is mighty", TRENDS in Biochemical Sciences 2003, 28(10):534-540.
Database EMBL (Online), "*Homo sapiens* Genomic Sequence Surrounding NotI site, clone NR3-B07C", XP002451881 retrieved from EBI accession No. EMBL: AJ332626: 21/22 residues match SEQ ID No. 1; Oct. 2001, abstract.
Database EMBL (Online), 'NISC_js08a05.w1 Soares NMBP1 *Mus musculus* cDNA clone Image: 4314537 5', mRNA sequence, XP002451882 retrieved from EBI accession No. EMBL: CB057718; 22/22 residues match SEQ ID No. 3; Jan. 2003, abstract.
Database EMBL (Online), CH4#001_G02T7 Canine Heart Normalized CDNA Library in pBluescript *Canis familaris* CDNA clone CH4#001_G02 5', mRNA sequence. XP002451883 retrieved from EBI accession No. EMBL: BU751380: 22/22 residues match SEQ ID No. 4; Oct. 2002, abstract.

(Continued)

*Primary Examiner* — Kimberly Chong
(74) *Attorney, Agent, or Firm* — Hoffmann & Baron, LLP

(57) ABSTRACT

The invention relates to isolated anti-microRNA molecules. In another embodiment, the invention relates to an isolated microRNA molecule. In yet another embodiment, the invention provides a method for inhibiting microRNP activity in a cell.

19 Claims, 3 Drawing Sheets

OTHER PUBLICATIONS

Berezikov et al., "Phylogenetic Shadowing and Computational Identification of Human MicroRNA Genes", Cell, vol. 120, pp. 21-24 (2005).

Seitz, et al., "A Large Imprinted MicroRNA Gene Cluster at the Mouse ElkI-Gtl2 Domain", Genome Research, pp2. 1-8 (2004).

Xie et al., "Systematic Discovery of Regulatory Motifs in Human Promoters and 3' UTR's by Comparison of Several Mammals", Nature, pp. 1-8 (2005).

Analysis and accompanying remarks by Rosetta Genomics of the sequences presented in Table A2 of the specification of the instant application (Jun. 28, 2007).

Table of information provided by Rosetta regarding the applications submitted in IDS dated Jul. 12, 2007 (Jun. 28, 2007).

Analysis by Rosetta of the sequences of Table A2 compared to those disclosed in Rosetta's patent applications (Jun. 28, 2007).

AC146999, Murphy et al. Oct. 31, 2003, p. 1-67.

Murphy et al., "Coding Potential of Laboratory and Clinical Strains of Human Cytomegalovirus", PNAS, vol. 100, No. 25, p. 14976-14981 (2003).

Taliansky et al., "An Umbraviral Protein, Involved in Long-Distance RNA Movement, Binds Viral RNA and Forms Unique, Protective Ribonucleoprotin Complexes", Journal of Virology, vol. 77, No. 5, p. 3031-3040 (2003).

Paddison et al., "Short Hairpin RNAs (shRNAs) Induce Sequence-Specific Silencing in Mammalian Cells", Genes & Development, 16:948-958 (2002).

Wiebusch et al., "Inhibition of Human Cytomegalovirus Replication by Small Interfering RNAs", Journal of General Virology, 85, p. 179-184 (2004).

Vanitharani et al., "Short Interfering RNA-Mediated Interference of Gene Expression and Viral DNA Accumulation in Cultured Plant Cells", PNAS, vol. 100, No. 16, p. 9632-9636 (2003).

Pfitzner et al., "Isolation and Characterization of cDNA Clones Corresponding to Transcripts from the BamHI H and F Regions of the Epstein-Barr Virus Genome", Journal of Virology, vol. 61, No. 9, p. 2902-2909 (1987).

Pfeffer et al., "Indentification of Virus-Encoded microRNAs", Science, vol. 304, p. 734-736 (2004).

Pfeffer et al., "Identification of microRNAs of the Herpesvirus Family", Nature Methods, Published Online DOI:10.1038/NMETH746, p. 1-8, Apr. 2004.

Zeng, et al., "MicroRNAs and Small Interfering RNAs Can Inhibit mRNA Expression by Similar Mechanisms", PNAS, vol. 100, No. 17, p. 9779-9784 (2003).

Boutla et al., "Developmental Defects by Antisense-Mediated Inactivation of Micr-RNAs 2 and 13 in *Drosophila* and the Identification of Putative Target Genes", Nucleic Acids Research, vol. 31, No. 17, pp. 4973-4980 (2003).

Kawasaki et al., "Hes1 is a Target of MicroRNA-23 During Retinoic-Acid-Induced Neutonal Differentiation of NT2 Cells", Nature, vol. 423, No. 6942, pp. 838-842 (2003).

Mourelatos et al., "MiRNPs: A Novel Class of Ribonucleoproteins Containing Numerous microRNAs", Genes and Development, vol. 16, No. 6, pp. 720-728 (2002).

Hutvagner et al., "Sequence-Specific Inhibition of Small HRN function", PLOS Biology, Public Library of Science, vol. 2, No. 4, pp. 465-475 (2004).

* cited by examiner

Figure 1

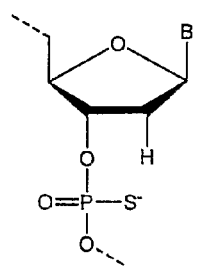

Phosphorothioate DNA Unit
(PS)
Structure 1

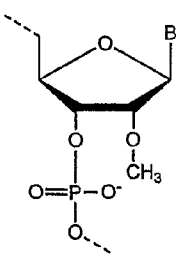

2'-O-methyl RNA unit
(OMe)
Structure 3

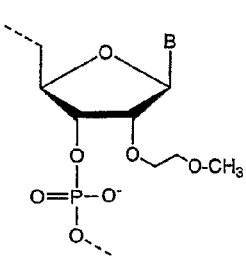

2'-O-methoxy-ethyl RNA unit
(MOE)
Structure 4

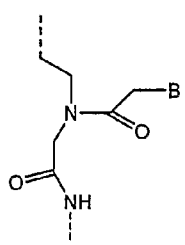

Peptide nucleic acid unit
(PNA)
Structure 6

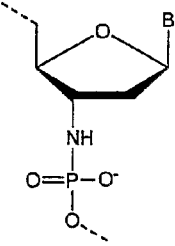

N3'-P5' Phosphoroamidate DNA unit
(NP)
Structure 2

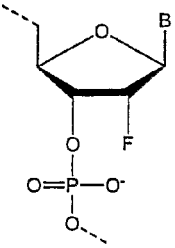

2'-fluoro-ribo nucleic acid unit
(FANA)
Structure 7

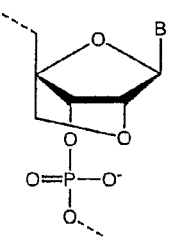

Locked nucleic acid unit
(LNA)
Structure 5

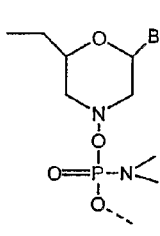

Morpholino phosphoroamidate
nucleic acid unit
(MF)
Structure 8

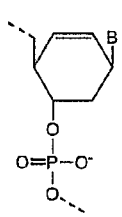

Cyclohexane nucleic acid unit
(CeNA)
Structure 10

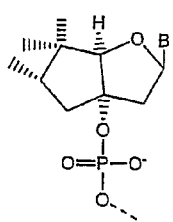

Tricyclonucleic acid unit
Structure 9

SEQUENCE LISTING

<160> NUMBER OF SEQ ID NOS: 623

<210> SEQ ID NO 1
<211> LENGTH: 22
<212> TYPE: RNA
<213> ORGANISM: Homo sapiens

<400> SEQUENCE: 1
aacccguaga uccgaacuug ug                                          22

```
<210> SEQ ID NO 2
<211> LENGTH: 22
<212> TYPE: RNA
<213> ORGANISM: Homo sapiens

<400> SEQUENCE: 2
agcagcauug uacagggcua ug                                                  22

<210> SEQ ID NO 3
<211> LENGTH: 22
<212> TYPE: RNA
<213> ORGANISM: Homo sapiens

<400> SEQUENCE: 3
ucaaaugcuc agacuccugu gg                                                  22

<210> SEQ ID NO 4
<211> LENGTH: 22
<212> TYPE: RNA
<213> ORGANISM: Homo sapiens

<400> SEQUENCE: 4
aaaagugcuu acagugcagg ua                                                  22

<210> SEQ ID NO 5
<211> LENGTH: 22
<212> TYPE: RNA
<213> ORGANISM: Homo sapiens

<400> SEQUENCE: 5
uaaagugcug acagugcaga ua                                                  22

<210> SEQ ID NO 6
<211> LENGTH: 22
<212> TYPE: RNA
<213> ORGANISM: Homo sapiens

<400> SEQUENCE: 6
agcagcauug uacagggcua uc                                                  22

<210> SEQ ID NO 7
<211> LENGTH: 22
<212> TYPE: RNA
<213> ORGANISM: Homo sapiens

<400> SEQUENCE: 7
uacccuguag aaccgaauuu gu                                                  22

<210> SEQ ID NO 8
<211> LENGTH: 22
<212> TYPE: RNA
<213> ORGANISM: Homo sapiens

<400> SEQUENCE: 8
ucacagugaa ccggucucuu uc                                                  22

<210> SEQ ID NO 9
<211> LENGTH: 22
<212> TYPE: RNA
<213> ORGANISM: Homo sapiens

<400> SEQUENCE: 9
```

-continued cagugcaaug augaaagggc au 22

<210> SEQ ID NO 10
<211> LENGTH: 22
<212> TYPE: RNA
<213> ORGANISM: Homo sapiens

<400> SEQUENCE: 10
uaccacaggg uagaaccacg ga 22

<210> SEQ ID NO 11
<211> LENGTH: 22
<212> TYPE: RNA
<213> ORGANISM: Homo sapiens

<400> SEQUENCE: 11
cccauaaagu agaaagcacu ac 22

<210> SEQ ID NO 12
<211> LENGTH: 22
<212> TYPE: RNA
<213> ORGANISM: Homo sapiens

<400> SEQUENCE: 12
ucgaggagcu cacagucuag ua 22

<210> SEQ ID NO 13
<211> LENGTH: 22
<212> TYPE: RNA
<213> ORGANISM: Homo sapiens

<400> SEQUENCE: 13
uuaaugcuaa ucgugauagg gg 22

<210> SEQ ID NO 14
<211> LENGTH: 22
<212> TYPE: RNA
<213> ORGANISM: Homo sapiens

<400> SEQUENCE: 14
aacauucaac gcugucggug ag 22

<210> SEQ ID NO 15
<211> LENGTH: 22
<212> TYPE: RNA
<213> ORGANISM: Homo sapiens

<400> SEQUENCE: 15
aacauucauu gcugucggug gg 22

<210> SEQ ID NO 16
<211> LENGTH: 22
<212> TYPE: RNA
<213> ORGANISM: Homo sapiens

<400> SEQUENCE: 16
aacauucaac cugucgguga gu 22

<210> SEQ ID NO 17
<211> LENGTH: 22
<212> TYPE: RNA
<213> ORGANISM: Homo sapiens

<400> SEQUENCE: 17

-continued uuuggcaaug guagaacuca ca                                    22

<210> SEQ ID NO 18
<211> LENGTH: 22
<212> TYPE: RNA
<213> ORGANISM: Homo sapiens

<400> SEQUENCE: 18
uauggcacug guagaauuca cu                                    22

<210> SEQ ID NO 19
<211> LENGTH: 22
<212> TYPE: RNA
<213> ORGANISM: Homo sapiens

<400> SEQUENCE: 19
uggacggaga acugauaagg gu                                    22

<210> SEQ ID NO 20
<211> LENGTH: 22
<212> TYPE: RNA
<213> ORGANISM: Homo sapiens

<400> SEQUENCE: 20
uggagagaaa ggcaguuccu ga                                    22

<210> SEQ ID NO 21
<211> LENGTH: 22
<212> TYPE: RNA
<213> ORGANISM: Homo sapiens

<400> SEQUENCE: 21
caaagaauuc uccuuuuggg cu                                    22

<210> SEQ ID NO 22
<211> LENGTH: 22
<212> TYPE: RNA
<213> ORGANISM: Homo sapiens

<400> SEQUENCE: 22
ucgugucuug uguugcagcc gg                                    22

<210> SEQ ID NO 23
<211> LENGTH: 22
<212> TYPE: RNA
<213> ORGANISM: Homo sapiens

<400> SEQUENCE: 23
cucccacaug caggguuugc ag                                    22

<210> SEQ ID NO 24
<211> LENGTH: 22
<212> TYPE: RNA
<213> ORGANISM: Homo sapiens

<400> SEQUENCE: 24
caucccuugc augguggagg gu                                    22

<210> SEQ ID NO 25
<211> LENGTH: 22
<212> TYPE: RNA
<213> ORGANISM: Homo sapiens -continued

```
<400> SEQUENCE: 25
gugccuacug agcugauauc ag                                              22

<210> SEQ ID NO 26
<211> LENGTH: 22
<212> TYPE: RNA
<213> ORGANISM: Homo sapiens

<400> SEQUENCE: 26
ugauauguuu gauauauuag gu                                              22

<210> SEQ ID NO 27
<211> LENGTH: 22
<212> TYPE: RNA
<213> ORGANISM: Homo sapiens

<400> SEQUENCE: 27
caacggaauc ccaaaagcag cu                                              22

<210> SEQ ID NO 28
<211> LENGTH: 22
<212> TYPE: RNA
<213> ORGANISM: Homo sapiens

<400> SEQUENCE: 28
cugaccuaug aauugacagc ca                                              22

<210> SEQ ID NO 29
<211> LENGTH: 22
<212> TYPE: RNA
<213> ORGANISM: Homo sapiens

<400> SEQUENCE: 29
aacuggccua caaaguccca gu                                              22

<210> SEQ ID NO 30
<211> LENGTH: 22
<212> TYPE: RNA
<213> ORGANISM: Homo sapiens

<400> SEQUENCE: 30
ugggucuuug cgggcaagau ga                                              22

<210> SEQ ID NO 31
<211> LENGTH: 22
<212> TYPE: RNA
<213> ORGANISM: Homo sapiens

<400> SEQUENCE: 31
uguaacagca acuccaugug ga                                              22

<210> SEQ ID NO 32
<211> LENGTH: 22
<212> TYPE: RNA
<213> ORGANISM: Homo sapiens

<400> SEQUENCE: 32
uagcagcaca gaaauauugg ca                                              22

<210> SEQ ID NO 33
<211> LENGTH: 22
<212> TYPE: RNA
<213> ORGANISM: Homo sapiens
```

<400> SEQUENCE: 33
uagguaguuu cauguuguug gg                                              22

<210> SEQ ID NO 34
<211> LENGTH: 22
<212> TYPE: RNA
<213> ORGANISM: Homo sapiens

<400> SEQUENCE: 34
uucaccaccu ucuccaccca gc                                              22

<210> SEQ ID NO 35
<211> LENGTH: 22
<212> TYPE: RNA
<213> ORGANISM: Homo sapiens

<400> SEQUENCE: 35
gguccagagg ggagauaggu uc                                              22

<210> SEQ ID NO 36
<211> LENGTH: 22
<212> TYPE: RNA
<213> ORGANISM: Homo sapiens

<400> SEQUENCE: 36
acaguagucu gcacauuggu ua                                              22

<210> SEQ ID NO 37
<211> LENGTH: 22
<212> TYPE: RNA
<213> ORGANISM: Homo sapiens

<400> SEQUENCE: 37
cccaguguuc agacuaccug uu                                              22

<210> SEQ ID NO 38
<211> LENGTH: 22
<212> TYPE: RNA
<213> ORGANISM: Homo sapiens

<400> SEQUENCE: 38
cccaguguuu agacuaucug uu                                              22

<210> SEQ ID NO 39
<211> LENGTH: 22
<212> TYPE: RNA
<213> ORGANISM: Homo sapiens

<400> SEQUENCE: 39
uaacacuguc ugguaacgau gu                                              22

<210> SEQ ID NO 40
<211> LENGTH: 22
<212> TYPE: RNA
<213> ORGANISM: Homo sapiens

<400> SEQUENCE: 40
cucuaauacu gccugguaau ga                                              22

<210> SEQ ID NO 41
<211> LENGTH: 22
<212> TYPE: RNA

<213> ORGANISM: Homo sapiens

<400> SEQUENCE: 41
aauacugccg gguaaugaug ga                                    22

<210> SEQ ID NO 42
<211> LENGTH: 22
<212> TYPE: RNA
<213> ORGANISM: Homo sapiens

<400> SEQUENCE: 42
gugaaauguu uaggaccacu ag                                    22

<210> SEQ ID NO 43
<211> LENGTH: 22
<212> TYPE: RNA
<213> ORGANISM: Homo sapiens

<400> SEQUENCE: 43
uucccuuugu cauccuaugc cu                                    22

<210> SEQ ID NO 44
<211> LENGTH: 22
<212> TYPE: RNA
<213> ORGANISM: Homo sapiens

<400> SEQUENCE: 44
uccuucauuc caccggaguc ug                                    22

<210> SEQ ID NO 45
<211> LENGTH: 22
<212> TYPE: RNA
<213> ORGANISM: Homo sapiens

<400> SEQUENCE: 45
uggaauguaa ggaagugugu gg                                    22

<210> SEQ ID NO 46
<211> LENGTH: 22
<212> TYPE: RNA
<213> ORGANISM: Homo sapiens

<400> SEQUENCE: 46
auaagacgag caaaaagcuu gu                                    22

<210> SEQ ID NO 47
<211> LENGTH: 22
<212> TYPE: RNA
<213> ORGANISM: Homo sapiens

<400> SEQUENCE: 47
cugugcgugu gacagcggcu ga                                    22

<210> SEQ ID NO 48
<211> LENGTH: 22
<212> TYPE: RNA
<213> ORGANISM: Homo sapiens

<400> SEQUENCE: 48
uucccuuugu cauccuucgc cu                                    22

<210> SEQ ID NO 49
<211> LENGTH: 22

```
<212> TYPE: RNA
<213> ORGANISM: Homo sapiens

<400> SEQUENCE: 49
uaacagucuc cagucacggc ca                                              22

<210> SEQ ID NO 50
<211> LENGTH: 22
<212> TYPE: RNA
<213> ORGANISM: Homo sapiens

<400> SEQUENCE: 50
accaucgacc guugauugua cc                                              22

<210> SEQ ID NO 51
<211> LENGTH: 22
<212> TYPE: RNA
<213> ORGANISM: Homo sapiens

<400> SEQUENCE: 51
acagcaggca cagacaggca gu                                              22

<210> SEQ ID NO 52
<211> LENGTH: 22
<212> TYPE: RNA
<213> ORGANISM: Homo sapiens

<400> SEQUENCE: 52
augaccuaug aauugacaga ca                                              22

<210> SEQ ID NO 53
<211> LENGTH: 22
<212> TYPE: RNA
<213> ORGANISM: Homo sapiens

<400> SEQUENCE: 53
uaaucucagc uggcaacugu ga                                              22

<210> SEQ ID NO 54
<211> LENGTH: 22
<212> TYPE: RNA
<213> ORGANISM: Homo sapiens

<400> SEQUENCE: 54
uacugcauca ggaacugauu gg                                              22

<210> SEQ ID NO 55
<211> LENGTH: 22
<212> TYPE: RNA
<213> ORGANISM: Homo sapiens

<400> SEQUENCE: 55
uugugcuuga ucuaaccaug ug                                              22

<210> SEQ ID NO 56
<211> LENGTH: 22
<212> TYPE: RNA
<213> ORGANISM: Homo sapiens

<400> SEQUENCE: 56
ugauugucca aacgcaauuc uu                                              22

<210> SEQ ID NO 57
```

<211> LENGTH: 22
<212> TYPE: RNA
<213> ORGANISM: Homo sapiens

<400> SEQUENCE: 57
ccacaccgua ucugacacuu ug        22

<210> SEQ ID NO 58
<211> LENGTH: 22
<212> TYPE: RNA
<213> ORGANISM: Homo sapiens

<400> SEQUENCE: 58
agcuacauug ucugcugggu uu        22

<210> SEQ ID NO 59
<211> LENGTH: 22
<212> TYPE: RNA
<213> ORGANISM: Homo sapiens

<400> SEQUENCE: 59
agcuacaucu ggcuacuggg uc        22

<210> SEQ ID NO 60
<211> LENGTH: 22
<212> TYPE: RNA
<213> ORGANISM: Homo sapiens

<400> SEQUENCE: 60
ugucaguuug ucaaauaccc ca        22

<210> SEQ ID NO 61
<211> LENGTH: 22
<212> TYPE: RNA
<213> ORGANISM: Homo sapiens

<400> SEQUENCE: 61
caagucacua gugguuccgu uu        22

<210> SEQ ID NO 62
<211> LENGTH: 22
<212> TYPE: RNA
<213> ORGANISM: Homo sapiens

<400> SEQUENCE: 62
aaggagcuca cagucuauug ag        22

<210> SEQ ID NO 63
<211> LENGTH: 22
<212> TYPE: RNA
<213> ORGANISM: Homo sapiens

<400> SEQUENCE: 63
cucaaacugu gggggcacuu uc        22

<210> SEQ ID NO 64
<211> LENGTH: 22
<212> TYPE: RNA
<213> ORGANISM: Homo sapiens

<400> SEQUENCE: 64
agggcccccc cucaauccug uu        22

```
<210> SEQ ID NO 65
<211> LENGTH: 22
<212> TYPE: RNA
<213> ORGANISM: Homo sapiens

<400> SEQUENCE: 65
ugguuuaccg ucccacauac au                                              22

<210> SEQ ID NO 66
<211> LENGTH: 22
<212> TYPE: RNA
<213> ORGANISM: Homo sapiens

<400> SEQUENCE: 66
cagugcaaua guauugucaa ag                                              22

<210> SEQ ID NO 67
<211> LENGTH: 22
<212> TYPE: RNA
<213> ORGANISM: Homo sapiens

<400> SEQUENCE: 67
uaagugcuuc cauguuuugg ug                                              22

<210> SEQ ID NO 68
<211> LENGTH: 22
<212> TYPE: RNA
<213> ORGANISM: Homo sapiens

<400> SEQUENCE: 68
uguaaacauc cuugacugga ag                                              22

<210> SEQ ID NO 69
<211> LENGTH: 22
<212> TYPE: RNA
<213> ORGANISM: Homo sapiens

<400> SEQUENCE: 69
aaaagcuggg uugagagggc ga                                              22

<210> SEQ ID NO 70
<211> LENGTH: 22
<212> TYPE: RNA
<213> ORGANISM: Homo sapiens

<400> SEQUENCE: 70
uaagccaggg auugugigguu cg                                             22

<210> SEQ ID NO 71
<211> LENGTH: 22
<212> TYPE: RNA
<213> ORGANISM: Homo sapiens

<400> SEQUENCE: 71
aaacaugaau ugcugcugua uc                                              22

<210> SEQ ID NO 72
<211> LENGTH: 22
<212> TYPE: RNA
<213> ORGANISM: Homo sapiens

<400> SEQUENCE: 72
gcacauuaca cggucgaccu cu                                              22
```

```
<210> SEQ ID NO 73
<211> LENGTH: 22
<212> TYPE: RNA
<213> ORGANISM: Homo sapiens

<400> SEQUENCE: 73
ccacugcccc aggugcugcu gg                                              22

<210> SEQ ID NO 74
<211> LENGTH: 22
<212> TYPE: RNA
<213> ORGANISM: Homo sapiens

<400> SEQUENCE: 74
cgcaucsccu agggcauugg ug                                              22

<210> SEQ ID NO 75
<211> LENGTH: 22
<212> TYPE: RNA
<213> ORGANISM: Homo sapiens

<400> SEQUENCE: 75
ccucugggcc cuuccuccag cc                                              22

<210> SEQ ID NO 76
<211> LENGTH: 22
<212> TYPE: RNA
<213> ORGANISM: Homo sapiens

<400> SEQUENCE: 76
cuggcccucu cugcccuucc gu                                              22

<210> SEQ ID NO 77
<211> LENGTH: 22
<212> TYPE: RNA
<213> ORGANISM: Homo sapiens

<400> SEQUENCE: 77
aacacaccca gcuaaccuuu uu                                              22

<210> SEQ ID NO 78
<211> LENGTH: 22
<212> TYPE: RNA
<213> ORGANISM: Homo sapiens

<400> SEQUENCE: 78
uggcaguguc uuagcugguu gu                                              22

<210> SEQ ID NO 79
<211> LENGTH: 22
<212> TYPE: RNA
<213> ORGANISM: Homo sapiens

<400> SEQUENCE: 79
aggcaguguc auuagcugau ug                                              22

<210> SEQ ID NO 80
<211> LENGTH: 22
<212> TYPE: RNA
<213> ORGANISM: Homo sapiens

<400> SEQUENCE: 80
aggcagugua guuagcugau ug                                              22
```

```
<210> SEQ ID NO 81
<211> LENGTH: 22
<212> TYPE: RNA
<213> ORGANISM: Homo sapiens

<400> SEQUENCE: 81
uauugcacuu gucccggccu gu                                                22

<210> SEQ ID NO 82
<211> LENGTH: 22
<212> TYPE: RNA
<213> ORGANISM: Homo sapiens

<400> SEQUENCE: 82
aaagugcugu ucgugcaggu ag                                                22

<210> SEQ ID NO 83
<211> LENGTH: 22
<212> TYPE: RNA
<213> ORGANISM: Homo sapiens

<400> SEQUENCE: 83
uucaacgggu auuuauugag ca                                                22

<210> SEQ ID NO 84
<211> LENGTH: 22
<212> TYPE: RNA
<213> ORGANISM: Homo sapiens

<400> SEQUENCE: 84
uuuggcacua gcacauuuuu gc                                                22

<210> SEQ ID NO 85
<211> LENGTH: 22
<212> TYPE: RNA
<213> ORGANISM: Homo sapiens

<400> SEQUENCE: 85
ugagguagua aguuguauug uu                                                22

<210> SEQ ID NO 86
<211> LENGTH: 22
<212> TYPE: RNA
<213> ORGANISM: Mouse

<400> SEQUENCE: 86
caaagugcua acagugcagg ua                                                22

<210> SEQ ID NO 87
<211> LENGTH: 22
<212> TYPE: RNA
<213> ORGANISM: Mouse

<400> SEQUENCE: 87
cccuguagaa ccgaauuugu gu                                                22

<210> SEQ ID NO 88
<211> LENGTH: 22
<212> TYPE: RNA
<213> ORGANISM: Mouse

<400> SEQUENCE: 88
```
uauggcuuuu cauuccuaug ug    22

<210> SEQ ID NO 89
<211> LENGTH: 22
<212> TYPE: RNA
<213> ORGANISM: Mouse

<400> SEQUENCE: 89
ucagugcauc acagaacuuu gu    22

<210> SEQ ID NO 90
<211> LENGTH: 22
<212> TYPE: RNA
<213> ORGANISM: Mouse

<400> SEQUENCE: 90
cuagacugag gcuccuugag ga    22

<210> SEQ ID NO 91
<211> LENGTH: 22
<212> TYPE: RNA
<213> ORGANISM: Mouse

<400> SEQUENCE: 91
uuaaugcuaa uugugauagg gg    22

<210> SEQ ID NO 92
<211> LENGTH: 22
<212> TYPE: RNA
<213> ORGANISM: Mouse

<400> SEQUENCE: 92
cccaguguuu agacuaccug uu    22

<210> SEQ ID NO 93
<211> LENGTH: 22
<212> TYPE: RNA
<213> ORGANISM: Mouse

<400> SEQUENCE: 93
uaauacugcc ugguaaugau ga    22

<210> SEQ ID NO 94
<211> LENGTH: 22
<212> TYPE: RNA
<213> ORGANISM: Mouse

<400> SEQUENCE: 94
ugaaauguuu aggaccacua ga    22

<210> SEQ ID NO 95
<211> LENGTH: 22
<212> TYPE: RNA
<213> ORGANISM: Mouse

<400> SEQUENCE: 95
uucccuuugu cauccuuugc cu    22

<210> SEQ ID NO 96
<211> LENGTH: 22
<212> TYPE: RNA
<213> ORGANISM: Mouse

<400> SEQUENCE: 96
uacugcauca ggaacugacu gg                                          22

<210> SEQ ID NO 97
<211> LENGTH: 22
<212> TYPE: RNA
<213> ORGANISM: Mouse

<400> SEQUENCE: 97
uaagucacua gugguuccgu uu                                          22

<210> SEQ ID NO 98
<211> LENGTH: 22
<212> TYPE: RNA
<213> ORGANISM: Mouse

<400> SEQUENCE: 98
cacuagauug ugagcugcug ga                                          22

<210> SEQ ID NO 99
<211> LENGTH: 22
<212> TYPE: RNA
<213> ORGANISM: Mouse

<400> SEQUENCE: 99
cucaaacuau gggggcacuu uu                                          22

<210> SEQ ID NO 100
<211> LENGTH: 22
<212> TYPE: RNA
<213> ORGANISM: Mouse

<400> SEQUENCE: 100
aaagugcuuc cacuugugu gc                                           22

<210> SEQ ID NO 101
<211> LENGTH: 22
<212> TYPE: RNA
<213> ORGANISM: Mouse

<400> SEQUENCE: 101
caucaaagug gaggcccucu cu                                          22

<210> SEQ ID NO 102
<211> LENGTH: 22
<212> TYPE: RNA
<213> ORGANISM: Mouse

<400> SEQUENCE: 102
aagugccgcc agguuuugag ug                                          22

<210> SEQ ID NO 103
<211> LENGTH: 22
<212> TYPE: RNA
<213> ORGANISM: Mouse

<400> SEQUENCE: 103
acucaaacug ggggcucuuu ug                                          22

<210> SEQ ID NO 104
<211> LENGTH: 22
<212> TYPE: RNA
<213> ORGANISM: Mouse

-continued

```
<400> SEQUENCE: 104
agugccgcag aguuuguagu gu                                              22

<210> SEQ ID NO 105
<211> LENGTH: 22
<212> TYPE: RNA
<213> ORGANISM: Mouse

<400> SEQUENCE: 105
aaagugcuuc ccuuuugugu gu                                              22

<210> SEQ ID NO 106
<211> LENGTH: 22
<212> TYPE: RNA
<213> ORGANISM: Mouse

<400> SEQUENCE: 106
aaagugcuac uacuuugag uc                                               22

<210> SEQ ID NO 107
<211> LENGTH: 22
<212> TYPE: RNA
<213> ORGANISM: Mouse

<400> SEQUENCE: 107
auguaugugu gcaugugcau gu                                              22

<210> SEQ ID NO 108
<211> LENGTH: 22
<212> TYPE: RNA
<213> ORGANISM: Mouse

<400> SEQUENCE: 108
ggcagaggag ggcuguucuu cc                                              22

<210> SEQ ID NO 109
<211> LENGTH: 22
<212> TYPE: RNA
<213> ORGANISM: Mouse

<400> SEQUENCE: 109
uaugcaaggg caagcucucu uc                                              22

<210> SEQ ID NO 110
<211> LENGTH: 22
<212> TYPE: RNA
<213> ORGANISM: Mouse

<400> SEQUENCE: 110
aggcaagaug cuggcauagc ug                                              22

<210> SEQ ID NO 111
<211> LENGTH: 22
<212> TYPE: RNA
<213> ORGANISM: Mouse

<400> SEQUENCE: 111
aaacaugaag cgcugcaaca cc                                              22

<210> SEQ ID NO 112
<211> LENGTH: 22
<212> TYPE: RNA
<213> ORGANISM: Mouse
```

```
<400> SEQUENCE: 112
ccuaguaggu gcucaguaag ug                                              22

<210> SEQ ID NO 113
<211> LENGTH: 22
<212> TYPE: RNA
<213> ORGANISM: Mouse

<400> SEQUENCE: 113 ccucuggcc cuuccuccag uc                                               22

<210> SEQ ID NO 114
<211> LENGTH: 22
<212> TYPE: RNA
<213> ORGANISM: Mouse

<400> SEQUENCE: 114
gcaaagcaca gggccugcag ag                                              22

<210> SEQ ID NO 115
<211> LENGTH: 22
<212> TYPE: RNA
<213> ORGANISM: Mouse

<400> SEQUENCE: 115
gccccugggc cuauccuaga ac                                              22

<210> SEQ ID NO 116
<211> LENGTH: 22
<212> TYPE: RNA
<213> ORGANISM: Mouse

<400> SEQUENCE: 116
uucagcuccu auaugaugcc uu                                              22

<210> SEQ ID NO 117
<211> LENGTH: 22
<212> TYPE: RNA
<213> ORGANISM: Mouse

<400> SEQUENCE: 117
uccagcauca gugauuuugu ug                                              22

<210> SEQ ID NO 118
<211> LENGTH: 22
<212> TYPE: RNA
<213> ORGANISM: Mouse

<400> SEQUENCE: 118
ucccuguccu ccaggagcuc ac                                              22

<210> SEQ ID NO 119
<211> LENGTH: 22
<212> TYPE: RNA
<213> ORGANISM: Mouse

<400> SEQUENCE: 119
uccgucucag uuacuuuaua gc                                              22

<210> SEQ ID NO 120
<211> LENGTH: 22
<212> TYPE: RNA
```

<213> ORGANISM: Mouse

<400> SEQUENCE: 120
ucgaucgguc ggucggucag uc    22

<210> SEQ ID NO 121
<211> LENGTH: 22
<212> TYPE: RNA
<213> ORGANISM: Mouse

<400> SEQUENCE: 121
ucucacacag aaaucgcacc cg    22

<210> SEQ ID NO 122
<211> LENGTH: 22
<212> TYPE: RNA
<213> ORGANISM: Mouse

<400> SEQUENCE: 122
ugaucuagcc aaagccugac ug    22

<210> SEQ ID NO 123
<211> LENGTH: 22
<212> TYPE: RNA
<213> ORGANISM: Mouse

<400> SEQUENCE: 123
ugcugacccc uaguccagug cu    22

<210> SEQ ID NO 124
<211> LENGTH: 22
<212> TYPE: RNA
<213> ORGANISM: Mouse

<400> SEQUENCE: 124
ugucugcccg agugccugcc uc    22

<210> SEQ ID NO 125
<211> LENGTH: 22
<212> TYPE: RNA
<213> ORGANISM: Mouse

<400> SEQUENCE: 125
uaggcagugu aauuagcuga uu    22

<210> SEQ ID NO 126
<211> LENGTH: 22
<212> TYPE: RNA
<213> ORGANISM: Mouse

<400> SEQUENCE: 126
uucacaaagc ccauacacuu uc    22

<210> SEQ ID NO 127
<211> LENGTH: 22
<212> TYPE: RNA
<213> ORGANISM: Mouse

<400> SEQUENCE: 127
ucccugagga gcccuuugag cc    22

<210> SEQ ID NO 128
<211> LENGTH: 22

-continued

<212> TYPE: RNA
<213> ORGANISM: Mouse

<400> SEQUENCE: 128
uggaagacuu gugauuugu ug                                        22

<210> SEQ ID NO 129
<211> LENGTH: 22
<212> TYPE: RNA
<213> ORGANISM: Mouse

<400> SEQUENCE: 129
uauugcacuu gucccggccu ga                                       22

<210> SEQ ID NO 130
<211> LENGTH: 22
<212> TYPE: RNA
<213> ORGANISM: Mouse

<400> SEQUENCE: 130
caaagugcug uucgugcagg ua                                       22

<210> SEQ ID NO 131
<211> LENGTH: 22
<212> TYPE: RNA
<213> ORGANISM: Rat

<400> SEQUENCE: 131
ccuugagggg caugagggua gu                                       22

<210> SEQ ID NO 132
<211> LENGTH: 22
<212> TYPE: RNA
<213> ORGANISM: Rat

<400> SEQUENCE: 132
guggugugcu aguuacuuuu gg                                       22

<210> SEQ ID NO 133
<211> LENGTH: 22
<212> TYPE: RNA
<213> ORGANISM: Rat

<400> SEQUENCE: 133
ucaagagcaa uaacgaaaaa ug                                       22

<210> SEQ ID NO 134
<211> LENGTH: 22
<212> TYPE: RNA
<213> ORGANISM: Rat

<400> SEQUENCE: 134
ucacccuucc auaucuaguc uc                                       22

<210> SEQ ID NO 135
<211> LENGTH: 22
<212> TYPE: RNA
<213> ORGANISM: Rat

<400> SEQUENCE: 135
ucucccuccg ugugcccagu au                                       22

<210> SEQ ID NO 136

-continued

```
<211> LENGTH: 22
<212> TYPE: RNA
<213> ORGANISM: Rat

<400> SEQUENCE: 136
ugucccucug ggucgcccag cu                                              22

<210> SEQ ID NO 137
<211> LENGTH: 22
<212> TYPE: RNA
<213> ORGANISM: Rat

<400> SEQUENCE: 137
cagcccugcu gucuuaaccu cu                                              22

<210> SEQ ID NO 138
<211> LENGTH: 22
<212> TYPE: RNA
<213> ORGANISM: Rat

<400> SEQUENCE: 138
agaguaguag guugcauagu ac                                              22

<210> SEQ ID NO 139
<211> LENGTH: 22
<212> TYPE: RNA
<213> ORGANISM: Homo sapiens

<400> SEQUENCE: 139
uuaucagaau cuccaggggu ac                                              22

<210> SEQ ID NO 140
<211> LENGTH: 22
<212> TYPE: RNA
<213> ORGANISM: Homo sapiens

<400> SEQUENCE: 140
aauccuugga accuaggugu ga                                              22

<210> SEQ ID NO 141
<211> LENGTH: 22
<212> TYPE: RNA
<213> ORGANISM: Homo sapiens

<400> SEQUENCE: 141
auugcacggu auccaucugu aa                                              22

<210> SEQ ID NO 142
<211> LENGTH: 22
<212> TYPE: RNA
<213> ORGANISM: Homo sapiens

<400> SEQUENCE: 142
cggcggggac ggcgauuggu cc                                              22

<210> SEQ ID NO 143
<211> LENGTH: 22
<212> TYPE: RNA
<213> ORGANISM: Homo sapiens

<400> SEQUENCE: 143
uaaugcsccu aaaaauccuu au                                              22
```

```
<210> SEQ ID NO 144
<211> LENGTH: 22
<212> TYPE: RNA
<213> ORGANISM: Homo sapiens

<400> SEQUENCE: 144
uaacugguug aacaacugaa cc                                              22

<210> SEQ ID NO 145
<211> LENGTH: 22
<212> TYPE: RNA
<213> ORGANISM: Caenorhabditis elegans

<400> SEQUENCE: 145
ugagguagua gguuguauag uu                                              22

<210> SEQ ID NO 146
<211> LENGTH: 22
<212> TYPE: RNA
<213> ORGANISM: Caenorhabditis elegans

<400> SEQUENCE: 146
ucccugagac cucaagugug ag                                              22

<210> SEQ ID NO 147
<211> LENGTH: 22
<212> TYPE: RNA
<213> ORGANISM: Caenorhabditis elegans

<400> SEQUENCE: 147
uggaauguaa agaaguaugu ag                                              22

<210> SEQ ID NO 148
<211> LENGTH: 22
<212> TYPE: RNA
<213> ORGANISM: Caenorhabditis elegans

<400> SEQUENCE: 148
uaucacagcc agcuuugaug ug                                              22

<210> SEQ ID NO 149
<211> LENGTH: 22
<212> TYPE: RNA
<213> ORGANISM: Caenorhabditis elegans

<400> SEQUENCE: 149
aggcagugug guuagcuggu ug                                              22

<210> SEQ ID NO 150
<211> LENGTH: 22
<212> TYPE: RNA
<213> ORGANISM: Caenorhabditis elegans

<400> SEQUENCE: 150
ucaccgggug gaaacuagca gu                                              22

<210> SEQ ID NO 151
<211> LENGTH: 22
<212> TYPE: RNA
<213> ORGANISM: Caenorhabditis elegans

<400> SEQUENCE: 151
ucaccgggug aaaauucgca ug                                              22
```

```
<210> SEQ ID NO 152
<211> LENGTH: 22
<212> TYPE: RNA
<213> ORGANISM: Caenorhabditis elegans

<400> SEQUENCE: 152 ucaccggpug aacacuugca gu                                              22

<210> SEQ ID NO 153
<211> LENGTH: 22
<212> TYPE: RNA
<213> ORGANISM: Caenorhabditis elegans

<400> SEQUENCE: 153
ucaccgggag aaaaacugga gu                                              22

<210> SEQ ID NO 154
<211> LENGTH: 22
<212> TYPE: RNA
<213> ORGANISM: Caenorhabditis elegans

<400> SEQUENCE: 154
ucaccgggug uaaaucagcu ug                                              22

<210> SEQ ID NO 155
<211> LENGTH: 22
<212> TYPE: RNA
<213> ORGANISM: Caenorhabditis elegans

<400> SEQUENCE: 155
ucaccgggug uacaucagcu aa                                              22

<210> SEQ ID NO 156
<211> LENGTH: 22
<212> TYPE: RNA
<213> ORGANISM: Caenorhabditis elegans

<400> SEQUENCE: 156
ucaccgggug aaaaaucacc ua                                              22

<210> SEQ ID NO 157
<211> LENGTH: 22
<212> TYPE: RNA
<213> ORGANISM: Caenorhabditis elegans

<400> SEQUENCE: 157
caccggguua acaucuacag ag                                              22

<210> SEQ ID NO 158
<211> LENGTH: 22
<212> TYPE: RNA
<213> ORGANISM: Caenorhabditis elegans

<400> SEQUENCE: 158
uaucacaguu uacuugcugu cg                                              22

<210> SEQ ID NO 159
<211> LENGTH: 22
<212> TYPE: RNA
<213> ORGANISM: Caenorhabditis elegans

<400> SEQUENCE: 159
ugacuagaga cacauucagc uu                                              22
```

```
<210> SEQ ID NO 160
<211> LENGTH: 22
<212> TYPE: RNA
<213> ORGANISM: Caenorhabditis elegans

<400> SEQUENCE: 160
ugacuagaga cacauucagc uu                                              22

<210> SEQ ID NO 161
<211> LENGTH: 22
<212> TYPE: RNA
<213> ORGANISM: Caenorhabditis elegans

<400> SEQUENCE: 161
ugucauggag ucgcucucuu ca                                              22

<210> SEQ ID NO 162
<211> LENGTH: 22
<212> TYPE: RNA
<213> ORGANISM: Caenorhabditis elegans

<400> SEQUENCE: 162
ugucauggag gcgcucucuu ca                                              22

<210> SEQ ID NO 163
<211> LENGTH: 22
<212> TYPE: RNA
<213> ORGANISM: Caenorhabditis elegans

<400> SEQUENCE: 163
ugagguaggc ucaguagaug cg                                              22

<210> SEQ ID NO 164
<211> LENGTH: 22
<212> TYPE: RNA
<213> ORGANISM: Caenorhabditis elegans

<400> SEQUENCE: 164
aagcaccacg agaagcugca ga                                              22

<210> SEQ ID NO 165
<211> LENGTH: 22
<212> TYPE: RNA
<213> ORGANISM: Caenorhabditis elegans

<400> SEQUENCE: 165
ugauaugucu gguauucuug gg                                              22

<210> SEQ ID NO 166
<211> LENGTH: 22
<212> TYPE: RNA
<213> ORGANISM: Caenorhabditis elegans

<400> SEQUENCE: 166
uacccguagc uccuauccau gu                                              22

<210> SEQ ID NO 167
<211> LENGTH: 22
<212> TYPE: RNA
<213> ORGANISM: Caenorhabditis elegans

<400> SEQUENCE: 167
```

-continued cacccguaca uauguuuccg ug                                    22

<210> SEQ ID NO 168
<211> LENGTH: 22
<212> TYPE: RNA
<213> ORGANISM: Caenorhabditis elegans

<400> SEQUENCE: 168
cacccguaca uuuguuuccg ug                                    22

<210> SEQ ID NO 169
<211> LENGTH: 22
<212> TYPE: RNA
<213> ORGANISM: Caenorhabditis elegans

<400> SEQUENCE: 169
uacccguaau cuucauaauc cg                                    22

<210> SEQ ID NO 170
<211> LENGTH: 22
<212> TYPE: RNA
<213> ORGANISM: Caenorhabditis elegans

<400> SEQUENCE: 170
uacccguaua aguuucugcu ga                                    22

<210> SEQ ID NO 171
<211> LENGTH: 22
<212> TYPE: RNA
<213> ORGANISM: Caenorhabditis elegans

<400> SEQUENCE: 171
uacccguaau guuuccgcug ag                                    22

<210> SEQ ID NO 172
<211> LENGTH: 22
<212> TYPE: RNA
<213> ORGANISM: Caenorhabditis elegans

<400> SEQUENCE: 172
uacccuguag aucgagcugu gu                                    22

<210> SEQ ID NO 173
<211> LENGTH: 22
<212> TYPE: RNA
<213> ORGANISM: Caenorhabditis elegans

<400> SEQUENCE: 173
ugagaucguu caguacggca au                                    22

<210> SEQ ID NO 174
<211> LENGTH: 22
<212> TYPE: RNA
<213> ORGANISM: Caenorhabditis elegans

<400> SEQUENCE: 174
ucgaaucguu uaucaggaug au                                    22

<210> SEQ ID NO 175
<211> LENGTH: 22
<212> TYPE: RNA
<213> ORGANISM: Caenorhabditis elegans

<400> SEQUENCE: 175

```
uauuaugcac auuuucuagu uc                                              22

<210> SEQ ID NO 176
<211> LENGTH: 22
<212> TYPE: RNA
<213> ORGANISM: Caenorhabditis elegans

<400> SEQUENCE: 176
ugacuagaac cguuacucau cu                                              22

<210> SEQ ID NO 177
<211> LENGTH: 22
<212> TYPE: RNA
<213> ORGANISM: Caenorhabditis elegans

<400> SEQUENCE: 177
ugauauguaa ucuagcuuac ag                                              22

<210> SEQ ID NO 178
<211> LENGTH: 22
<212> TYPE: RNA
<213> ORGANISM: Caenorhabditis elegans

<400> SEQUENCE: 178
augacacuga agcgaguugg aa                                              22

<210> SEQ ID NO 179
<211> LENGTH: 22
<212> TYPE: RNA
<213> ORGANISM: Caenorhabditis elegans

<400> SEQUENCE: 179
uaugacacug aagcguuacc ga                                              22

<210> SEQ ID NO 180
<211> LENGTH: 22
<212> TYPE: RNA
<213> ORGANISM: Caenorhabditis elegans

<400> SEQUENCE: 180
uaugacacug aagcguaacc ga                                              22

<210> SEQ ID NO 181
<211> LENGTH: 22
<212> TYPE: RNA
<213> ORGANISM: Caenorhabditis elegans

<400> SEQUENCE: 181
caugacacug auuagggaug ug                                              22

<210> SEQ ID NO 182
<211> LENGTH: 22
<212> TYPE: RNA
<213> ORGANISM: Caenorhabditis elegans

<400> SEQUENCE: 182
ucacaaccuc cuagaaagag ua                                              22

<210> SEQ ID NO 183
<211> LENGTH: 22
<212> TYPE: RNA
<213> ORGANISM: Caenorhabditis elegans
```

-continued

```
<400> SEQUENCE: 183
ucgaagacuc aaaaguguag ac                                              22

<210> SEQ ID NO 184
<211> LENGTH: 22
<212> TYPE: RNA
<213> ORGANISM: Caenorhabditis elegans

<400> SEQUENCE: 184
ucgaaaauua aaaguguag aa                                               22

<210> SEQ ID NO 185
<211> LENGTH: 22
<212> TYPE: RNA
<213> ORGANISM: Caenorhabditis elegans

<400> SEQUENCE: 185
uaauacgucg uugguguuuc ca                                              22

<210> SEQ ID NO 186
<211> LENGTH: 22
<212> TYPE: RNA
<213> ORGANISM: Caenorhabditis elegans

<400> SEQUENCE: 186
ugaaagacau ggguagugaa cg                                              22

<210> SEQ ID NO 187
<211> LENGTH: 22
<212> TYPE: RNA
<213> ORGANISM: Caenorhabditis elegans

<400> SEQUENCE: 187
aggcaagaug uuggcauagc ug                                              22

<210> SEQ ID NO 188
<211> LENGTH: 22
<212> TYPE: RNA
<213> ORGANISM: Caenorhabditis elegans

<400> SEQUENCE: 188
uggcaagaug uaggcaguuc ag                                              22

<210> SEQ ID NO 189
<211> LENGTH: 22
<212> TYPE: RNA
<213> ORGANISM: Caenorhabditis elegans

<400> SEQUENCE: 189
uggcaagaaa uggcagucua ca                                              22

<210> SEQ ID NO 190
<211> LENGTH: 22
<212> TYPE: RNA
<213> ORGANISM: Caenorhabditis elegans

<400> SEQUENCE: 190
uuaaagcuac caaccggcuu ca                                              22

<210> SEQ ID NO 191
<211> LENGTH: 22
<212> TYPE: RNA
<213> ORGANISM: Caenorhabditis elegans
```

<400> SEQUENCE: 191
uucguuguug augaagccuu ga                    22

<210> SEQ ID NO 192
<211> LENGTH: 22
<212> TYPE: RNA
<213> ORGANISM: Caenorhabditis elegans

<400> SEQUENCE: 192
uucaucaggc cauagcuguc ca                    22

<210> SEQ ID NO 193
<211> LENGTH: 22
<212> TYPE: RNA
<213> ORGANISM: Caenorhabditis elegans

<400> SEQUENCE: 193
uggaggccug guuguuugug cu                    22

<210> SEQ ID NO 194
<211> LENGTH: 22
<212> TYPE: RNA
<213> ORGANISM: Caenorhabditis elegans

<400> SEQUENCE: 194
auaaagcuag guuaccaaag cu                    22

<210> SEQ ID NO 195
<211> LENGTH: 22
<212> TYPE: RNA
<213> ORGANISM: Caenorhabditis elegans

<400> SEQUENCE: 195
agcuuucgac augauucuga ac                    22

<210> SEQ ID NO 196
<211> LENGTH: 22
<212> TYPE: RNA
<213> ORGANISM: Caenorhabditis elegans

<400> SEQUENCE: 196
ugagaucauu aguugaaagc cg                    22

<210> SEQ ID NO 197
<211> LENGTH: 22
<212> TYPE: RNA
<213> ORGANISM: Caenorhabditis elegans

<400> SEQUENCE: 197
ugagaucauc gugaaagcua gu                    22

<210> SEQ ID NO 198
<211> LENGTH: 22
<212> TYPE: RNA
<213> ORGANISM: Caenorhabditis elegans

<400> SEQUENCE: 198
ugagaucauc gugaaagcca gu                    22

<210> SEQ ID NO 199
<211> LENGTH: 22
<212> TYPE: RNA

<213> ORGANISM: Caenorhabditis elegans

<400> SEQUENCE: 199
uagcaccaua uaaauucagu aa    22

<210> SEQ ID NO 200
<211> LENGTH: 22
<212> TYPE: RNA
<213> ORGANISM: Caenorhabditis elegans

<400> SEQUENCE: 200
ugagguagua uguaauauug ua    22

<210> SEQ ID NO 201
<211> LENGTH: 22
<212> TYPE: RNA
<213> ORGANISM: Caenorhabditis elegans

<400> SEQUENCE: 201
uacaaaguau uugaaaaguc gu    22

<210> SEQ ID NO 202
<211> LENGTH: 22
<212> TYPE: RNA
<213> ORGANISM: Caenorhabditis elegans

<400> SEQUENCE: 202
uaagugaaug cuuugccaca gu    22

<210> SEQ ID NO 203
<211> LENGTH: 22
<212> TYPE: RNA
<213> ORGANISM: Caenorhabditis elegans

<400> SEQUENCE: 203
gugagcaaag uuucaggugu gc    22

<210> SEQ ID NO 204
<211> LENGTH: 22
<212> TYPE: RNA
<213> ORGANISM: Caenorhabditis elegans

<400> SEQUENCE: 204
ugauauguug uuugaaugcc cc    22

<210> SEQ ID NO 205
<211> LENGTH: 22
<212> TYPE: RNA
<213> ORGANISM: Caenorhabditis elegans

<400> SEQUENCE: 205
uaaggcacgc ggugaaugcc ac    22

<210> SEQ ID NO 206
<211> LENGTH: 22
<212> TYPE: RNA
<213> ORGANISM: Caenorhabditis elegans

<400> SEQUENCE: 206
aauggcacug caugaauuca cg    22

<210> SEQ ID NO 207
<211> LENGTH: 22

-continued

```
<212> TYPE: RNA
<213> ORGANISM: Caenorhabditis elegans

<400> SEQUENCE: 207
aaugacacug guuaucuuuu cc                                              22

<210> SEQ ID NO 208
<211> LENGTH: 22
<212> TYPE: RNA
<213> ORGANISM: Caenorhabditis elegans

<400> SEQUENCE: 208
guauuaguug ugcgaccagg ag                                              22

<210> SEQ ID NO 209
<211> LENGTH: 22
<212> TYPE: RNA
<213> ORGANISM: Caenorhabditis elegans

<400> SEQUENCE: 209
uaagcucgug aucaacaggc ag                                              22

<210> SEQ ID NO 210
<211> LENGTH: 22
<212> TYPE: RNA
<213> ORGANISM: Caenorhabditis elegans

<400> SEQUENCE: 210
uaaaugcauc uuaacugcgg ug                                              22

<210> SEQ ID NO 211
<211> LENGTH: 22
<212> TYPE: RNA
<213> ORGANISM: Caenorhabditis elegans

<400> SEQUENCE: 211
uugagcaaug cgcaugugcg gg                                              22

<210> SEQ ID NO 212
<211> LENGTH: 22
<212> TYPE: RNA
<213> ORGANISM: Caenorhabditis elegans

<400> SEQUENCE: 212
uuauugcucg agaauacccu uu                                              22

<210> SEQ ID NO 213
<211> LENGTH: 22
<212> TYPE: RNA
<213> ORGANISM: Caenorhabditis elegans

<400> SEQUENCE: 213
uauugcacuc uccccggccu ga                                              22

<210> SEQ ID NO 214
<211> LENGTH: 22
<212> TYPE: RNA
<213> ORGANISM: Caenorhabditis elegans

<400> SEQUENCE: 214
uaauacuguc agguaaugac gc                                              22

<210> SEQ ID NO 215
```

-continued

<211> LENGTH: 22
<212> TYPE: RNA
<213> ORGANISM: Caenorhabditis elegans

<400> SEQUENCE: 215
ucccugagaa uucucgaaca gc                                              22

<210> SEQ ID NO 216
<211> LENGTH: 22
<212> TYPE: RNA
<213> ORGANISM: Caenorhabditis elegans

<400> SEQUENCE: 216
uuuguacucc gaugccauuc ag                                              22

<210> SEQ ID NO 217
<211> LENGTH: 22
<212> TYPE: RNA
<213> ORGANISM: Caenorhabditis elegans

<400> SEQUENCE: 217
uuuguacuac acauagguac ug                                              22

<210> SEQ ID NO 218
<211> LENGTH: 22
<212> TYPE: RNA
<213> ORGANISM: Caenorhabditis elegans

<400> SEQUENCE: 218
uuuguacuac acaaaaguac ug                                              22

<210> SEQ ID NO 219
<211> LENGTH: 22
<212> TYPE: RNA
<213> ORGANISM: Caenorhabditis elegans

<400> SEQUENCE: 219
uacuggcccc caaaucuucg cu                                              22

<210> SEQ ID NO 220
<211> LENGTH: 22
<212> TYPE: RNA
<213> ORGANISM: Caenorhabditis elegans

<400> SEQUENCE: 220
ugagguaggu gcgagaaaug ac                                              22

<210> SEQ ID NO 221
<211> LENGTH: 22
<212> TYPE: RNA
<213> ORGANISM: Caenorhabditis elegans

<400> SEQUENCE: 221
uugcguaggc cuuugcuucg ag                                              22

<210> SEQ ID NO 222
<211> LENGTH: 22
<212> TYPE: RNA
<213> ORGANISM: Caenorhabditis elegans

<400> SEQUENCE: 222
cgguacgauc gcggcgggau au                                              22

```
<210> SEQ ID NO 223
<211> LENGTH: 22
<212> TYPE: RNA
<213> ORGANISM: Caenorhabditis elegans

<400> SEQUENCE: 223
ucuuugguug uacaaagugg ua                                              22

<210> SEQ ID NO 224
<211> LENGTH: 22
<212> TYPE: RNA
<213> ORGANISM: Caenorhabditis elegans

<400> SEQUENCE: 224
auuggucccc uccaaguagc uc                                              22

<210> SEQ ID NO 225
<211> LENGTH: 22
<212> TYPE: RNA
<213> ORGANISM: Caenorhabditis elegans

<400> SEQUENCE: 225
uuacauguuu cggguaggag cu                                              22

<210> SEQ ID NO 226
<211> LENGTH: 22
<212> TYPE: RNA
<213> ORGANISM: Caenorhabditis elegans

<400> SEQUENCE: 226
ugacuagagc cuauucucuu cu                                              22

<210> SEQ ID NO 227
<211> LENGTH: 22
<212> TYPE: RNA
<213> ORGANISM: Caenorhabditis elegans

<400> SEQUENCE: 227
uacacgugca cggauaacgc uc                                              22

<210> SEQ ID NO 228
<211> LENGTH: 22
<212> TYPE: RNA
<213> ORGANISM: Caenorhabditis elegans

<400> SEQUENCE: 228
ucacaggacu uuugagcguu gc                                              22

<210> SEQ ID NO 229
<211> LENGTH: 22
<212> TYPE: RNA
<213> ORGANISM: Caenorhabditis elegans

<400> SEQUENCE: 229
ucacagucaa cuguuggcau gg                                              22

<210> SEQ ID NO 230
<211> LENGTH: 22
<212> TYPE: RNA
<213> ORGANISM: Caenorhabditis elegans

<400> SEQUENCE: 230
uuaaguagug gugccgcucu ua                                              22
```

```
<210> SEQ ID NO 231
<211> LENGTH: 22
<212> TYPE: RNA
<213> ORGANISM: Caenorhabditis elegans

<400> SEQUENCE: 231
uaaguaguag ugccgcaggu aa                                              22

<210> SEQ ID NO 232
<211> LENGTH: 22
<212> TYPE: RNA
<213> ORGANISM: Caenorhabditis elegans

<400> SEQUENCE: 232
cacaccucac uaacacugac ca                                              22

<210> SEQ ID NO 233
<211> LENGTH: 22
<212> TYPE: RNA
<213> ORGANISM: Caenorhabditis elegans

<400> SEQUENCE: 233
ugcaaaucuu ucgcgacugu ag                                              22

<210> SEQ ID NO 234
<211> LENGTH: 22
<212> TYPE: RNA
<213> ORGANISM: Caenorhabditis elegans

<400> SEQUENCE: 234
uggaaugcau agaagacugu ac                                              22

<210> SEQ ID NO 235
<211> LENGTH: 22
<212> TYPE: RNA
<213> ORGANISM: Caenorhabditis elegans

<400> SEQUENCE: 235
gaguaucagg aguacccagu ga                                              22

<210> SEQ ID NO 236
<211> LENGTH: 22
<212> TYPE: RNA
<213> ORGANISM: Caenorhabditis elegans

<400> SEQUENCE: 236
gguuuugaga ggaauccuuu ua                                              22

<210> SEQ ID NO 237
<211> LENGTH: 22
<212> TYPE: RNA
<213> ORGANISM: Caenorhabditis elegans

<400> SEQUENCE: 237
aguaaaucuc auccuaaucu gg                                              22

<210> SEQ ID NO 238
<211> LENGTH: 22
<212> TYPE: RNA
<213> ORGANISM: Caenorhabditis elegans

<400> SEQUENCE: 238
gugaugucga acucuuguag ga                                              22
```

<210> SEQ ID NO 239
<211> LENGTH: 22
<212> TYPE: RNA
<213> ORGANISM: Caenorhabditis elegans

<400> SEQUENCE: 239
uagcuuuuua guuucacgg ug                                              22

<210> SEQ ID NO 240
<211> LENGTH: 22
<212> TYPE: RNA
<213> ORGANISM: Caenorhabditis elegans

<400> SEQUENCE: 240
guuucucgau guuucugau ac                                              22

<210> SEQ ID NO 241
<211> LENGTH: 22
<212> TYPE: RNA
<213> ORGANISM: Caenorhabditis elegans

<400> SEQUENCE: 241
ggcggguggu uguuguuaug gg                                             22

<210> SEQ ID NO 242
<211> LENGTH: 22
<212> TYPE: RNA
<213> ORGANISM: Caenorhabditis elegans

<400> SEQUENCE: 242
ugagggagga agguggguau uu                                             22

<210> SEQ ID NO 243
<211> LENGTH: 22
<212> TYPE: RNA
<213> ORGANISM: Caenorhabditis elegans

<400> SEQUENCE: 243
aggcaagacu uuggcaaagc uu                                             22

<210> SEQ ID NO 244
<211> LENGTH: 22
<212> TYPE: RNA
<213> ORGANISM: Caenorhabditis elegans

<400> SEQUENCE: 244
cccgugaagu gucugcugca au                                             22

<210> SEQ ID NO 245
<211> LENGTH: 22
<212> TYPE: RNA
<213> ORGANISM: Caenorhabditis elegans

<400> SEQUENCE: 245
ggcaagaauu agaagcaguu ug                                             22

<210> SEQ ID NO 246
<211> LENGTH: 22
<212> TYPE: RNA
<213> ORGANISM: Caenorhabditis elegans

<400> SEQUENCE: 246
ggcaagacuc uggcaaaacu ug                                        22

<210> SEQ ID NO 247
<211> LENGTH: 22
<212> TYPE: RNA
<213> ORGANISM: Caenorhabditis elegans

<400> SEQUENCE: 247
ggcaugaugu agcaguggag au                                        22

<210> SEQ ID NO 248
<211> LENGTH: 22
<212> TYPE: RNA
<213> ORGANISM: Caenorhabditis elegans

<400> SEQUENCE: 248
ucgccgggug ggaaagcauu cg                                        22

<210> SEQ ID NO 249
<211> LENGTH: 22
<212> TYPE: RNA
<213> ORGANISM: Caenorhabditis elegans

<400> SEQUENCE: 249
uguaggcaug gguguuugga ag                                        22

<210> SEQ ID NO 250
<211> LENGTH: 22
<212> TYPE: RNA
<213> ORGANISM: Caenorhabditis elegans

<400> SEQUENCE: 250
ugcccguacu gugucggcug cu                                        22

<210> SEQ ID NO 251
<211> LENGTH: 22
<212> TYPE: RNA
<213> ORGANISM: Drosophila melanogaster

<400> SEQUENCE: 251
guuaauggca cuggaagaau uc                                        22

<210> SEQ ID NO 252
<211> LENGTH: 22
<212> TYPE: RNA
<213> ORGANISM: Drosophila melanogaster

<400> SEQUENCE: 252
uggacggaga acugauaagg gc                                        22

<210> SEQ ID NO 253
<211> LENGTH: 22
<212> TYPE: RNA
<213> ORGANISM: Drosophila melanogaster

<400> SEQUENCE: 253
uuuugugacc gacacuaacg gg                                        22

<210> SEQ ID NO 254
<211> LENGTH: 22
<212> TYPE: RNA
<213> ORGANISM: Drosophila melanogaster

<400> SEQUENCE: 254

-continued ucagguaccu gaaguagcgc gc                                          22

<210> SEQ ID NO 255
<211> LENGTH: 22
<212> TYPE: RNA
<213> ORGANISM: Drosophila melanogaster

<400> SEQUENCE: 255
cauugcacuu gucccggccu au                                          22

<210> SEQ ID NO 256
<211> LENGTH: 22
<212> TYPE: RNA
<213> ORGANISM: Drosophila melanogaster

<400> SEQUENCE: 256
ugauugucca aacgcaauuc uu                                          22

<210> SEQ ID NO 257
<211> LENGTH: 22
<212> TYPE: RNA
<213> ORGANISM: Drosophila melanogaster

<400> SEQUENCE: 257
uaggaacuuc auaccgugcu cu                                          22

<210> SEQ ID NO 258
<211> LENGTH: 22
<212> TYPE: RNA
<213> ORGANISM: Drosophila melanogaster

<400> SEQUENCE: 258
uaaaugcacu aucggguacg ac                                          22

<210> SEQ ID NO 259
<211> LENGTH: 22
<212> TYPE: RNA
<213> ORGANISM: Drosophila melanogaster

<400> SEQUENCE: 259
ucggugggac uuucguccgu uu                                          22

<210> SEQ ID NO 260
<211> LENGTH: 22
<212> TYPE: RNA
<213> ORGANISM: Drosophila melanogaster

<400> SEQUENCE: 260
uuggucsccu ucaaccagcu gu                                          22

<210> SEQ ID NO 261
<211> LENGTH: 22
<212> TYPE: RNA
<213> ORGANISM: Drosophila melanogaster

<400> SEQUENCE: 261
ugacuagauc cacacucauu aa                                          22

<210> SEQ ID NO 262
<211> LENGTH: 22
<212> TYPE: RNA
<213> ORGANISM: Drosophila melanogaster

```
<400> SEQUENCE: 262
aggugcauug uagucgcauu gu                                      22

<210> SEQ ID NO 263
<211> LENGTH: 22
<212> TYPE: RNA
<213> ORGANISM: Drosophila melanogaster

<400> SEQUENCE: 263
uguauuuacg uugcauauga aa                                      22

<210> SEQ ID NO 264
<211> LENGTH: 22
<212> TYPE: RNA
<213> ORGANISM: Drosophila melanogaster

<400> SEQUENCE: 264
ugucauggaa uugcucucuu ug                                      22

<210> SEQ ID NO 265
<211> LENGTH: 22
<212> TYPE: RNA
<213> ORGANISM: Drosophila melanogaster

<400> SEQUENCE: 265
aaucuagccu cuacuaggcu uu                                      22

<210> SEQ ID NO 266
<211> LENGTH: 22
<212> TYPE: RNA
<213> ORGANISM: Drosophila melanogaster

<400> SEQUENCE: 266
uaaauaucag cugguaauuc ug                                      22

<210> SEQ ID NO 267
<211> LENGTH: 22
<212> TYPE: RNA
<213> ORGANISM: Drosophila melanogaster

<400> SEQUENCE: 267
ugaagucagc aacuugauuc ca                                      22

<210> SEQ ID NO 268
<211> LENGTH: 22
<212> TYPE: RNA
<213> ORGANISM: Drosophila melanogaster

<400> SEQUENCE: 268
uggcagugug guuagcuggu ug                                      22

<210> SEQ ID NO 269
<211> LENGTH: 22
<212> TYPE: RNA
<213> ORGANISM: Drosophila melanogaster

<400> SEQUENCE: 269
uaaggcacgc ggugaaugcc aa                                      22

<210> SEQ ID NO 270
<211> LENGTH: 22
<212> TYPE: RNA
<213> ORGANISM: Drosophila melanogaster
```

<400> SEQUENCE: 270
uaaagcuaga uuaccaaagc au                                                    22

<210> SEQ ID NO 271
<211> LENGTH: 22
<212> TYPE: RNA
<213> ORGANISM: Drosophila melanogaster

<400> SEQUENCE: 271
uaggaacuua auaccgugcu cu                                                    22

<210> SEQ ID NO 272
<211> LENGTH: 22
<212> TYPE: RNA
<213> ORGANISM: Drosophila melanogaster

<400> SEQUENCE: 272
uugugcgugu gacagcggcu au                                                    22

<210> SEQ ID NO 273
<211> LENGTH: 22
<212> TYPE: RNA
<213> ORGANISM: Drosophila melanogaster

<400> SEQUENCE: 273
uagcaccauu cgaaaucagu gc                                                    22

<210> SEQ ID NO 274
<211> LENGTH: 22
<212> TYPE: RNA
<213> ORGANISM: Drosophila melanogaster

<400> SEQUENCE: 274
aacccguaaa uccgaacuug ug                                                    22

<210> SEQ ID NO 275
<211> LENGTH: 22
<212> TYPE: RNA
<213> ORGANISM: Drosophila melanogaster

<400> SEQUENCE: 275
aauugcacua gucccggccu gc                                                    22

<210> SEQ ID NO 276
<211> LENGTH: 22
<212> TYPE: RNA
<213> ORGANISM: Drosophila melanogaster

<400> SEQUENCE: 276
ugacuagacc gaacacucgu gc                                                    22

<210> SEQ ID NO 277
<211> LENGTH: 22
<212> TYPE: RNA
<213> ORGANISM: Drosophila melanogaster

<400> SEQUENCE: 277
uguguugaaa aucguuugca cg                                                    22

<210> SEQ ID NO 278
<211> LENGTH: 22
<212> TYPE: RNA

-continued

<213> ORGANISM: Drosophila melanogaster

<400> SEQUENCE: 278
uugagcaaaa uuucaggugu gu                                              22

<210> SEQ ID NO 279
<211> LENGTH: 22
<212> TYPE: RNA
<213> ORGANISM: Drosophila melanogaster

<400> SEQUENCE: 279
cuuggcacug ggagaauuca ca                                              22

<210> SEQ ID NO 280
<211> LENGTH: 22
<212> TYPE: RNA
<213> ORGANISM: Drosophila melanogaster

<400> SEQUENCE: 280
uuucaugucg auuucauuuc au                                              22

<210> SEQ ID NO 281
<211> LENGTH: 22
<212> TYPE: RNA
<213> ORGANISM: Drosophila melanogaster

<400> SEQUENCE: 281
uaaauauuua aguggagccu gc                                              22

<210> SEQ ID NO 282
<211> LENGTH: 22
<212> TYPE: RNA
<213> ORGANISM: Drosophila melanogaster

<400> SEQUENCE: 282
ugagaucauu uugaaagcug au                                              22

<210> SEQ ID NO 283
<211> LENGTH: 22
<212> TYPE: RNA
<213> ORGANISM: Drosophila melanogaster

<400> SEQUENCE: 283
uuuagguuuc acaggaaacu gg                                              22

<210> SEQ ID NO 284
<211> LENGTH: 22
<212> TYPE: RNA
<213> ORGANISM: Drosophila melanogaster

<400> SEQUENCE: 284
uggcaagaug ucggaauagc ug                                              22

<210> SEQ ID NO 285
<211> LENGTH: 22
<212> TYPE: RNA
<213> ORGANISM: Drosophila melanogaster

<400> SEQUENCE: 285
uaaucucaau uuguaaaugu ga                                              22

<210> SEQ ID NO 286
<211> LENGTH: 22

-continued

```
<212> TYPE: RNA
<213> ORGANISM: Drosophila melanogaster

<400> SEQUENCE: 286
auuguacuuc aucaggugcu cu                                              22

<210> SEQ ID NO 287
<211> LENGTH: 22
<212> TYPE: RNA
<213> ORGANISM: Drosophila melanogaster

<400> SEQUENCE: 287
ucuuugguau ucuagcugua ga                                              22

<210> SEQ ID NO 288
<211> LENGTH: 22
<212> TYPE: RNA
<213> ORGANISM: Drosophila melanogaster

<400> SEQUENCE: 288
ucagguacuu agugacucuc aa                                              22

<210> SEQ ID NO 289
<211> LENGTH: 22
<212> TYPE: RNA
<213> ORGANISM: Drosophila melanogaster

<400> SEQUENCE: 289
ucuuugguga uuuuagcugu au                                              22

<210> SEQ ID NO 290
<211> LENGTH: 22
<212> TYPE: RNA
<213> ORGANISM: Drosophila melanogaster

<400> SEQUENCE: 290
ucccugagac ccuaacuugu ga                                              22

<210> SEQ ID NO 291
<211> LENGTH: 22
<212> TYPE: RNA
<213> ORGANISM: Drosophila melanogaster

<400> SEQUENCE: 291
ucacaaccuc cuugagugag cg                                              22

<210> SEQ ID NO 292
<211> LENGTH: 22
<212> TYPE: RNA
<213> ORGANISM: Drosophila melanogaster

<400> SEQUENCE: 292
aaucacagga uuauacugug ag                                              22

<210> SEQ ID NO 293
<211> LENGTH: 22
<212> TYPE: RNA
<213> ORGANISM: Drosophila melanogaster

<400> SEQUENCE: 293
uggcaagaug ucggcauagc ug                                              22

<210> SEQ ID NO 294
```

```
<211> LENGTH: 22
<212> TYPE: RNA
<213> ORGANISM: Drosophila melanogaster

<400> SEQUENCE: 294
gcacugggua aaguuugucc ua                                              22

<210> SEQ ID NO 295
<211> LENGTH: 22
<212> TYPE: RNA
<213> ORGANISM: Drosophila melanogaster

<400> SEQUENCE: 295
uauugcacac uucccggccu uu                                              22

<210> SEQ ID NO 296
<211> LENGTH: 22
<212> TYPE: RNA
<213> ORGANISM: Drosophila melanogaster

<400> SEQUENCE: 296
uauugcacau ucaccggccu ga                                              22

<210> SEQ ID NO 297
<211> LENGTH: 22
<212> TYPE: RNA
<213> ORGANISM: Drosophila melanogaster

<400> SEQUENCE: 297
uauugcacuu gagacggccu ga                                              22

<210> SEQ ID NO 298
<211> LENGTH: 22
<212> TYPE: RNA
<213> ORGANISM: Drosophila melanogaster

<400> SEQUENCE: 298
uauugcacuu uucacagccc ga                                              22

<210> SEQ ID NO 299
<211> LENGTH: 21
<212> TYPE: RNA
<213> ORGANISM: Drosophila melanogaster

<400> SEQUENCE: 299
uauucgagcc aauaaguucg g                                               21

<210> SEQ ID NO 300
<211> LENGTH: 22
<212> TYPE: RNA
<213> ORGANISM: Drosophila melanogaster

<400> SEQUENCE: 300
uuuugauugu ugcucagaaa gc                                              22

<210> SEQ ID NO 301
<211> LENGTH: 22
<212> TYPE: RNA
<213> ORGANISM: Drosophila melanogaster

<400> SEQUENCE: 301
ugucuuuuuc cgcuuacugg cg                                              22
```

```
<210> SEQ ID NO 302
<211> LENGTH: 22
<212> TYPE: RNA
<213> ORGANISM: Drosophila melanogaster

<400> SEQUENCE: 302
ugaacacagc uggugguauc ca                                              22

<210> SEQ ID NO 303
<211> LENGTH: 22
<212> TYPE: RNA
<213> ORGANISM: Drosophila melanogaster

<400> SEQUENCE: 303
ucacugggcu uuguuuaucu ca                                              22

<210> SEQ ID NO 304
<211> LENGTH: 22
<212> TYPE: RNA
<213> ORGANISM: Drosophila melanogaster

<400> SEQUENCE: 304
uaucacagcc agcuuugaug gg                                              22

<210> SEQ ID NO 305
<211> LENGTH: 22
<212> TYPE: RNA
<213> ORGANISM: Drosophila melanogaster

<400> SEQUENCE: 305
acguauacug aauguauccu ga                                              22

<210> SEQ ID NO 306
<211> LENGTH: 22
<212> TYPE: RNA
<213> ORGANISM: Drosophila melanogaster

<400> SEQUENCE: 306
cgguauaccu ucaguauacg ua                                              22

<210> SEQ ID NO 307
<211> LENGTH: 22
<212> TYPE: RNA
<213> ORGANISM: Artificial
<220> FEATURE:
<223> OTHER INFORMATION: Anti-microRNA molecule

<400> SEQUENCE: 307
cacaaguucg gaucuacggg uu                                              22

<210> SEQ ID NO 308
<211> LENGTH: 22
<212> TYPE: RNA
<213> ORGANISM: Artificial
<220> FEATURE:
<223> OTHER INFORMATION: Anti-microRNA molecule

<400> SEQUENCE: 308
cauagcccug uacaaugcug cu                                              22

<210> SEQ ID NO 309
<211> LENGTH: 22
<212> TYPE: RNA
<213> ORGANISM: Artificial
<220> FEATURE:
```

<223> OTHER INFORMATION: anti-microRNA molecule

<400> SEQUENCE: 309
ccacaggagu cugagcauuu ga                                           22

<210> SEQ ID NO 310
<211> LENGTH: 22
<212> TYPE: RNA
<213> ORGANISM: Artificial
<220> FEATURE:
<223> OTHER INFORMATION: anti-microRNA molecule

<400> SEQUENCE: 310
uaccugcacu guaagcacuu uu                                           22

<210> SEQ ID NO 311
<211> LENGTH: 22
<212> TYPE: RNA
<213> ORGANISM: Artificial
<220> FEATURE:
<223> OTHER INFORMATION: anti-microRNA molecule

<400> SEQUENCE: 311
uaucugcacu gucagcacuu ua                                           22

<210> SEQ ID NO 312
<211> LENGTH: 22
<212> TYPE: RNA
<213> ORGANISM: Artificial
<220> FEATURE:
<223> OTHER INFORMATION: anti-microRNA molecule

<400> SEQUENCE: 312
gauagcccug uacaaugcug cu                                           22

<210> SEQ ID NO 313
<211> LENGTH: 22
<212> TYPE: RNA
<213> ORGANISM: Artificial
<220> FEATURE:
<223> OTHER INFORMATION: anti-microRNA molecule

<400> SEQUENCE: 313
acaaauucgg uucuacaggg ua                                           22

<210> SEQ ID NO 314
<211> LENGTH: 22
<212> TYPE: RNA
<213> ORGANISM: Artificial
<220> FEATURE:
<223> OTHER INFORMATION: anti-microRNA molecule

<400> SEQUENCE: 314
gaaagagacc gguucacugu ga                                           22

<210> SEQ ID NO 315
<211> LENGTH: 22
<212> TYPE: RNA
<213> ORGANISM: Artificial
<220> FEATURE:
<223> OTHER INFORMATION: anti-microRNA molecule

<400> SEQUENCE: 315
augcccuuuc aucauugcac ug                                           22

```
<210> SEQ ID NO 316
<211> LENGTH: 22
<212> TYPE: RNA
<213> ORGANISM: Artificial
<220> FEATURE:
<223> OTHER INFORMATION: anti-microRNA molecule

<400> SEQUENCE: 316
uccgugguuc uacccugugg ua                                              22

<210> SEQ ID NO 317
<211> LENGTH: 22
<212> TYPE: RNA
<213> ORGANISM: Artificial
<220> FEATURE:
<223> OTHER INFORMATION: anti-microRNA molecule

<400> SEQUENCE: 317
guagugcuuu cuacuuuaug gg                                              22

<210> SEQ ID NO 318
<211> LENGTH: 22
<212> TYPE: RNA
<213> ORGANISM: Artificial
<220> FEATURE:
<223> OTHER INFORMATION: anti-microRNA molecule

<400> SEQUENCE: 318
uacuagacug ugagcuccuc ga                                              22

<210> SEQ ID NO 319
<211> LENGTH: 22
<212> TYPE: RNA
<213> ORGANISM: Artificial
<220> FEATURE:
<223> OTHER INFORMATION: anti-microRNA molecule

<400> SEQUENCE: 319
ccccuaucac gauuagcauu aa                                              22

<210> SEQ ID NO 320
<211> LENGTH: 22
<212> TYPE: RNA
<213> ORGANISM: Artificial
<220> FEATURE:
<223> OTHER INFORMATION: anti-microRNA molecule

<400> SEQUENCE: 320
cucaccgaca gcguugaaug uu                                              22

<210> SEQ ID NO 321
<211> LENGTH: 22
<212> TYPE: RNA
<213> ORGANISM: Artificial
<220> FEATURE:
<223> OTHER INFORMATION: anti-microRNA molecule

<400> SEQUENCE: 321
cccaccgaca gcaaugaaug uu                                              22

<210> SEQ ID NO 322
<211> LENGTH: 22
<212> TYPE: RNA
<213> ORGANISM: Artificial
<220> FEATURE:
<223> OTHER INFORMATION: anti-microRNA molecule
```

```
<400> SEQUENCE: 322
acucaccgac agguugaaug uu                                              22

<210> SEQ ID NO 323
<211> LENGTH: 22
<212> TYPE: RNA
<213> ORGANISM: Artificial
<220> FEATURE:
<223> OTHER INFORMATION: anti-microRNA molecule

<400> SEQUENCE: 323
ugugaguucu accauugcca aa                                              22

<210> SEQ ID NO 324
<211> LENGTH: 22
<212> TYPE: RNA
<213> ORGANISM: Artificial
<220> FEATURE:
<223> OTHER INFORMATION: anti-microRNA molecule

<400> SEQUENCE: 324
agugaauucu accagugcca ua                                              22

<210> SEQ ID NO 325
<211> LENGTH: 22
<212> TYPE: RNA
<213> ORGANISM: Artificial
<220> FEATURE:
<223> OTHER INFORMATION: anti-microRNA molecule

<400> SEQUENCE: 325
acccuuauca guucuccguc ca                                              22

<210> SEQ ID NO 326
<211> LENGTH: 22
<212> TYPE: RNA
<213> ORGANISM: Artificial
<220> FEATURE:
<223> OTHER INFORMATION: anti-microRNA molecule

<400> SEQUENCE: 326
ucaggaacug ccuuucucuc ca                                              22

<210> SEQ ID NO 327
<211> LENGTH: 22
<212> TYPE: RNA
<213> ORGANISM: Artificial
<220> FEATURE:
<223> OTHER INFORMATION: anti-microRNA molecule

<400> SEQUENCE: 327
agcccaaaag gagaaucuu ug                                               22

<210> SEQ ID NO 328
<211> LENGTH: 22
<212> TYPE: RNA
<213> ORGANISM: Artificial
<220> FEATURE:
<223> OTHER INFORMATION: anti-microRNA molecule

<400> SEQUENCE: 328
ccggcugcaa cacaagacac ga                                              22

<210> SEQ ID NO 329
<211> LENGTH: 22
```

```
<212> TYPE: RNA
<213> ORGANISM: Artificial
<220> FEATURE:
<223> OTHER INFORMATION: anti-microRNA molecule

<400> SEQUENCE: 329
cugcaaaccc ugcauguggg ag                                              22

<210> SEQ ID NO 330
<211> LENGTH: 22
<212> TYPE: RNA
<213> ORGANISM: Artificial
<220> FEATURE:
<223> OTHER INFORMATION: anti-microRNA molecule

<400> SEQUENCE: 330
acccuccacc augcaaggga ug                                              22

<210> SEQ ID NO 331
<211> LENGTH: 22
<212> TYPE: RNA
<213> ORGANISM: Artificial
<220> FEATURE:
<223> OTHER INFORMATION: anti-microRNA molecule

<400> SEQUENCE: 331
cugauaucag cucaguaggc ac                                              22

<210> SEQ ID NO 332
<211> LENGTH: 22
<212> TYPE: RNA
<213> ORGANISM: Artificial
<220> FEATURE:
<223> OTHER INFORMATION: anti-microRNA molecule

<400> SEQUENCE: 332
accuaauaua ucaaacauau ca                                              22

<210> SEQ ID NO 333
<211> LENGTH: 22
<212> TYPE: RNA
<213> ORGANISM: Artificial
<220> FEATURE:
<223> OTHER INFORMATION: anti-microRNA molecule

<400> SEQUENCE: 333
agcugcuuuu gggauuccgu ug                                              22

<210> SEQ ID NO 334
<211> LENGTH: 22
<212> TYPE: RNA
<213> ORGANISM: Artificial
<220> FEATURE:
<223> OTHER INFORMATION: anti-microRNA molecule

<400> SEQUENCE: 334
uggcugucaa uucauagguc ag                                              22

<210> SEQ ID NO 335
<211> LENGTH: 22
<212> TYPE: RNA
<213> ORGANISM: Artificial
<220> FEATURE:
<223> OTHER INFORMATION: anti-microRNA molecule

<400> SEQUENCE: 335
```

-continued acugggacuu uguaggccag uu                    22

<210> SEQ ID NO 336
<211> LENGTH: 22
<212> TYPE: RNA
<213> ORGANISM: Artificial
<220> FEATURE:
<223> OTHER INFORMATION: anti-microRNA molecule

<400> SEQUENCE: 336
ucaucuugcc cgcaaagacc ca                    22

<210> SEQ ID NO 337
<211> LENGTH: 22
<212> TYPE: RNA
<213> ORGANISM: Artificial
<220> FEATURE:
<223> OTHER INFORMATION: anti-microRNA molecule

<400> SEQUENCE: 337
uccacaugga guugcuguua ca                    22

<210> SEQ ID NO 338
<211> LENGTH: 22
<212> TYPE: RNA
<213> ORGANISM: Artificial
<220> FEATURE:
<223> OTHER INFORMATION: anti-microRNA molecule

<400> SEQUENCE: 338
ugccaauauu ucugugcugc ua                    22

<210> SEQ ID NO 339
<211> LENGTH: 22
<212> TYPE: RNA
<213> ORGANISM: Artificial
<220> FEATURE:
<223> OTHER INFORMATION: anti-microRNA molecule

<400> SEQUENCE: 339
cccaacaaca ugaaacuacc ua                    22

<210> SEQ ID NO 340
<211> LENGTH: 22
<212> TYPE: RNA
<213> ORGANISM: Artificial
<220> FEATURE:
<223> OTHER INFORMATION: anti-microRNA molecule

<400> SEQUENCE: 340
gcugggugga gaagguggug aa                    22

<210> SEQ ID NO 341
<211> LENGTH: 22
<212> TYPE: RNA
<213> ORGANISM: Artificial
<220> FEATURE:
<223> OTHER INFORMATION: anti-microRNA molecule

<400> SEQUENCE: 341
gaaccuaucu ccccucugga cc                    22

<210> SEQ ID NO 342
<211> LENGTH: 22
<212> TYPE: RNA
<213> ORGANISM: Artificial

```
<220> FEATURE:
<223> OTHER INFORMATION: anti-microRNA molecule

<400> SEQUENCE: 342
uaaccaaugu gcagacuacu gu                                              22

<210> SEQ ID NO 343
<211> LENGTH: 22
<212> TYPE: RNA
<213> ORGANISM: Artificial
<220> FEATURE:
<223> OTHER INFORMATION: anti-microRNA molecule

<400> SEQUENCE: 343
aacagguagu cugaacacug gg                                              22

<210> SEQ ID NO 344
<211> LENGTH: 22
<212> TYPE: RNA
<213> ORGANISM: Artificial
<220> FEATURE:
<223> OTHER INFORMATION: anti-microRNA molecule

<400> SEQUENCE: 344
aacagauagu cuaaacacug gg                                              22

<210> SEQ ID NO 345
<211> LENGTH: 22
<212> TYPE: RNA
<213> ORGANISM: Artificial
<220> FEATURE:
<223> OTHER INFORMATION: anti-microRNA molecule

<400> SEQUENCE: 345
acaucguuac cagacagugu ua                                              22

<210> SEQ ID NO 346
<211> LENGTH: 22
<212> TYPE: RNA
<213> ORGANISM: Artificial
<220> FEATURE:
<223> OTHER INFORMATION: anti-microRNA molecule

<400> SEQUENCE: 346
ucauuaccag gcaguauuag ag                                              22

<210> SEQ ID NO 347
<211> LENGTH: 22
<212> TYPE: RNA
<213> ORGANISM: Artificial
<220> FEATURE:
<223> OTHER INFORMATION: anti-microRNA molecule

<400> SEQUENCE: 347
uccaucauua cccggcagua uu                                              22

<210> SEQ ID NO 348
<211> LENGTH: 22
<212> TYPE: RNA
<213> ORGANISM: Artificial
<220> FEATURE:
<223> OTHER INFORMATION: anti-microRNA molecule

<400> SEQUENCE: 348
cuaguggucc uaaacauuuc ac                                              22
```

<210> SEQ ID NO 349
<211> LENGTH: 22
<212> TYPE: RNA
<213> ORGANISM: Artificial
<220> FEATURE:
<223> OTHER INFORMATION: anti-microRNA molecule

<400> SEQUENCE: 349
aggcauagga ugacaaaggg aa                                              22

<210> SEQ ID NO 350
<211> LENGTH: 22
<212> TYPE: RNA
<213> ORGANISM: Artificial
<220> FEATURE:
<223> OTHER INFORMATION: anti-microRNA molecule

<400> SEQUENCE: 350
cagacuccgg uggaaugaag ga                                              22

<210> SEQ ID NO 351
<211> LENGTH: 22
<212> TYPE: RNA
<213> ORGANISM: Artificial
<220> FEATURE:
<223> OTHER INFORMATION: anti-microRNA molecule

<400> SEQUENCE: 351
ccacacacuu ccuuacauuc ca                                              22

<210> SEQ ID NO 352
<211> LENGTH: 22
<212> TYPE: RNA
<213> ORGANISM: Artificial
<220> FEATURE:
<223> OTHER INFORMATION: anti-microRNA molecule

<400> SEQUENCE: 352
acaagcuuuu ugcucgucuu au                                              22

<210> SEQ ID NO 353
<211> LENGTH: 22
<212> TYPE: RNA
<213> ORGANISM: Artificial
<220> FEATURE:
<223> OTHER INFORMATION: anti-microRNA molecule

<400> SEQUENCE: 353
ucagccgcug ucacacgcac ag                                              22

<210> SEQ ID NO 354
<211> LENGTH: 22
<212> TYPE: RNA
<213> ORGANISM: Artificial
<220> FEATURE:
<223> OTHER INFORMATION: anti-microRNA molecule

<400> SEQUENCE: 354
aggcgaagga ugacaaaggg aa                                              22

<210> SEQ ID NO 355
<211> LENGTH: 22
<212> TYPE: RNA
<213> ORGANISM: Artificial
<220> FEATURE:
<223> OTHER INFORMATION: anti-microRNA molecule

```
<400> SEQUENCE: 355
uggccgugac uggagacugu ua                                          22

<210> SEQ ID NO 356
<211> LENGTH: 22
<212> TYPE: RNA
<213> ORGANISM: Artificial
<220> FEATURE:
<223> OTHER INFORMATION: anti-microRNA molecule

<400> SEQUENCE: 356
gguacaauca acggucgaug gu                                          22

<210> SEQ ID NO 357
<211> LENGTH: 22
<212> TYPE: RNA
<213> ORGANISM: Artificial
<220> FEATURE:
<223> OTHER INFORMATION: anti-microRNA molecule

<400> SEQUENCE: 357
acugccuguc ugugccugcu gu                                          22

<210> SEQ ID NO 358
<211> LENGTH: 22
<212> TYPE: RNA
<213> ORGANISM: Artificial
<220> FEATURE:
<223> OTHER INFORMATION: anti-microRNA molecule

<400> SEQUENCE: 358
ugucugucaa uucauagguc au                                          22

<210> SEQ ID NO 359
<211> LENGTH: 22
<212> TYPE: RNA
<213> ORGANISM: Artificial
<220> FEATURE:
<223> OTHER INFORMATION: anti-microRNA molecule

<400> SEQUENCE: 359
ucacaguugc cagcugagau ua                                          22

<210> SEQ ID NO 360
<211> LENGTH: 22
<212> TYPE: RNA
<213> ORGANISM: Artificial
<220> FEATURE:
<223> OTHER INFORMATION: anti-microRNA molecule

<400> SEQUENCE: 360
ccaaucaguu ccugaugcag ua                                          22

<210> SEQ ID NO 361
<211> LENGTH: 22
<212> TYPE: RNA
<213> ORGANISM: Artificial
<220> FEATURE:
<223> OTHER INFORMATION: anti-microRNA molecule

<400> SEQUENCE: 361
cacaugguua gaucaagcac aa                                          22

<210> SEQ ID NO 362
```

-continued

```
<211> LENGTH: 22
<212> TYPE: RNA
<213> ORGANISM: Artificial
<220> FEATURE:
<223> OTHER INFORMATION: anti-microRNA molecule

<400> SEQUENCE: 362
aagaauugcg uuuggacaau ca                                              22

<210> SEQ ID NO 363
<211> LENGTH: 22
<212> TYPE: RNA
<213> ORGANISM: Artificial
<220> FEATURE:
<223> OTHER INFORMATION: anti-microRNA molecule

<400> SEQUENCE: 363
caaaguguca gauacggugu gg                                              22

<210> SEQ ID NO 364
<211> LENGTH: 22
<212> TYPE: RNA
<213> ORGANISM: Artificial
<220> FEATURE:
<223> OTHER INFORMATION: anti-microRNA molecule

<400> SEQUENCE: 364
aaacccagca gacaauguag cu                                              22

<210> SEQ ID NO 365
<211> LENGTH: 22
<212> TYPE: RNA
<213> ORGANISM: Artificial
<220> FEATURE:
<223> OTHER INFORMATION: anti-microRNA molecule

<400> SEQUENCE: 365
gacccaguag ccagauguag cu                                              22

<210> SEQ ID NO 366
<211> LENGTH: 22
<212> TYPE: RNA
<213> ORGANISM: Artificial
<220> FEATURE:
<223> OTHER INFORMATION: anti-microRNA molecule

<400> SEQUENCE: 366
ugggguauuu gacaaacuga ca                                              22

<210> SEQ ID NO 367
<211> LENGTH: 22
<212> TYPE: RNA
<213> ORGANISM: Artificial
<220> FEATURE:
<223> OTHER INFORMATION: anti-microRNA molecule

<400> SEQUENCE: 367
aaacggaacc acuagugacu ug                                              22

<210> SEQ ID NO 368
<211> LENGTH: 22
<212> TYPE: RNA
<213> ORGANISM: Artificial
<220> FEATURE:
<223> OTHER INFORMATION: anti-microRNA molecule

<400> SEQUENCE: 368
```

```
cucaauagac ugugagcucc uu                                              22

<210> SEQ ID NO 369
<211> LENGTH: 22
<212> TYPE: RNA
<213> ORGANISM: Artificial
<220> FEATURE:
<223> OTHER INFORMATION: anti-microRNA molecule

<400> SEQUENCE: 369
gaaagugccc ccacaguuug ag                                              22

<210> SEQ ID NO 370
<211> LENGTH: 22
<212> TYPE: RNA
<213> ORGANISM: Artificial
<220> FEATURE:
<223> OTHER INFORMATION: anti-microRNA molecule

<400> SEQUENCE: 370
aacaggauug agggggggcc cu                                              22

<210> SEQ ID NO 371
<211> LENGTH: 22
<212> TYPE: RNA
<213> ORGANISM: Artificial
<220> FEATURE:
<223> OTHER INFORMATION: anti-microRNA molecule

<400> SEQUENCE: 371
auguaugugg gacgguaaac ca                                              22

<210> SEQ ID NO 372
<211> LENGTH: 22
<212> TYPE: RNA
<213> ORGANISM: Artificial
<220> FEATURE:
<223> OTHER INFORMATION: anti-microRNA molecule

<400> SEQUENCE: 372
cuuugacaau acuauugcac ug                                              22

<210> SEQ ID NO 373
<211> LENGTH: 22
<212> TYPE: RNA
<213> ORGANISM: Artificial
<220> FEATURE:
<223> OTHER INFORMATION: anti-microRNA molecule

<400> SEQUENCE: 373
caccaaaaca uggaagcacu ua                                              22

<210> SEQ ID NO 374
<211> LENGTH: 22
<212> TYPE: RNA
<213> ORGANISM: Artificial
<220> FEATURE:
<223> OTHER INFORMATION: anti-microRNA molecule

<400> SEQUENCE: 374
cuuccaguca aggauguuua ca                                              22

<210> SEQ ID NO 375
<211> LENGTH: 22
<212> TYPE: RNA
```

-continued

```
<213> ORGANISM: Artificial
<220> FEATURE:
<223> OTHER INFORMATION: anti-microRNA molecule

<400> SEQUENCE: 375
ucgcccucuc aacccagcuu uu                                        22

<210> SEQ ID NO 376
<211> LENGTH: 22
<212> TYPE: RNA
<213> ORGANISM: Artificial
<220> FEATURE:
<223> OTHER INFORMATION: anti-microRNA molecule

<400> SEQUENCE: 376
cgaacccaca aucccuggcu ua                                        22

<210> SEQ ID NO 377
<211> LENGTH: 22
<212> TYPE: RNA
<213> ORGANISM: Artificial
<220> FEATURE:
<223> OTHER INFORMATION: anti-microRNA molecule

<400> SEQUENCE: 377
gauacagcag caauucaugu uu                                        22

<210> SEQ ID NO 378
<211> LENGTH: 22
<212> TYPE: RNA
<213> ORGANISM: Artificial
<220> FEATURE:
<223> OTHER INFORMATION: anti-microRNA molecule

<400> SEQUENCE: 378
agaggucgac cguguaaugu gc                                        22

<210> SEQ ID NO 379
<211> LENGTH: 22
<212> TYPE: RNA
<213> ORGANISM: Artificial
<220> FEATURE:
<223> OTHER INFORMATION: anti-microRNA molecule

<400> SEQUENCE: 379
ccagcagcac cuggggcagu gg                                        22

<210> SEQ ID NO 380
<211> LENGTH: 22
<212> TYPE: RNA
<213> ORGANISM: Artificial
<220> FEATURE:
<223> OTHER INFORMATION: anti-microRNA molecule

<400> SEQUENCE: 380
caccaaugcc cuaggggaug cg                                        22

<210> SEQ ID NO 381
<211> LENGTH: 22
<212> TYPE: RNA
<213> ORGANISM: Artificial
<220> FEATURE:
<223> OTHER INFORMATION: anti-microRNA molecule

<400> SEQUENCE: 381
ggcuggagga agggcccaga gg                                        22
```

```
<210> SEQ ID NO 382
<211> LENGTH: 22
<212> TYPE: RNA
<213> ORGANISM: Artificial
<220> FEATURE:
<223> OTHER INFORMATION: anti-microRNA molecule

<400> SEQUENCE: 382
acggaagggc agagagggcc ag                                              22

<210> SEQ ID NO 383
<211> LENGTH: 22
<212> TYPE: RNA
<213> ORGANISM: Artificial
<220> FEATURE:
<223> OTHER INFORMATION: anti-microRNA molecule

<400> SEQUENCE: 383
aaaaagguua gcugggugug uu                                              22

<210> SEQ ID NO 384
<211> LENGTH: 22
<212> TYPE: RNA
<213> ORGANISM: Artificial
<220> FEATURE:
<223> OTHER INFORMATION: anti-microRNA molecule

<400> SEQUENCE: 384
acaaccagcu aagacacugc ca                                              22

<210> SEQ ID NO 385
<211> LENGTH: 22
<212> TYPE: RNA
<213> ORGANISM: Artificial
<220> FEATURE:
<223> OTHER INFORMATION: anti-microRNA molecule

<400> SEQUENCE: 385
caaucagcua augacacugc cu                                              22

<210> SEQ ID NO 386
<211> LENGTH: 22
<212> TYPE: RNA
<213> ORGANISM: Artificial
<220> FEATURE:
<223> OTHER INFORMATION: anti-microRNA molecule

<400> SEQUENCE: 386
caaucagcua acuacacugc cu                                              22

<210> SEQ ID NO 387
<211> LENGTH: 22
<212> TYPE: RNA
<213> ORGANISM: Artificial
<220> FEATURE:
<223> OTHER INFORMATION: anti-microRNA molecule

<400> SEQUENCE: 387
acaggccggg acaagugcaa ua                                              22

<210> SEQ ID NO 388
<211> LENGTH: 22
<212> TYPE: RNA
<213> ORGANISM: Artificial
<220> FEATURE:
```

```
<223> OTHER INFORMATION: anti-microRNA molecule

<400> SEQUENCE: 388
cuaccugcac gaacagcacu uu                                              22

<210> SEQ ID NO 389
<211> LENGTH: 22
<212> TYPE: RNA
<213> ORGANISM: Artificial
<220> FEATURE:
<223> OTHER INFORMATION: anti-microRNA molecule

<400> SEQUENCE: 389
ugcucaauaa auacccguug aa                                              22

<210> SEQ ID NO 390
<211> LENGTH: 22
<212> TYPE: RNA
<213> ORGANISM: Artificial
<220> FEATURE:
<223> OTHER INFORMATION: anti-microRNA molecule

<400> SEQUENCE: 390
gcaaaaaugu gcuagugcca aa                                              22

<210> SEQ ID NO 391
<211> LENGTH: 22
<212> TYPE: RNA
<213> ORGANISM: Artificial
<220> FEATURE:
<223> OTHER INFORMATION: anti-microRNA molecule

<400> SEQUENCE: 391
aacaauacaa cuuacuaccu ca                                              22

<210> SEQ ID NO 392
<211> LENGTH: 22
<212> TYPE: RNA
<213> ORGANISM: Artificial
<220> FEATURE:
<223> OTHER INFORMATION: anti-microRNA molecule

<400> SEQUENCE: 392
uaccugcacu guuagcacuu ug                                              22

<210> SEQ ID NO 393
<211> LENGTH: 22
<212> TYPE: RNA
<213> ORGANISM: Artificial
<220> FEATURE:
<223> OTHER INFORMATION: anti-microRNA molecule

<400> SEQUENCE: 393
acacaaauuc gguucuacag gg                                              22

<210> SEQ ID NO 394
<211> LENGTH: 22
<212> TYPE: RNA
<213> ORGANISM: Artificial
<220> FEATURE:
<223> OTHER INFORMATION: anti-microRNA molecule

<400> SEQUENCE: 394
cacauaggaa ugaaaagcca ua                                              22
```

```
<210> SEQ ID NO 395
<211> LENGTH: 22
<212> TYPE: RNA
<213> ORGANISM: Artificial
<220> FEATURE:
<223> OTHER INFORMATION: anti-microRNA molecule

<400> SEQUENCE: 395
acaaaguucu gugaugcacu ga                                          22

<210> SEQ ID NO 396
<211> LENGTH: 22
<212> TYPE: RNA
<213> ORGANISM: Artificial
<220> FEATURE:
<223> OTHER INFORMATION: anti-microRNA molecule

<400> SEQUENCE: 396
uccucaagga gccucagucu ag                                          22

<210> SEQ ID NO 397
<211> LENGTH: 22
<212> TYPE: RNA
<213> ORGANISM: Artificial
<220> FEATURE:
<223> OTHER INFORMATION: anti-microRNA molecule

<400> SEQUENCE: 397
ccccuaucac aauuagcauu aa                                          22

<210> SEQ ID NO 398
<211> LENGTH: 22
<212> TYPE: RNA
<213> ORGANISM: Artificial
<220> FEATURE:
<223> OTHER INFORMATION: anti-microRNA molecule

<400> SEQUENCE: 398
aacagguagu cuaaacacug gg                                          22

<210> SEQ ID NO 399
<211> LENGTH: 22
<212> TYPE: RNA
<213> ORGANISM: Artificial
<220> FEATURE:
<223> OTHER INFORMATION: anti-microRNA molecule

<400> SEQUENCE: 399
ucaucauuac caggcaguau ua                                          22

<210> SEQ ID NO 400
<211> LENGTH: 22
<212> TYPE: RNA
<213> ORGANISM: Artificial
<220> FEATURE:
<223> OTHER INFORMATION: anti-microRNA molecule

<400> SEQUENCE: 400
ucuagugguc cuaaacauuu ca                                          22

<210> SEQ ID NO 401
<211> LENGTH: 22
<212> TYPE: RNA
<213> ORGANISM: Artificial
<220> FEATURE:
<223> OTHER INFORMATION: anti-microRNA molecule
```

```
<400> SEQUENCE: 401
aggcaaagga ugacaaaggg aa                                          22

<210> SEQ ID NO 402
<211> LENGTH: 22
<212> TYPE: RNA
<213> ORGANISM: Artificial
<220> FEATURE:
<223> OTHER INFORMATION: anti-microRNA molecule

<400> SEQUENCE: 402
ccagucaguu ccugaugcag ua                                          22

<210> SEQ ID NO 403
<211> LENGTH: 22
<212> TYPE: RNA
<213> ORGANISM: Artificial
<220> FEATURE:
<223> OTHER INFORMATION: anti-microRNA molecule

<400> SEQUENCE: 403
aaacggaacc acuagugacu ua                                          22

<210> SEQ ID NO 404
<211> LENGTH: 22
<212> TYPE: RNA
<213> ORGANISM: Artificial
<220> FEATURE:
<223> OTHER INFORMATION: anti-microRNA molecule

<400> SEQUENCE: 404
uccagcagcu cacaaucuag ug                                          22

<210> SEQ ID NO 405
<211> LENGTH: 22
<212> TYPE: RNA
<213> ORGANISM: Artificial
<220> FEATURE:
<223> OTHER INFORMATION: anti-microRNA molecule

<400> SEQUENCE: 405
aaaagugccc ccauaguuug ag                                          22

<210> SEQ ID NO 406
<211> LENGTH: 22
<212> TYPE: RNA
<213> ORGANISM: Artificial
<220> FEATURE:
<223> OTHER INFORMATION: anti-microRNA molecule

<400> SEQUENCE: 406
gcacacaaag uggaagcacu uu                                          22

<210> SEQ ID NO 407
<211> LENGTH: 22
<212> TYPE: RNA
<213> ORGANISM: Artificial
<220> FEATURE:
<223> OTHER INFORMATION: anti-microRNA molecule

<400> SEQUENCE: 407
agagagggcc uccacuuuga ug                                          22

<210> SEQ ID NO 408
<211> LENGTH: 22
```

-continued

```
<212> TYPE: RNA
<213> ORGANISM: Artificial
<220> FEATURE:
<223> OTHER INFORMATION: anti-microRNA molecule

<400> SEQUENCE: 408
cacucaaaac cuggcggcac uu                                              22

<210> SEQ ID NO 409
<211> LENGTH: 22
<212> TYPE: RNA
<213> ORGANISM: Artificial
<220> FEATURE:
<223> OTHER INFORMATION: anti-microRNA molecule

<400> SEQUENCE: 409
caaaagagcc cccaguuuga gu                                              22

<210> SEQ ID NO 410
<211> LENGTH: 22
<212> TYPE: RNA
<213> ORGANISM: Artificial
<220> FEATURE:
<223> OTHER INFORMATION: anti-microRNA molecule

<400> SEQUENCE: 410
acacuacaaa cucugcggca cu                                              22

<210> SEQ ID NO 411
<211> LENGTH: 22
<212> TYPE: RNA
<213> ORGANISM: Artificial
<220> FEATURE:
<223> OTHER INFORMATION: anti-microRNA molecule

<400> SEQUENCE: 411
acacacaaaa gggaagcacu uu                                              22

<210> SEQ ID NO 412
<211> LENGTH: 22
<212> TYPE: RNA
<213> ORGANISM: Artificial
<220> FEATURE:
<223> OTHER INFORMATION: anti-microRNA molecule

<400> SEQUENCE: 412
gacucaaaag uaguagcacu uu                                              22

<210> SEQ ID NO 413
<211> LENGTH: 22
<212> TYPE: RNA
<213> ORGANISM: Artificial
<220> FEATURE:
<223> OTHER INFORMATION: anti-microRNA molecule

<400> SEQUENCE: 413
acaugcacau gcacacauac au                                              22

<210> SEQ ID NO 414
<211> LENGTH: 22
<212> TYPE: RNA
<213> ORGANISM: Artificial
<220> FEATURE:
<223> OTHER INFORMATION: anti-microRNA molecule

<400> SEQUENCE: 414
```

| ggaagaacag cccuccucug cc | 22 |

<210> SEQ ID NO 415
<211> LENGTH: 22
<212> TYPE: RNA
<213> ORGANISM: Artificial
<220> FEATURE:
<223> OTHER INFORMATION: anti-microRNA molecule

<400> SEQUENCE: 415

| gaagagagcu ugcccuugca ua | 22 |

<210> SEQ ID NO 416
<211> LENGTH: 22
<212> TYPE: RNA
<213> ORGANISM: Artificial
<220> FEATURE:
<223> OTHER INFORMATION: anti-microRNA molecule

<400> SEQUENCE: 416

| cagcuaugcc agcaucuugc cu | 22 |

<210> SEQ ID NO 417
<211> LENGTH: 22
<212> TYPE: RNA
<213> ORGANISM: Artificial
<220> FEATURE:
<223> OTHER INFORMATION: anti-microRNA molecule

<400> SEQUENCE: 417

| gguguugcag cgcuucaugu uu | 22 |

<210> SEQ ID NO 418
<211> LENGTH: 22
<212> TYPE: RNA
<213> ORGANISM: Artificial
<220> FEATURE:
<223> OTHER INFORMATION: anti-microRNA molecule

<400> SEQUENCE: 418

| cacuuacuga gcaccuacua gg | 22 |

<210> SEQ ID NO 419
<211> LENGTH: 22
<212> TYPE: RNA
<213> ORGANISM: Artificial
<220> FEATURE:
<223> OTHER INFORMATION: anti-microRNA molecule

<400> SEQUENCE: 419

| gacuggagga agggcccaga gg | 22 |

<210> SEQ ID NO 420
<211> LENGTH: 22
<212> TYPE: RNA
<213> ORGANISM: Artificial
<220> FEATURE:
<223> OTHER INFORMATION: anti-microRNA molecule

<400> SEQUENCE: 420

| cucugcaggc ccugugcuuu gc | 22 |

<210> SEQ ID NO 421
<211> LENGTH: 22
<212> TYPE: RNA
<213> ORGANISM: Artificial

```
<220> FEATURE:
<223> OTHER INFORMATION: anti-microRNA molecule

<400> SEQUENCE: 421
guucuaggau aggcccaggg gc                                              22

<210> SEQ ID NO 422
<211> LENGTH: 22
<212> TYPE: RNA
<213> ORGANISM: Artificial
<220> FEATURE:
<223> OTHER INFORMATION: anti-microRNA molecule

<400> SEQUENCE: 422
aaggcaucau auaggagcug aa                                              22

<210> SEQ ID NO 423
<211> LENGTH: 22
<212> TYPE: RNA
<213> ORGANISM: Artificial
<220> FEATURE:
<223> OTHER INFORMATION: anti-microRNA molecule

<400> SEQUENCE: 423
caacaaaauc acugaugcug ga                                              22

<210> SEQ ID NO 424
<211> LENGTH: 22
<212> TYPE: RNA
<213> ORGANISM: Artificial
<220> FEATURE:
<223> OTHER INFORMATION: anti-microRNA molecule

<400> SEQUENCE: 424
gugagcuccu ggaggacagg ga                                              22

<210> SEQ ID NO 425
<211> LENGTH: 22
<212> TYPE: RNA
<213> ORGANISM: Artificial
<220> FEATURE:
<223> OTHER INFORMATION: anti-microRNA molecule

<400> SEQUENCE: 425
gcuauaaagu aacugagacg ga                                              22

<210> SEQ ID NO 426
<211> LENGTH: 22
<212> TYPE: RNA
<213> ORGANISM: Artificial
<220> FEATURE:
<223> OTHER INFORMATION: anti-microRNA molecule

<400> SEQUENCE: 426
gacugaccga ccgaccgauc ga                                              22

<210> SEQ ID NO 427
<211> LENGTH: 22
<212> TYPE: RNA
<213> ORGANISM: Artificial
<220> FEATURE:
<223> OTHER INFORMATION: anti-microRNA molecule

<400> SEQUENCE: 427
cgggugcgau uucuguguga ga                                              22
```

<210> SEQ ID NO 428
<211> LENGTH: 22
<212> TYPE: RNA
<213> ORGANISM: Artificial
<220> FEATURE:
<223> OTHER INFORMATION: anti-microRNA molecule

<400> SEQUENCE: 428
cagucaggcu uggcuagauc ca                                              22

<210> SEQ ID NO 429
<211> LENGTH: 22
<212> TYPE: RNA
<213> ORGANISM: Artificial
<220> FEATURE:
<223> OTHER INFORMATION: anti-microRNA molecule

<400> SEQUENCE: 429
agcacuggac uaggggucag ca                                              22

<210> SEQ ID NO 430
<211> LENGTH: 22
<212> TYPE: RNA
<213> ORGANISM: Artificial
<220> FEATURE:
<223> OTHER INFORMATION: anti-microRNA molecule

<400> SEQUENCE: 430
gaggcaggca cucgggcaga ca                                              22

<210> SEQ ID NO 431
<211> LENGTH: 22
<212> TYPE: RNA
<213> ORGANISM: Artificial
<220> FEATURE:
<223> OTHER INFORMATION: anti-microRNA molecule

<400> SEQUENCE: 431
aaucagcuaa uuacacugcc ua                                              22

<210> SEQ ID NO 432
<211> LENGTH: 22
<212> TYPE: RNA
<213> ORGANISM: Artificial
<220> FEATURE:
<223> OTHER INFORMATION: anti-microRNA molecule

<400> SEQUENCE: 432
gaaaguguau gggcuuugug aa                                              22

<210> SEQ ID NO 433
<211> LENGTH: 22
<212> TYPE: RNA
<213> ORGANISM: Artificial
<220> FEATURE:
<223> OTHER INFORMATION: anti-microRNA molecule

<400> SEQUENCE: 433
ggcucaaagg gcuccucagg ga                                              22

<210> SEQ ID NO 434
<211> LENGTH: 22
<212> TYPE: RNA
<213> ORGANISM: Artificial
<220> FEATURE:
<223> OTHER INFORMATION: anti-microRNA molecule

```
<400> SEQUENCE: 434
caacaaaauc acaagucuuc ca                                              22

<210> SEQ ID NO 435
<211> LENGTH: 22
<212> TYPE: RNA
<213> ORGANISM: Artificial
<220> FEATURE:
<223> OTHER INFORMATION: anti-microRNA molecule

<400> SEQUENCE: 435
ucaggccggg acaagugcaa ua                                              22

<210> SEQ ID NO 436
<211> LENGTH: 22
<212> TYPE: RNA
<213> ORGANISM: Artificial
<220> FEATURE:
<223> OTHER INFORMATION: anti-microRNA  molecule

<400> SEQUENCE: 436
uaccugcacg aacagcacuu ug                                              22

<210> SEQ ID NO 437
<211> LENGTH: 22
<212> TYPE: RNA
<213> ORGANISM: Artificial
<220> FEATURE:
<223> OTHER INFORMATION: anti-microRNA molecule

<400> SEQUENCE: 437
acuacccuca ugccccucaa gg                                              22

<210> SEQ ID NO 438
<211> LENGTH: 22
<212> TYPE: RNA
<213> ORGANISM: Artificial
<220> FEATURE:
<223> OTHER INFORMATION: anti-microRNA molecule

<400> SEQUENCE: 438
ccaaaaguaa cuagcacacc ac                                              22

<210> SEQ ID NO 439
<211> LENGTH: 22
<212> TYPE: RNA
<213> ORGANISM: Artificial
<220> FEATURE:
<223> OTHER INFORMATION: anti-microRNA molecule

<400> SEQUENCE: 439 cauuuucgu uauugcucuu ga                                               22

<210> SEQ ID NO 440
<211> LENGTH: 22
<212> TYPE: RNA
<213> ORGANISM: Artificial
<220> FEATURE:
<223> OTHER INFORMATION: anti-microRNA molecule

<400> SEQUENCE: 440
gagacuagau auggaagggu ga                                              22

<210> SEQ ID NO 441
```

```
<211> LENGTH: 22
<212> TYPE: RNA
<213> ORGANISM: Artificial
<220> FEATURE:
<223> OTHER INFORMATION: anti-microRNA molecule

<400> SEQUENCE: 441 auacuggggca cacggaggga ga                                              22

<210> SEQ ID NO 442
<211> LENGTH: 22
<212> TYPE: RNA
<213> ORGANISM: Artificial
<220> FEATURE:
<223> OTHER INFORMATION: anti-microRNA molecule

<400> SEQUENCE: 442
agcugggcga cccagaggga ca                                               22

<210> SEQ ID NO 443
<211> LENGTH: 22
<212> TYPE: RNA
<213> ORGANISM: Artificial
<220> FEATURE:
<223> OTHER INFORMATION: anti-microRNA molecule

<400> SEQUENCE: 443
agagguuaag acagcagggc ug                                               22

<210> SEQ ID NO 444
<211> LENGTH: 22
<212> TYPE: RNA
<213> ORGANISM: Artificial
<220> FEATURE:
<223> OTHER INFORMATION: anti-microRNA molecule

<400> SEQUENCE: 444
guacuaugca accuacuacu cu                                               22

<210> SEQ ID NO 445
<211> LENGTH: 22
<212> TYPE: RNA
<213> ORGANISM: Artificial
<220> FEATURE:
<223> OTHER INFORMATION: anti-microRNA molecule

<400> SEQUENCE: 445
guaccccugg agauucugau aa                                               22

<210> SEQ ID NO 446
<211> LENGTH: 22
<212> TYPE: RNA
<213> ORGANISM: Artificial
<220> FEATURE:
<223> OTHER INFORMATION: anti-microRNA molecule

<400> SEQUENCE: 446
ucacaccuag guuccaagga uu                                               22

<210> SEQ ID NO 447
<211> LENGTH: 22
<212> TYPE: RNA
<213> ORGANISM: Artificial
<220> FEATURE:
<223> OTHER INFORMATION: anti-microRNA molecule

<400> SEQUENCE: 447
```
uuacagaugg auaccgugca au　　　　　　　　　　　　　　　　22

<210> SEQ ID NO 448
<211> LENGTH: 22
<212> TYPE: RNA
<213> ORGANISM: Artificial
<220> FEATURE:
<223> OTHER INFORMATION: anti-microRNA molecule

<400> SEQUENCE: 448
ggaccaaucg ccguccccgc cg　　　　　　　　　　　　　　　　22

<210> SEQ ID NO 449
<211> LENGTH: 22
<212> TYPE: RNA
<213> ORGANISM: Artificial
<220> FEATURE:
<223> OTHER INFORMATION: anti-microRNA molecule

<400> SEQUENCE: 449
auaaggauuu uuaggggcau ua　　　　　　　　　　　　　　　　22

<210> SEQ ID NO 450
<211> LENGTH: 22
<212> TYPE: RNA
<213> ORGANISM: Artificial
<220> FEATURE:
<223> OTHER INFORMATION: anti-microRNA molecule

<400> SEQUENCE: 450
gguucaguug uucaaccagu ua　　　　　　　　　　　　　　　　22

<210> SEQ ID NO 451
<211> LENGTH: 22
<212> TYPE: RNA
<213> ORGANISM: Artificial
<220> FEATURE:
<223> OTHER INFORMATION: anti-microRNA molecule

<400> SEQUENCE: 451
aacuauacaa ccuacuaccu ca　　　　　　　　　　　　　　　　22

<210> SEQ ID NO 452
<211> LENGTH: 22
<212> TYPE: RNA
<213> ORGANISM: Artificial
<220> FEATURE:
<223> OTHER INFORMATION: anti-microRNA molecule

<400> SEQUENCE: 452
cucacacuug aggucucagg ga　　　　　　　　　　　　　　　　22

<210> SEQ ID NO 453
<211> LENGTH: 22
<212> TYPE: RNA
<213> ORGANISM: Artificial
<220> FEATURE:
<223> OTHER INFORMATION: anti-microRNA molecule

<400> SEQUENCE: 453
cuacauacuu cuuuacauuc ca　　　　　　　　　　　　　　　　22

<210> SEQ ID NO 454
<211> LENGTH: 22
<212> TYPE: RNA

```
<213> ORGANISM: Artificial
<220> FEATURE:
<223> OTHER INFORMATION: anti-microRNA molecule

<400> SEQUENCE: 454
cacaucaaag cuggcuguga ua                                              22

<210> SEQ ID NO 455
<211> LENGTH: 22
<212> TYPE: RNA
<213> ORGANISM: Artificial
<220> FEATURE:
<223> OTHER INFORMATION: anti-microRNA molecule

<400> SEQUENCE: 455
caaccagcua accacacugc cu                                              22

<210> SEQ ID NO 456
<211> LENGTH: 22
<212> TYPE: RNA
<213> ORGANISM: Artificial
<220> FEATURE:
<223> OTHER INFORMATION: anti-microRNA molecule

<400> SEQUENCE: 456
acugcuaguu uccacccggu ga                                              22

<210> SEQ ID NO 457
<211> LENGTH: 22
<212> TYPE: RNA
<213> ORGANISM: Artificial
<220> FEATURE:
<223> OTHER INFORMATION: anti-microRNA molecule

<400> SEQUENCE: 457
caugcgaauu uucacccggu ga                                              22

<210> SEQ ID NO 458
<211> LENGTH: 22
<212> TYPE: RNA
<213> ORGANISM: Artificial
<220> FEATURE:
<223> OTHER INFORMATION: anti-microRNA molecule

<400> SEQUENCE: 458
acugcaagug uucacccggu ga                                              22

<210> SEQ ID NO 459
<211> LENGTH: 22
<212> TYPE: RNA
<213> ORGANISM: Artificial
<220> FEATURE:
<223> OTHER INFORMATION: anti-microRNA molecule

<400> SEQUENCE: 459
acuccaguuu uucucccggu ga                                              22

<210> SEQ ID NO 460
<211> LENGTH: 22
<212> TYPE: RNA
<213> ORGANISM: Artificial
<220> FEATURE:
<223> OTHER INFORMATION: anti-microRNA molecule

<400> SEQUENCE: 460
caagcugauu uacacccggu ga                                              22
```

```
<210> SEQ ID NO 461
<211> LENGTH: 22
<212> TYPE: RNA
<213> ORGANISM: Artificial
<220> FEATURE:
<223> OTHER INFORMATION: anti-microRNA molecule

<400> SEQUENCE: 461
uuagcugaug uacacccggu ga                                          22

<210> SEQ ID NO 462
<211> LENGTH: 22
<212> TYPE: RNA
<213> ORGANISM: Artificial
<220> FEATURE:
<223> OTHER INFORMATION: anti-microRNA molecule

<400> SEQUENCE: 462
uaggugauuu uucacccggu ga                                          22

<210> SEQ ID NO 463
<211> LENGTH: 22
<212> TYPE: RNA
<213> ORGANISM: Artificial
<220> FEATURE:
<223> OTHER INFORMATION: anti-microRNA molecule

<400> SEQUENCE: 463
cucuguagau guuaacccgg ug                                          22

<210> SEQ ID NO 464
<211> LENGTH: 22
<212> TYPE: RNA
<213> ORGANISM: Artificial
<220> FEATURE:
<223> OTHER INFORMATION: anti-microRNA molecule

<400> SEQUENCE: 464
cgacagcaag uaaacuguga ua                                          22

<210> SEQ ID NO 465
<211> LENGTH: 22
<212> TYPE: RNA
<213> ORGANISM: Artificial
<220> FEATURE:
<223> OTHER INFORMATION: anti-microRNA molecule

<400> SEQUENCE: 465
aagcugaaug ugucucuagu ca                                          22

<210> SEQ ID NO 466
<211> LENGTH: 22
<212> TYPE: RNA
<213> ORGANISM: Artificial
<220> FEATURE:
<223> OTHER INFORMATION: anti-microRNA molecule

<400> SEQUENCE: 466
aagcugaaug ugucucuagu ca                                          22

<210> SEQ ID NO 467
<211> LENGTH: 22
<212> TYPE: RNA
<213> ORGANISM: Artificial
<220> FEATURE:
```

```
<223> OTHER INFORMATION: anti-microRNA molecule

<400> SEQUENCE: 467
ugaagagagc gacuccauga ca                                              22

<210> SEQ ID NO 468
<211> LENGTH: 22
<212> TYPE: RNA
<213> ORGANISM: Artificial
<220> FEATURE:
<223> OTHER INFORMATION: anti-microRNA molecule

<400> SEQUENCE: 468
ugaagagagc gccuccauga ca                                              22

<210> SEQ ID NO 469
<211> LENGTH: 22
<212> TYPE: RNA
<213> ORGANISM: Artificial
<220> FEATURE:
<223> OTHER INFORMATION: anti-microRNA molecule

<400> SEQUENCE: 469
cgcaucuacu gagccuaccu ca                                              22

<210> SEQ ID NO 470
<211> LENGTH: 22
<212> TYPE: RNA
<213> ORGANISM: Artificial
<220> FEATURE:
<223> OTHER INFORMATION: anti-microRNA molecule

<400> SEQUENCE: 470
ucugcagcuu cucguggugc uu                                              22

<210> SEQ ID NO 471
<211> LENGTH: 22
<212> TYPE: RNA
<213> ORGANISM: Artificial
<220> FEATURE:
<223> OTHER INFORMATION: anti-microRNA molecule

<400> SEQUENCE: 471
cccaagaaua ccagacauau ca                                              22

<210> SEQ ID NO 472
<211> LENGTH: 22
<212> TYPE: RNA
<213> ORGANISM: Artificial
<220> FEATURE:
<223> OTHER INFORMATION: anti-microRNA molecule

<400> SEQUENCE: 472
acauggauag gagcuacggg ua                                              22

<210> SEQ ID NO 473
<211> LENGTH: 22
<212> TYPE: RNA
<213> ORGANISM: Artificial
<220> FEATURE:
<223> OTHER INFORMATION: anti-microRNA molecule

<400> SEQUENCE: 473
cacggaaaca uauguacggg ug                                              22
```

```
<210> SEQ ID NO 474
<211> LENGTH: 22
<212> TYPE: RNA
<213> ORGANISM: Artificial
<220> FEATURE:
<223> OTHER INFORMATION: anti-microRNA molecule

<400> SEQUENCE: 474
cacggaaaca aauguacggg ug                                               22

<210> SEQ ID NO 475
<211> LENGTH: 22
<212> TYPE: RNA
<213> ORGANISM: Artificial
<220> FEATURE:
<223> OTHER INFORMATION: anti-microRNA molecule

<400> SEQUENCE: 475
cggauuauga agauuacggg ua                                               22

<210> SEQ ID NO 476
<211> LENGTH: 22
<212> TYPE: RNA
<213> ORGANISM: Artificial
<220> FEATURE:
<223> OTHER INFORMATION: anti-microRNA molecule

<400> SEQUENCE: 476
ucagcagaaa cuuauacggg ua                                               22

<210> SEQ ID NO 477
<211> LENGTH: 22
<212> TYPE: RNA
<213> ORGANISM: Artificial
<220> FEATURE:
<223> OTHER INFORMATION: anti-microRNA molecule

<400> SEQUENCE: 477
cucagcggaa acauuacggg ua                                               22

<210> SEQ ID NO 478
<211> LENGTH: 22
<212> TYPE: RNA
<213> ORGANISM: Artificial
<220> FEATURE:
<223> OTHER INFORMATION: anti-microRNA molecule

<400> SEQUENCE: 478
acacagcucg aucuacaggg ua                                               22

<210> SEQ ID NO 479
<211> LENGTH: 22
<212> TYPE: RNA
<213> ORGANISM: Artificial
<220> FEATURE:
<223> OTHER INFORMATION: anti-microRNA molecule

<400> SEQUENCE: 479
auugccguac ugaacgaucu ca                                               22

<210> SEQ ID NO 480
<211> LENGTH: 22
<212> TYPE: RNA
<213> ORGANISM: Artificial
<220> FEATURE:
<223> OTHER INFORMATION: anti-microRNA molecule
```

```
<400> SEQUENCE: 480
aucauccuga uaaacgauuc ga                                              22

<210> SEQ ID NO 481
<211> LENGTH: 22
<212> TYPE: RNA
<213> ORGANISM: Artificial
<220> FEATURE:
<223> OTHER INFORMATION: anti-microRNA molecule

<400> SEQUENCE: 481
gaacuagaaa augugcauaa ua                                              22

<210> SEQ ID NO 482
<211> LENGTH: 22
<212> TYPE: RNA
<213> ORGANISM: Artificial
<220> FEATURE:
<223> OTHER INFORMATION: anti-microRNA molecule

<400> SEQUENCE: 482
agaugaguaa cgguucuagu ca                                              22

<210> SEQ ID NO 483
<211> LENGTH: 22
<212> TYPE: RNA
<213> ORGANISM: Artificial
<220> FEATURE:
<223> OTHER INFORMATION: anti-microRNA molecule

<400> SEQUENCE: 483
cuguaagcua gauuacauau ca                                              22

<210> SEQ ID NO 484
<211> LENGTH: 22
<212> TYPE: RNA
<213> ORGANISM: Artificial
<220> FEATURE:
<223> OTHER INFORMATION: anti-microRNA molecule

<400> SEQUENCE: 484
uuccaacucg cuucaguguc au                                              22

<210> SEQ ID NO 485
<211> LENGTH: 22
<212> TYPE: RNA
<213> ORGANISM: Artificial
<220> FEATURE:
<223> OTHER INFORMATION: anti-microRNA molecule

<400> SEQUENCE: 485
ucgguaacgc uucaguguca ua                                              22

<210> SEQ ID NO 486
<211> LENGTH: 22
<212> TYPE: RNA
<213> ORGANISM: Artificial
<220> FEATURE:
<223> OTHER INFORMATION: anti-microRNA molecule

<400> SEQUENCE: 486
ucgguuacgc uucaguguca ua                                              22

<210> SEQ ID NO 487
<211> LENGTH: 22
```

```
<212> TYPE: RNA
<213> ORGANISM: Artificial
<220> FEATURE:
<223> OTHER INFORMATION: anti-microRNA molecule

<400> SEQUENCE: 487
cacaucccua aucaguguca ug                                          22

<210> SEQ ID NO 488
<211> LENGTH: 22
<212> TYPE: RNA
<213> ORGANISM: Artificial
<220> FEATURE:
<223> OTHER INFORMATION: anti-microRNA molecule

<400> SEQUENCE: 488
uacucuuucu aggagguugu ga                                          22

<210> SEQ ID NO 489
<211> LENGTH: 22
<212> TYPE: RNA
<213> ORGANISM: Artificial
<220> FEATURE:
<223> OTHER INFORMATION: anti-microRNA molecule

<400> SEQUENCE: 489
gucuacacuu uugagucuuc ga                                          22

<210> SEQ ID NO 490
<211> LENGTH: 22
<212> TYPE: RNA
<213> ORGANISM: Artificial
<220> FEATURE:
<223> OTHER INFORMATION: anti-microRNA molecule

<400> SEQUENCE: 490
uucuacacuu uuuaauuuuc ga                                          22

<210> SEQ ID NO 491
<211> LENGTH: 22
<212> TYPE: RNA
<213> ORGANISM: Artificial
<220> FEATURE:
<223> OTHER INFORMATION: anti-microRNA molecule

<400> SEQUENCE: 491
uggaaacacc aacgacguau ua                                          22

<210> SEQ ID NO 492
<211> LENGTH: 22
<212> TYPE: RNA
<213> ORGANISM: Artificial
<220> FEATURE:
<223> OTHER INFORMATION: anti-microRNA molecule

<400> SEQUENCE: 492
cguucacuac ccaugucuuu ca                                          22

<210> SEQ ID NO 493
<211> LENGTH: 22
<212> TYPE: RNA
<213> ORGANISM: Artificial
<220> FEATURE:
<223> OTHER INFORMATION: anti-microRNA molecule

<400> SEQUENCE: 493
```

-continued cagcuaugcc aacaucuugc cu                                          22

<210> SEQ ID NO 494
<211> LENGTH: 22
<212> TYPE: RNA
<213> ORGANISM: Artificial
<220> FEATURE:
<223> OTHER INFORMATION: anti-microRNA molecule

<400> SEQUENCE: 494
cugaacugcc uacaucuugc ca                                          22

<210> SEQ ID NO 495
<211> LENGTH: 22
<212> TYPE: RNA
<213> ORGANISM: Artificial
<220> FEATURE:
<223> OTHER INFORMATION: anti-microRNA molecule

<400> SEQUENCE: 495
uguagacugc cauuucuugc ca                                          22

<210> SEQ ID NO 496
<211> LENGTH: 22
<212> TYPE: RNA
<213> ORGANISM: Artificial
<220> FEATURE:
<223> OTHER INFORMATION: anti-microRNA molecule

<400> SEQUENCE: 496
ugaagccggu ugguagcuuu aa                                          22

<210> SEQ ID NO 497
<211> LENGTH: 22
<212> TYPE: RNA
<213> ORGANISM: Artificial
<220> FEATURE:
<223> OTHER INFORMATION: anti-microRNA molecule

<400> SEQUENCE: 497
ucaaggcuuc aucaacaacg aa                                          22

<210> SEQ ID NO 498
<211> LENGTH: 22
<212> TYPE: RNA
<213> ORGANISM: Artificial
<220> FEATURE:
<223> OTHER INFORMATION: anti-microRNA molecule

<400> SEQUENCE: 498
uggacagcua uggccugaug aa                                          22

<210> SEQ ID NO 499
<211> LENGTH: 22
<212> TYPE: RNA
<213> ORGANISM: Artificial
<220> FEATURE:
<223> OTHER INFORMATION: anti-microRNA molecule

<400> SEQUENCE: 499
agcacaaaca accaggccuc ca                                          22

<210> SEQ ID NO 500
<211> LENGTH: 22
<212> TYPE: RNA
<213> ORGANISM: Artificial

```
<220> FEATURE:
<223> OTHER INFORMATION: anti-microRNA molecule

<400> SEQUENCE: 500
agcuuuggua accuagcuuu au                                              22

<210> SEQ ID NO 501
<211> LENGTH: 22
<212> TYPE: RNA
<213> ORGANISM: Artificial
<220> FEATURE:
<223> OTHER INFORMATION: anti-microRNA molecule

<400> SEQUENCE: 501
guucagaauc augucgaaag cu                                              22

<210> SEQ ID NO 502
<211> LENGTH: 22
<212> TYPE: RNA
<213> ORGANISM: Artificial
<220> FEATURE:
<223> OTHER INFORMATION: anti-microRNA molecule

<400> SEQUENCE: 502
cggcuuucaa cuaaugaucu ca                                              22

<210> SEQ ID NO 503
<211> LENGTH: 22
<212> TYPE: RNA
<213> ORGANISM: Artificial
<220> FEATURE:
<223> OTHER INFORMATION: anti-microRNA molecule

<400> SEQUENCE: 503
acuagcuuuc acgaugaucu ca                                              22

<210> SEQ ID NO 504
<211> LENGTH: 22
<212> TYPE: RNA
<213> ORGANISM: Artificial
<220> FEATURE:
<223> OTHER INFORMATION: anti-microRNA molecule

<400> SEQUENCE: 504
acuggcuuuc acgaugaucu ca                                              22

<210> SEQ ID NO 505
<211> LENGTH: 22
<212> TYPE: RNA
<213> ORGANISM: Artificial
<220> FEATURE:
<223> OTHER INFORMATION: anti-microRNA molecule

<400> SEQUENCE: 505
uuacugaauu uauauggugc ua                                              22

<210> SEQ ID NO 506
<211> LENGTH: 22
<212> TYPE: RNA
<213> ORGANISM: Artificial
<220> FEATURE:
<223> OTHER INFORMATION: anti-microRNA molecule

<400> SEQUENCE: 506
uacaauauua cauacuaccu ca                                              22
```

```
<210> SEQ ID NO 507
<211> LENGTH: 22
<212> TYPE: RNA
<213> ORGANISM: Artificial
<220> FEATURE:
<223> OTHER INFORMATION: anti-microRNA molecule

<400> SEQUENCE: 507
acgacuuuuc aaauacuuug ua                                              22

<210> SEQ ID NO 508
<211> LENGTH: 22
<212> TYPE: RNA
<213> ORGANISM: Artificial
<220> FEATURE:
<223> OTHER INFORMATION: anti-microRNA molecule

<400> SEQUENCE: 508
acuguggcaa agcauucacu ua                                              22

<210> SEQ ID NO 509
<211> LENGTH: 22
<212> TYPE: RNA
<213> ORGANISM: Artificial
<220> FEATURE:
<223> OTHER INFORMATION: anti-microRNA molecule

<400> SEQUENCE: 509
gcacaccuga aacuuugcuc ac                                              22

<210> SEQ ID NO 510
<211> LENGTH: 22
<212> TYPE: RNA
<213> ORGANISM: Artificial
<220> FEATURE:
<223> OTHER INFORMATION: anti-microRNA molecule

<400> SEQUENCE: 510
ggggcauuca aacaacauau ca                                              22

<210> SEQ ID NO 511
<211> LENGTH: 22
<212> TYPE: RNA
<213> ORGANISM: Artificial
<220> FEATURE:
<223> OTHER INFORMATION: anti-microRNA molecule

<400> SEQUENCE: 511
guggcauuca ccgcgugccu ua                                              22

<210> SEQ ID NO 512
<211> LENGTH: 22
<212> TYPE: RNA
<213> ORGANISM: Artificial
<220> FEATURE:
<223> OTHER INFORMATION: anti-microRNA molecule

<400> SEQUENCE: 512
cgugaauuca ugcagugcca uu                                              22

<210> SEQ ID NO 513
<211> LENGTH: 22
<212> TYPE: RNA
<213> ORGANISM: Artificial
<220> FEATURE:
<223> OTHER INFORMATION: anti-microRNA molecule
```

```
<400> SEQUENCE: 513
ggaaaagaua accaguguca uu                                           22

<210> SEQ ID NO 514
<211> LENGTH: 22
<212> TYPE: RNA
<213> ORGANISM: Artificial
<220> FEATURE:
<223> OTHER INFORMATION: anti-microRNA molecule

<400> SEQUENCE: 514
cuccuggucg cacaacuaau ac                                           22

<210> SEQ ID NO 515
<211> LENGTH: 22
<212> TYPE: RNA
<213> ORGANISM: Artificial
<220> FEATURE:
<223> OTHER INFORMATION: anti-microRNA molecule

<400> SEQUENCE: 515
cugccuguug aucacgagcu ua                                           22

<210> SEQ ID NO 516
<211> LENGTH: 22
<212> TYPE: RNA
<213> ORGANISM: Artificial
<220> FEATURE:
<223> OTHER INFORMATION: anti-microRNA molecule

<400> SEQUENCE: 516
caccgcaguu aagaugcauu ua                                           22

<210> SEQ ID NO 517
<211> LENGTH: 22
<212> TYPE: RNA
<213> ORGANISM: Artificial
<220> FEATURE:
<223> OTHER INFORMATION: anti-microRNA molecule

<400> SEQUENCE: 517
cccgcacaug cgcauugcuc aa                                           22

<210> SEQ ID NO 518
<211> LENGTH: 22
<212> TYPE: RNA
<213> ORGANISM: Artificial
<220> FEATURE:
<223> OTHER INFORMATION: anti-microRNA molecule

<400> SEQUENCE: 518
aaaggguauu cucgagcaau aa                                           22

<210> SEQ ID NO 519
<211> LENGTH: 22
<212> TYPE: RNA
<213> ORGANISM: Artificial
<220> FEATURE:
<223> OTHER INFORMATION: anti-microRNA molecule

<400> SEQUENCE: 519
ucaggccggg gagagugcaa ua                                           22

<210> SEQ ID NO 520
```

```
<211> LENGTH: 22
<212> TYPE: RNA
<213> ORGANISM: Artificial
<220> FEATURE:
<223> OTHER INFORMATION: anti-microRNA molecule

<400> SEQUENCE: 520
gcgucauuac cugacaguau ua                                              22

<210> SEQ ID NO 521
<211> LENGTH: 22
<212> TYPE: RNA
<213> ORGANISM: Artificial
<220> FEATURE:
<223> OTHER INFORMATION: anti-microRNA molecule

<400> SEQUENCE: 521
gcuguucgag aauucucagg ga                                              22

<210> SEQ ID NO 522
<211> LENGTH: 22
<212> TYPE: RNA
<213> ORGANISM: Artificial
<220> FEATURE:
<223> OTHER INFORMATION: anti-microRNA molecule

<400> SEQUENCE: 522
cugaauggca ucggaguaca aa                                              22

<210> SEQ ID NO 523
<211> LENGTH: 22
<212> TYPE: RNA
<213> ORGANISM: Artificial
<220> FEATURE:
<223> OTHER INFORMATION: anti-microRNA molecule

<400> SEQUENCE: 523
caguaccuau guguaguaca aa                                              22

<210> SEQ ID NO 524
<211> LENGTH: 22
<212> TYPE: RNA
<213> ORGANISM: Artificial
<220> FEATURE:
<223> OTHER INFORMATION: anti-microRNA molecule

<400> SEQUENCE: 524
caguacuuuu guguaguaca aa                                              22

<210> SEQ ID NO 525
<211> LENGTH: 22
<212> TYPE: RNA
<213> ORGANISM: Artificial
<220> FEATURE:
<223> OTHER INFORMATION: anti-microRNA molecule

<400> SEQUENCE: 525
agcgaagauu uggggggccag ua                                             22

<210> SEQ ID NO 526
<211> LENGTH: 22
<212> TYPE: RNA
<213> ORGANISM: Artificial
<220> FEATURE:
<223> OTHER INFORMATION: anti-microRNA molecule

<400> SEQUENCE: 526
```

```
gucauuucuc gcaccuaccu ca                                              22

<210> SEQ ID NO 527
<211> LENGTH: 22
<212> TYPE: RNA
<213> ORGANISM: Artificial
<220> FEATURE:
<223> OTHER INFORMATION: anti-microRNA molecule

<400> SEQUENCE: 527
cucgaagcaa aggccuacgc aa                                              22

<210> SEQ ID NO 528
<211> LENGTH: 22
<212> TYPE: RNA
<213> ORGANISM: Artificial
<220> FEATURE:
<223> OTHER INFORMATION: anti-microRNA molecule

<400> SEQUENCE: 528
auaucccgcc gcgaucguac cg                                              22

<210> SEQ ID NO 529
<211> LENGTH: 22
<212> TYPE: RNA
<213> ORGANISM: Artificial
<220> FEATURE:
<223> OTHER INFORMATION: anti-microRNA molecule

<400> SEQUENCE: 529
uaccacuuug uacaaccaaa ga                                              22

<210> SEQ ID NO 530
<211> LENGTH: 22
<212> TYPE: RNA
<213> ORGANISM: Artificial
<220> FEATURE:
<223> OTHER INFORMATION: anti-microRNA molecule

<400> SEQUENCE: 530
gagcuacuug gaggggacca au                                              22

<210> SEQ ID NO 531
<211> LENGTH: 22
<212> TYPE: RNA
<213> ORGANISM: Artificial
<220> FEATURE:
<223> OTHER INFORMATION: anti-microRNA molecule

<400> SEQUENCE: 531
agcuccuacc cgaaacaugu aa                                              22

<210> SEQ ID NO 532
<211> LENGTH: 22
<212> TYPE: RNA
<213> ORGANISM: Artificial
<220> FEATURE:
<223> OTHER INFORMATION: anti-microRNA molecule

<400> SEQUENCE: 532
agaagagaau aggcucuagu ca                                              22

<210> SEQ ID NO 533
<211> LENGTH: 22
<212> TYPE: RNA
```

```
<213> ORGANISM: Artificial
<220> FEATURE:
<223> OTHER INFORMATION: anti-microRNA molecule

<400> SEQUENCE: 533
gagcguuauc cgugcacgug ua                                              22

<210> SEQ ID NO 534
<211> LENGTH: 22
<212> TYPE: RNA
<213> ORGANISM: Artificial
<220> FEATURE:
<223> OTHER INFORMATION: anti-microRNA molecule

<400> SEQUENCE: 534
gcaacgcuca aaaguccugu ga                                              22

<210> SEQ ID NO 535
<211> LENGTH: 22
<212> TYPE: RNA
<213> ORGANISM: Artificial
<220> FEATURE:
<223> OTHER INFORMATION: anti-microRNA molecule

<400> SEQUENCE: 535
ccaugccaac aguugacugu ga                                              22

<210> SEQ ID NO 536
<211> LENGTH: 22
<212> TYPE: RNA
<213> ORGANISM: Artificial
<220> FEATURE:
<223> OTHER INFORMATION: anti-microRNA molecule

<400> SEQUENCE: 536
uaagagcggc accacuacuu aa                                              22

<210> SEQ ID NO 537
<211> LENGTH: 22
<212> TYPE: RNA
<213> ORGANISM: Artificial
<220> FEATURE:
<223> OTHER INFORMATION: anti-microRNA molecule

<400> SEQUENCE: 537
uuaccugcgg cacuacuacu ua                                              22

<210> SEQ ID NO 538
<211> LENGTH: 22
<212> TYPE: RNA
<213> ORGANISM: Artificial
<220> FEATURE:
<223> OTHER INFORMATION: anti-microRNA molecule

<400> SEQUENCE: 538
uggucagugu uagugaggug ug                                              22

<210> SEQ ID NO 539
<211> LENGTH: 22
<212> TYPE: RNA
<213> ORGANISM: Artificial
<220> FEATURE:
<223> OTHER INFORMATION: anti-microRNA molecule

<400> SEQUENCE: 539
cuacagucgc gaaagauuug ca                                              22
```

```
<210> SEQ ID NO 540
<211> LENGTH: 22
<212> TYPE: RNA
<213> ORGANISM: Artificial
<220> FEATURE:
<223> OTHER INFORMATION: anti-microRNA molecule

<400> SEQUENCE: 540
guacagucuu cuaugcauuc ca                                        22

<210> SEQ ID NO 541
<211> LENGTH: 22
<212> TYPE: RNA
<213> ORGANISM: Artificial
<220> FEATURE:
<223> OTHER INFORMATION: anti-microRNA molecule

<400> SEQUENCE: 541
ucacugggua cuccugauac uc                                        22

<210> SEQ ID NO 542
<211> LENGTH: 22
<212> TYPE: RNA
<213> ORGANISM: Artificial
<220> FEATURE:
<223> OTHER INFORMATION: anti-microRNA molecule

<400> SEQUENCE: 542
uaaaaggauu ccucucaaaa cc                                        22

<210> SEQ ID NO 543
<211> LENGTH: 22
<212> TYPE: RNA
<213> ORGANISM: Artificial
<220> FEATURE:
<223> OTHER INFORMATION: anti-microRNA molecule

<400> SEQUENCE: 543
ccagauuagg augagauuua cu                                        22

<210> SEQ ID NO 544
<211> LENGTH: 22
<212> TYPE: RNA
<213> ORGANISM: Artificial
<220> FEATURE:
<223> OTHER INFORMATION: anti-microRNA molecule

<400> SEQUENCE: 544
uccuacaaga guucgacauc ac                                        22

<210> SEQ ID NO 545
<211> LENGTH: 22
<212> TYPE: RNA
<213> ORGANISM: Artificial
<220> FEATURE:
<223> OTHER INFORMATION: anti-microRNA molecule

<400> SEQUENCE: 545
caccgugaaa acuaaaaagc ua                                        22

<210> SEQ ID NO 546
<211> LENGTH: 22
<212> TYPE: RNA
<213> ORGANISM: Artificial
<220> FEATURE:
```

```
<223> OTHER INFORMATION: anti-microRNA molecule

<400> SEQUENCE: 546
guaucagaaa acaucgagaa ac                                              22

<210> SEQ ID NO 547
<211> LENGTH: 22
<212> TYPE: RNA
<213> ORGANISM: Artificial
<220> FEATURE:
<223> OTHER INFORMATION: anti-microRNA molecule

<400> SEQUENCE: 547
cccauaacaa caaccacccg cc                                              22

<210> SEQ ID NO 548
<211> LENGTH: 22
<212> TYPE: RNA
<213> ORGANISM: Artificial
<220> FEATURE:
<223> OTHER INFORMATION: anti-microRNA molecule

<400> SEQUENCE: 548
aaauaccacc cuuccucccu ca                                              22

<210> SEQ ID NO 549
<211> LENGTH: 22
<212> TYPE: RNA
<213> ORGANISM: Artificial
<220> FEATURE:
<223> OTHER INFORMATION: anti-microRNA molecule

<400> SEQUENCE: 549
aagcuuugcc aaagucuugc cu                                              22

<210> SEQ ID NO 550
<211> LENGTH: 22
<212> TYPE: RNA
<213> ORGANISM: Artificial
<220> FEATURE:
<223> OTHER INFORMATION: anti-microRNA molecule

<400> SEQUENCE: 550
auugcagcag acacuucacg gg                                              22

<210> SEQ ID NO 551
<211> LENGTH: 22
<212> TYPE: RNA
<213> ORGANISM: Artificial
<220> FEATURE:
<223> OTHER INFORMATION: anti-microRNA molecule

<400> SEQUENCE: 551
caaacugcuu cuaauucuug cc                                              22

<210> SEQ ID NO 552
<211> LENGTH: 22
<212> TYPE: RNA
<213> ORGANISM: Artificial
<220> FEATURE:
<223> OTHER INFORMATION: anti-microRNA molecule

<400> SEQUENCE: 552
caaguuuugc cagagucuug cc                                              22
```

```
<210> SEQ ID NO 553
<211> LENGTH: 22
<212> TYPE: RNA
<213> ORGANISM: Artificial
<220> FEATURE:
<223> OTHER INFORMATION: anti-microRNA molecule

<400> SEQUENCE: 553
aucuccacug cuacaucaug cc                                              22

<210> SEQ ID NO 554
<211> LENGTH: 22
<212> TYPE: RNA
<213> ORGANISM: Artificial
<220> FEATURE:
<223> OTHER INFORMATION: anti-microRNA molecule

<400> SEQUENCE: 554
cgaaugcuuu cccacccggc ga                                              22

<210> SEQ ID NO 555
<211> LENGTH: 22
<212> TYPE: RNA
<213> ORGANISM: Artificial
<220> FEATURE:
<223> OTHER INFORMATION: anti-microRNA molecule

<400> SEQUENCE: 555
cuuccaaaca cccaugccua ca                                              22

<210> SEQ ID NO 556
<211> LENGTH: 22
<212> TYPE: RNA
<213> ORGANISM: Artificial
<220> FEATURE:
<223> OTHER INFORMATION: anti-microRNA molecule

<400> SEQUENCE: 556
agcagccgac acaguacggg ca                                              22

<210> SEQ ID NO 557
<211> LENGTH: 22
<212> TYPE: RNA
<213> ORGANISM: Artificial
<220> FEATURE:
<223> OTHER INFORMATION: anti-microRNA molecule

<400> SEQUENCE: 557
gaauucuucc agugccauua ac                                              22

<210> SEQ ID NO 558
<211> LENGTH: 22
<212> TYPE: RNA
<213> ORGANISM: Artificial
<220> FEATURE:
<223> OTHER INFORMATION: anti-microRNA molecule

<400> SEQUENCE: 558
gcccuuauca guucuccguc ca                                              22

<210> SEQ ID NO 559
<211> LENGTH: 22
<212> TYPE: RNA
<213> ORGANISM: Artificial
<220> FEATURE:
<223> OTHER INFORMATION: anti-microRNA molecule
```

-continued

```
<400> SEQUENCE: 559
cccguuagug ucggucacaa aa                                              22

<210> SEQ ID NO 560
<211> LENGTH: 22
<212> TYPE: RNA
<213> ORGANISM: Artificial
<220> FEATURE:
<223> OTHER INFORMATION: anti-microRNA molecule

<400> SEQUENCE: 560
gcgcgcuacu ucagguaccu ga                                              22

<210> SEQ ID NO 561
<211> LENGTH: 22
<212> TYPE: RNA
<213> ORGANISM: Artificial
<220> FEATURE:
<223> OTHER INFORMATION: anti-microRNA molecule

<400> SEQUENCE: 561
auaggccggg acaagugcaa ug                                              22

<210> SEQ ID NO 562
<211> LENGTH: 22
<212> TYPE: RNA
<213> ORGANISM: Artificial
<220> FEATURE:
<223> OTHER INFORMATION: anti-microRNA molecule

<400> SEQUENCE: 562
aagaauugcg uuuggacaau ca                                              22

<210> SEQ ID NO 563
<211> LENGTH: 22
<212> TYPE: RNA
<213> ORGANISM: Artificial
<220> FEATURE:
<223> OTHER INFORMATION: anti-microRNA molecule

<400> SEQUENCE: 563
agagcacggu augaaguucc ua                                              22

<210> SEQ ID NO 564
<211> LENGTH: 22
<212> TYPE: RNA
<213> ORGANISM: Artificial
<220> FEATURE:
<223> OTHER INFORMATION: anti-microRNA molecule

<400> SEQUENCE: 564
gucguaccag auagugcauu ua                                              22

<210> SEQ ID NO 565
<211> LENGTH: 22
<212> TYPE: RNA
<213> ORGANISM: Artificial
<220> FEATURE:
<223> OTHER INFORMATION: anti-microRNA molecule

<400> SEQUENCE: 565
aaacggacga aagucccacc ga                                              22

<210> SEQ ID NO 566
<211> LENGTH: 22
```

```
<212> TYPE: RNA
<213> ORGANISM: Artificial
<220> FEATURE:
<223> OTHER INFORMATION: anti-microRNA molecule

<400> SEQUENCE: 566
acagcugguu gaaggggacc aa                                            22

<210> SEQ ID NO 567
<211> LENGTH: 22
<212> TYPE: RNA
<213> ORGANISM: Artificial
<220> FEATURE:
<223> OTHER INFORMATION: anti-microRNA molecule

<400> SEQUENCE: 567
uuaaugagug uggaucuagu ca                                            22

<210> SEQ ID NO 568
<211> LENGTH: 22
<212> TYPE: RNA
<213> ORGANISM: Artificial
<220> FEATURE:
<223> OTHER INFORMATION: anti-microRNA molecule

<400> SEQUENCE: 568
acaaugcgac uacaaugcac cu                                            22

<210> SEQ ID NO 569
<211> LENGTH: 22
<212> TYPE: RNA
<213> ORGANISM: Artificial
<220> FEATURE:
<223> OTHER INFORMATION: anti-microRNA molecule

<400> SEQUENCE: 569
uuucauaugc aacguaaaua ca                                            22

<210> SEQ ID NO 570
<211> LENGTH: 22
<212> TYPE: RNA
<213> ORGANISM: Artificial
<220> FEATURE:
<223> OTHER INFORMATION: anti-microRNA molecule

<400> SEQUENCE: 570
caaagagagc aauuccauga ca                                            22

<210> SEQ ID NO 571
<211> LENGTH: 22
<212> TYPE: RNA
<213> ORGANISM: Artificial
<220> FEATURE:
<223> OTHER INFORMATION: anti-microRNA molecule

<400> SEQUENCE: 571
aaagccuagu agaggcuaga uu                                            22

<210> SEQ ID NO 572
<211> LENGTH: 22
<212> TYPE: RNA
<213> ORGANISM: Artificial
<220> FEATURE:
<223> OTHER INFORMATION: anti-microRNA molecule

<400> SEQUENCE: 572
```
cagaauuacc agcugauauu ua 22

<210> SEQ ID NO 573
<211> LENGTH: 22
<212> TYPE: RNA
<213> ORGANISM: Artificial
<220> FEATURE:
<223> OTHER INFORMATION: anti-microRNA molecule

<400> SEQUENCE: 573
uggaaucaag uugcugacuu ca 22

<210> SEQ ID NO 574
<211> LENGTH: 22
<212> TYPE: RNA
<213> ORGANISM: Artificial
<220> FEATURE:
<223> OTHER INFORMATION: anti-microRNA molecule

<400> SEQUENCE: 574
caaccagcua accacacugc ca 22

<210> SEQ ID NO 575
<211> LENGTH: 22
<212> TYPE: RNA
<213> ORGANISM: Artificial
<220> FEATURE:
<223> OTHER INFORMATION: anti-microRNA molecule

<400> SEQUENCE: 575
uuggcauuca ccgcgugccu ua 22

<210> SEQ ID NO 576
<211> LENGTH: 22
<212> TYPE: RNA
<213> ORGANISM: Artificial
<220> FEATURE:
<223> OTHER INFORMATION: anti-microRNA molecule

<400> SEQUENCE: 576
augcuuuggu aaucuagcuu ua 22

<210> SEQ ID NO 577
<211> LENGTH: 22
<212> TYPE: RNA
<213> ORGANISM: Artificial
<220> FEATURE:
<223> OTHER INFORMATION: anti-microRNA molecule

<400> SEQUENCE: 577
agagcacggu auuaaguucc ua 22

<210> SEQ ID NO 578
<211> LENGTH: 22
<212> TYPE: RNA
<213> ORGANISM: Artificial
<220> FEATURE:
<223> OTHER INFORMATION: anti-microRNA molecule

<400> SEQUENCE: 578
auagccgcug ucacacgcac aa 22

<210> SEQ ID NO 579
<211> LENGTH: 22
<212> TYPE: RNA
<213> ORGANISM: Artificial

```
<220> FEATURE:
<223> OTHER INFORMATION: anti-microRNA molecule

<400> SEQUENCE: 579
gcacugauuu cgaauggugc ua                                              22

<210> SEQ ID NO 580
<211> LENGTH: 22
<212> TYPE: RNA
<213> ORGANISM: Artificial
<220> FEATURE:
<223> OTHER INFORMATION: anti-microRNA molecule

<400> SEQUENCE: 580
cacaaguucg gauuuacggg uu                                              22

<210> SEQ ID NO 581
<211> LENGTH: 22
<212> TYPE: RNA
<213> ORGANISM: Artificial
<220> FEATURE:
<223> OTHER INFORMATION: anti-microRNA molecule

<400> SEQUENCE: 581
gcaggccggg acuagugcaa uu                                              22

<210> SEQ ID NO 582
<211> LENGTH: 22
<212> TYPE: RNA
<213> ORGANISM: Artificial
<220> FEATURE:
<223> OTHER INFORMATION: anti-microRNA molecule

<400> SEQUENCE: 582
gcacgagugu ucggucuagu ca                                              22

<210> SEQ ID NO 583
<211> LENGTH: 22
<212> TYPE: RNA
<213> ORGANISM: Artificial
<220> FEATURE:
<223> OTHER INFORMATION: anti-microRNA molecule

<400> SEQUENCE: 583
cgugcaaacg auuuucaaca ca                                              22

<210> SEQ ID NO 584
<211> LENGTH: 22
<212> TYPE: RNA
<213> ORGANISM: Artificial
<220> FEATURE:
<223> OTHER INFORMATION: anti-microRNA molecule

<400> SEQUENCE: 584
acacaccuga aauuuugcuc aa                                              22

<210> SEQ ID NO 585
<211> LENGTH: 22
<212> TYPE: RNA
<213> ORGANISM: Artificial
<220> FEATURE:
<223> OTHER INFORMATION: anti-microRNA molecule

<400> SEQUENCE: 585
ugugaauucu cccagugcca ag                                              22
```

```
<210> SEQ ID NO 586
<211> LENGTH: 22
<212> TYPE: RNA
<213> ORGANISM: Artificial
<220> FEATURE:
<223> OTHER INFORMATION: anti-microRNA molecule

<400> SEQUENCE: 586
augaaaugaa aucgacauga aa                                              22

<210> SEQ ID NO 587
<211> LENGTH: 22
<212> TYPE: RNA
<213> ORGANISM: Artificial
<220> FEATURE:
<223> OTHER INFORMATION: anti-microRNA molecule

<400> SEQUENCE: 587
gcaggcucca cuuaaauauu ua                                              22

<210> SEQ ID NO 588
<211> LENGTH: 22
<212> TYPE: RNA
<213> ORGANISM: Artificial
<220> FEATURE:
<223> OTHER INFORMATION: anti-microRNA molecule

<400> SEQUENCE: 588
aucagcuuuc aaaaugaucu ca                                              22

<210> SEQ ID NO 589
<211> LENGTH: 22
<212> TYPE: RNA
<213> ORGANISM: Artificial
<220> FEATURE:
<223> OTHER INFORMATION: anti-microRNA molecule

<400> SEQUENCE: 589
ccaguuuccu gugaaaccua aa                                              22

<210> SEQ ID NO 590
<211> LENGTH: 22
<212> TYPE: RNA
<213> ORGANISM: Artificial
<220> FEATURE:
<223> OTHER INFORMATION: anti-microRNA molecule

<400> SEQUENCE: 590
cagcuauucc gacaucuugc ca                                              22

<210> SEQ ID NO 591
<211> LENGTH: 22
<212> TYPE: RNA
<213> ORGANISM: Artificial
<220> FEATURE:
<223> OTHER INFORMATION: anti-microRNA molecule

<400> SEQUENCE: 591
ucacauuuac aaauugagau ua                                              22

<210> SEQ ID NO 592
<211> LENGTH: 22
<212> TYPE: RNA
<213> ORGANISM: Artificial
<220> FEATURE:
<223> OTHER INFORMATION: anti-microRNA molecule
```

```
<400> SEQUENCE: 592
agagcaccug augaaguaca au                                        22

<210> SEQ ID NO 593
<211> LENGTH: 22
<212> TYPE: RNA
<213> ORGANISM: Artificial
<220> FEATURE:
<223> OTHER INFORMATION: anti-microRNA molecule

<400> SEQUENCE: 593
ucuacagcua gaauaccaaa ga                                        22

<210> SEQ ID NO 594
<211> LENGTH: 22
<212> TYPE: RNA
<213> ORGANISM: Artificial
<220> FEATURE:
<223> OTHER INFORMATION: anti-microRNA molecule

<400> SEQUENCE: 594
uugagaguca cuaaguaccu ga                                        22

<210> SEQ ID NO 595
<211> LENGTH: 22
<212> TYPE: RNA
<213> ORGANISM: Artificial
<220> FEATURE:
<223> OTHER INFORMATION: anti-microRNA molecule

<400> SEQUENCE: 595
auacagcuaa aaucaccaaa ga                                        22

<210> SEQ ID NO 596
<211> LENGTH: 22
<212> TYPE: RNA
<213> ORGANISM: Artificial
<220> FEATURE:
<223> OTHER INFORMATION: anti-microRNA molecule

<400> SEQUENCE: 596
ucacaaguua gggucucagg ga                                        22

<210> SEQ ID NO 597
<211> LENGTH: 22
<212> TYPE: RNA
<213> ORGANISM: Artificial
<220> FEATURE:
<223> OTHER INFORMATION: anti-microRNA molecule

<400> SEQUENCE: 597
cgcucacuca aggagguugu ga                                        22

<210> SEQ ID NO 598
<211> LENGTH: 22
<212> TYPE: RNA
<213> ORGANISM: Artificial
<220> FEATURE:
<223> OTHER INFORMATION: anti-microRNA molecule

<400> SEQUENCE: 598
cucacaguau aauccuguga uu                                        22

<210> SEQ ID NO 599
```

```
<211> LENGTH: 22
<212> TYPE: RNA
<213> ORGANISM: Artificial
<220> FEATURE:
<223> OTHER INFORMATION: anti-microRNA molecule

<400> SEQUENCE: 599
cagcuaugcc gacaucuugc ca                                           22

<210> SEQ ID NO 600
<211> LENGTH: 22
<212> TYPE: RNA
<213> ORGANISM: Artificial
<220> FEATURE:
<223> OTHER INFORMATION: anti-microRNA molecule

<400> SEQUENCE: 600
uaggacaaac uuuacccagu gc                                           22

<210> SEQ ID NO 601
<211> LENGTH: 22
<212> TYPE: RNA
<213> ORGANISM: Artificial
<220> FEATURE:
<223> OTHER INFORMATION: anti-microRNA molecule

<400> SEQUENCE: 601
aaaggccggg aagugugcaa ua                                           22

<210> SEQ ID NO 602
<211> LENGTH: 22
<212> TYPE: RNA
<213> ORGANISM: Artificial
<220> FEATURE:
<223> OTHER INFORMATION: anti-microRNA molecule

<400> SEQUENCE: 602
ucaggccggu gaaugugcaa ua                                           22

<210> SEQ ID NO 603
<211> LENGTH: 22
<212> TYPE: RNA
<213> ORGANISM: Artificial
<220> FEATURE:
<223> OTHER INFORMATION: anti-microRNA molecule

<400> SEQUENCE: 603
ucaggccguc ucaagugcaa ua                                           22

<210> SEQ ID NO 604
<211> LENGTH: 22
<212> TYPE: RNA
<213> ORGANISM: Artificial
<220> FEATURE:
<223> OTHER INFORMATION: anti-microRNA molecule

<400> SEQUENCE: 604
ucgggcugug aaaagugcaa ua                                           22

<210> SEQ ID NO 605
<211> LENGTH: 21
<212> TYPE: RNA
<213> ORGANISM: Artificial
<220> FEATURE:
<223> OTHER INFORMATION: anti-microRNA molecule

<400> SEQUENCE: 605
```

```
ccgaacuuau uggcucgaau a                                              21

<210> SEQ ID NO 606
<211> LENGTH: 22
<212> TYPE: RNA
<213> ORGANISM: Artificial
<220> FEATURE:
<223> OTHER INFORMATION: anti-microRNA molecule

<400> SEQUENCE: 606
gcuuucugag caacaaucaa aa                                             22

<210> SEQ ID NO 607
<211> LENGTH: 22
<212> TYPE: RNA
<213> ORGANISM: Artificial
<220> FEATURE:
<223> OTHER INFORMATION: anti-microRNA molecule

<400> SEQUENCE: 607
cgccaguaag cggaaaaaga ca                                             22

<210> SEQ ID NO 608
<211> LENGTH: 22
<212> TYPE: RNA
<213> ORGANISM: Artificial
<220> FEATURE:
<223> OTHER INFORMATION: anti-microRNA molecule

<400> SEQUENCE: 608
uggauaccac cagcuguguu ca                                             22

<210> SEQ ID NO 609
<211> LENGTH: 22
<212> TYPE: RNA
<213> ORGANISM: Artificial
<220> FEATURE:
<223> OTHER INFORMATION: anti-microRNA molecule

<400> SEQUENCE: 609
ugagauaaac aaagcccagu ga                                             22

<210> SEQ ID NO 610
<211> LENGTH: 22
<212> TYPE: RNA
<213> ORGANISM: Artificial
<220> FEATURE:
<223> OTHER INFORMATION: anti-microRNA molecule

<400> SEQUENCE: 610
cccaucaaag cuggcuguga ua                                             22

<210> SEQ ID NO 611
<211> LENGTH: 22
<212> TYPE: RNA
<213> ORGANISM: Artificial
<220> FEATURE:
<223> OTHER INFORMATION: anti-microRNA molecule

<400> SEQUENCE: 611
ucaggauaca uucaguauac gu                                             22

<210> SEQ ID NO 612
<211> LENGTH: 22
<212> TYPE: RNA
```

```
<213> ORGANISM: Artificial
<220> FEATURE:
<223> OTHER INFORMATION: anti-microRNA molecule

<400> SEQUENCE: 612
uacguauacu gaagguauac cg                                           22

<210> SEQ ID NO 613
<211> LENGTH: 23
<212> TYPE: RNA
<213> ORGANISM: Artificial
<220> FEATURE:
<223> OTHER INFORMATION: 2'-O-methyl microRNA molecule
<220> FEATURE:
<221> NAME/KEY: misc_structure
<222> LOCATION: (23)..(23)
<223> OTHER INFORMATION: 3' aminolinker attached to the a nucleotide at
      position 23

<400> SEQUENCE: 613
gucaacauca gucugauaag cua                                          23

<210> SEQ ID NO 614
<211> LENGTH: 21
<212> TYPE: RNA
<213> ORGANISM: Artificial
<220> FEATURE:
<223> OTHER INFORMATION: 2'-O-methyl antisense molecule
<220> FEATURE:
<221> NAME/KEY: misc_structure
<222> LOCATION: (21)..(21)
<223> OTHER INFORMATION: 3' aminolinker attached to the u nucleotide at
      position 21

<400> SEQUENCE: 614
aaggcaagcu gacccugaag u                                            21

<210> SEQ ID NO 615
<211> LENGTH: 21
<212> TYPE: RNA
<213> ORGANISM: Artificial
<220> FEATURE:
<223> OTHER INFORMATION: 2' O- methyl reverse seqeunce
<220> FEATURE:
<221> NAME/KEY: misc_structure
<222> LOCATION: (21)..(21)
<223> OTHER INFORMATION: 3' aminolinker attached to the a nucleotide at
      position 21

<400> SEQUENCE: 615
ugaagcccca gucgaacgga a                                            21

<210> SEQ ID NO 616
<211> LENGTH: 26
<212> TYPE: DNA
<213> ORGANISM: Artificial
<220> FEATURE:
<223> OTHER INFORMATION: 2'-deoxy microRNA molecule
<220> FEATURE:
<221> NAME/KEY: misc_structure
<222> LOCATION: (26)..(26)
<223> OTHER INFORMATION: 3' aminolinker attached to the g nucleotide at
      position 26

<400> SEQUENCE: 616
gtcaacatca gtctgataag ctagcg                                       26

<210> SEQ ID NO 617
<211> LENGTH: 24
```

```
<212> TYPE: DNA
<213> ORGANISM: Artificial
<220> FEATURE:
<223> OTHER INFORMATION: 2'-deoxy antisense molecule
<220> FEATURE:
<221> NAME/KEY: misc_structure
<222> LOCATION: (24)..(24)
<223> OTHER INFORMATION: 3' aminolinker attached to the g nucleotide at
      position 24

<400> SEQUENCE: 617
aaggcaagct gaccctgaag tgcg                                           24

<210> SEQ ID NO 618
<211> LENGTH: 88
<212> TYPE: DNA
<213> ORGANISM: Artificial
<220> FEATURE:
<223> OTHER INFORMATION: primer

<400> SEQUENCE: 618
gaacaattgc ttttacagat gcacatatcg aggtgaacat cacgtacgtc aacatcagtc    60
tgataagcta tcggttggca gaagctat                                       88

<210> SEQ ID NO 619
<211> LENGTH: 90
<212> TYPE: DNA
<213> ORGANISM: Artificial
<220> FEATURE:
<223> OTHER INFORMATION: primer

<400> SEQUENCE: 619
ggcataaaga attgaagaga gttttcactg catacgacga ttctgtgatt tgtattcagc    60
ccatatcgtt tcatagcttc tgccaaccga                                     90

<210> SEQ ID NO 620
<211> LENGTH: 35
<212> TYPE: DNA
<213> ORGANISM: Artificial
<220> FEATURE:
<223> OTHER INFORMATION: primer

<400> SEQUENCE: 620
taatacgact cactatagaa caattgcttt tacag                               35

<210> SEQ ID NO 621
<211> LENGTH: 35
<212> TYPE: DNA
<213> ORGANISM: Artificial
<220> FEATURE:
<223> OTHER INFORMATION: primer

<400> SEQUENCE: 621
atttaggtga cactataggc ataaagaatt gaaga                               35

<210> SEQ ID NO 622
<211> LENGTH: 33
<212> TYPE: DNA
<213> ORGANISM: Artificial
<220> FEATURE:
<223> OTHER INFORMATION: synthetic oligonucleotide molecule

<400> SEQUENCE: 622
ggcctcaaca tcagtctgat aagctaggta cct                                 33
```

```
<210> SEQ ID NO 623
<211> LENGTH: 33
<212> TYPE: DNA
<213> ORGANISM: Artificial
<220> FEATURE:
<223> OTHER INFORMATION: synthetic oligonucleotide molecule

<400> SEQUENCE: 623
ggccaggtac ctagcttatc agactgatgt tga                                    33
```

ANTI-MICRORNA OLIGONUCLEOTIDE MOLECULES

The invention claimed herein was made with the help of grant number 1 R01 GM068476-01 from NIH/NIGMS. The U.S. government has certain rights in the invention.

This application is a U.S. National Phase Application of International Application No. PCT/US05/04714 filed on Feb. 11, 2005 and asserts priority to U.S. application Ser. No. 10/845,057 filed on May 13, 2004, which is a continuing application of U.S. application Ser. No. 10/778,908 filed on Feb. 13, 2004. The specifications of International Application No. PCT/US05/04714, U.S. application Ser. No. 10/845,057, and U.S. application Ser. No. 10/778,908 are hereby incorporated by reference in their entirety.

BACKGROUND OF THE INVENTION

RNA silencing is a fundamental mechanism of gene regulation that uses double-stranded RNA (dsRNA) derived 21- to 28-nucleotide (nt) small RNAs to guide mRNA degradation, control mRNA translation or chromatin modification. Recently, several hundred novel genes were identified in plants and animals that encode transcripts that contain short dsRNA hairpins.

Defined 22-nt RNAs, referred to as microRNAs (miR-NAs), are reported to be excised by dsRNA specific endonucleases from the hairpin precursors. The miRNAs are incorporated into ribonucleoprotein particles (miRNPs).

Plant miRNAs target mRNAs containing sequence segments with high complementarity for degradation or suppress translation of partially complementary mRNAs. Animal miRNAs appear to act predominantly as translational repressors. However, animal miRNAs have also been reported to guide RNA degradation. This indicates that animal miRNPs act like small interfering RNA (siRNA)-induced silencing complexes (RISCs).

Understanding the biological function of miRNAs requires knowledge of their mRNA targets. Bioinformatic approaches have been used to predict mRNA targets, among which transcription factors and proapoptotic genes were prominent candidates. Processes such as Notch signaling, cell proliferation, morphogenesis and axon guidance appear to be controlled by miRNA genes.

Therefore, there is a need for materials and methods that can help elucidate the function of known and future microRNAs. Due to the ability of microRNAs to induce RNA degradation or repress translation of mRNA which encode important proteins, there is also a need for novel compositions for inhibiting microRNA-induced cleavage or repression of mRNAs.

SUMMARY THE INVENTION

In one embodiment, the invention provides an isolated single stranded anti-microRNA molecule comprising a minimum of ten moieties and a maximum of fifty moieties on a molecular backbone, the molecular backbone comprising backbone units, each moiety comprising a base bonded to a backbone unit, each base forming a Watson-Crick base pair with a complementary base wherein at least ten contiguous bases have the same sequence as a sequence of bases in any one of the anti-microRNA molecules shown in Tables 1-4, except that up to thirty percent of the bases pairs may be wobble base pairs, and up to 10% of the contiguous bases may be additions, deletions, mismatches, or combinations thereof; no more than fifty percent of the contiguous moieties contain deoxyribonuleotide backbone units; the moiety in the molecule at the position corresponding to position 11 of the microRNA is non-complementary; and the molecule is capable of inhibiting microRNP activity.

In another embodiment, the invention provides a method for inhibiting microRNP activity in a cell, the microRNP comprising a microRNA molecule, the microRNA molecule comprising a sequences of bases complementary of the sequence of bases in a single stranded anti-microRNA molecule, the method comprising introducing into the cell the single-stranded anti-microRNA molecule comprising a sequence of a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases of the anti-microRNA molecule are complementary to the microRNA, except that up to thirty percent of the bases may be substituted by wobble base pairs, and up to ten percent of the at least ten moieties may be additions, deletions, mismatches, or combinations thereof; no more than fifty percent of the contiguous moieties contain deoxyribonuleotide backbone units; and the moiety in the molecule at the position corresponding to position 11 of the microRNA is non-complementary.

In another embodiment, the invention provides an isolated microRNA molecule comprising a minimum of ten moieties and a maximum of fifty moieties on a molecular backbone, the molecular backbone comprising backbone units, each moiety comprising a base bonded to a backbone unit, wherein at least ten contiguous bases have the same sequence as a sequence of bases in any one of the microRNA molecules shown in Table 2, except that up to thirty percent of the bases pairs may be wobble base pairs, and up to 10% of the contiguous bases may be additions, deletions, mismatches, or combinations thereof; and no more than fifty percent of the contiguous moieties contain deoxyribonuleotide backbone units.

In another embodiment, the invention provides an isolated microRNA molecule comprising a minimum of ten moieties and a maximum of fifty moieties on a molecular backbone, the molecular backbone comprising backbone units, each moiety comprising a base bonded to a backbone unit, wherein at least ten contiguous bases have any one of the microRNA sequences shown in Tables 1, 3 and 4, except that up to thirty percent of the bases pairs may be wobble base pairs, and up to 10% of the contiguous bases may be additions, deletions, mismatches, or combinations thereof; no more than fifty percent of the contiguous moieties contain deoxyribonuleotide backbone units; and is modified for increased nuclease resistance.

In yet another embodiment, the invention provides an isolated single stranded anti-microRNA molecule comprising a minimum of ten moieties and a maximum of fifty moieties on a molecular backbone, the molecular backbone comprising backbone units, each moiety comprising a base bonded to a backbone unit, each base forming a Watson-Crick base pair with a complementary base wherein at least ten contiguous bases have the same sequence as a sequence of bases in any one of the anti-microRNA molecules shown in Tables 1-4, except that up to thirty percent of the bases pairs may be wobble base pairs, and up to 10% of the contiguous bases may be additions; deletions, mismatches, or combinations thereof; no more than fifty percent of the contiguous moieties contain deoxyribonuleotide backbone units; and the molecule is capable of inhibiting microRNP activity.

In yet a further embodiment, the invention provides a method for inhibiting microRNP activity in a cell, the microRNP comprising a microRNA molecule, the microRNA molecule comprising a sequences of bases complementary of the sequence of bases in a single stranded anti-microRNA molecule, the method comprising introducing into the cell the single-stranded anti-microRNA molecule comprising a sequence of a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases of the anti-microRNA molecule are complementary to the microRNA, except that up to thirty percent of the bases may be substituted by wobble base pairs, and up to ten percent of the at least ten moieties may be additions, deletions, mismatches, or combinations thereof; and no more than fifty percent of the contiguous moieties contain deoxyribonuleotide backbone units.

DESCRIPTION OF THE FIGURES

FIG. 1 shows the modified nucleotide units discussed in the specification. B denotes any one of the following nucleic acid bases: adenosine, cytidine, guanosine, thymine, or uridine.

DETAILED DESCRIPTION OF THE INVENTION

Figure 2:
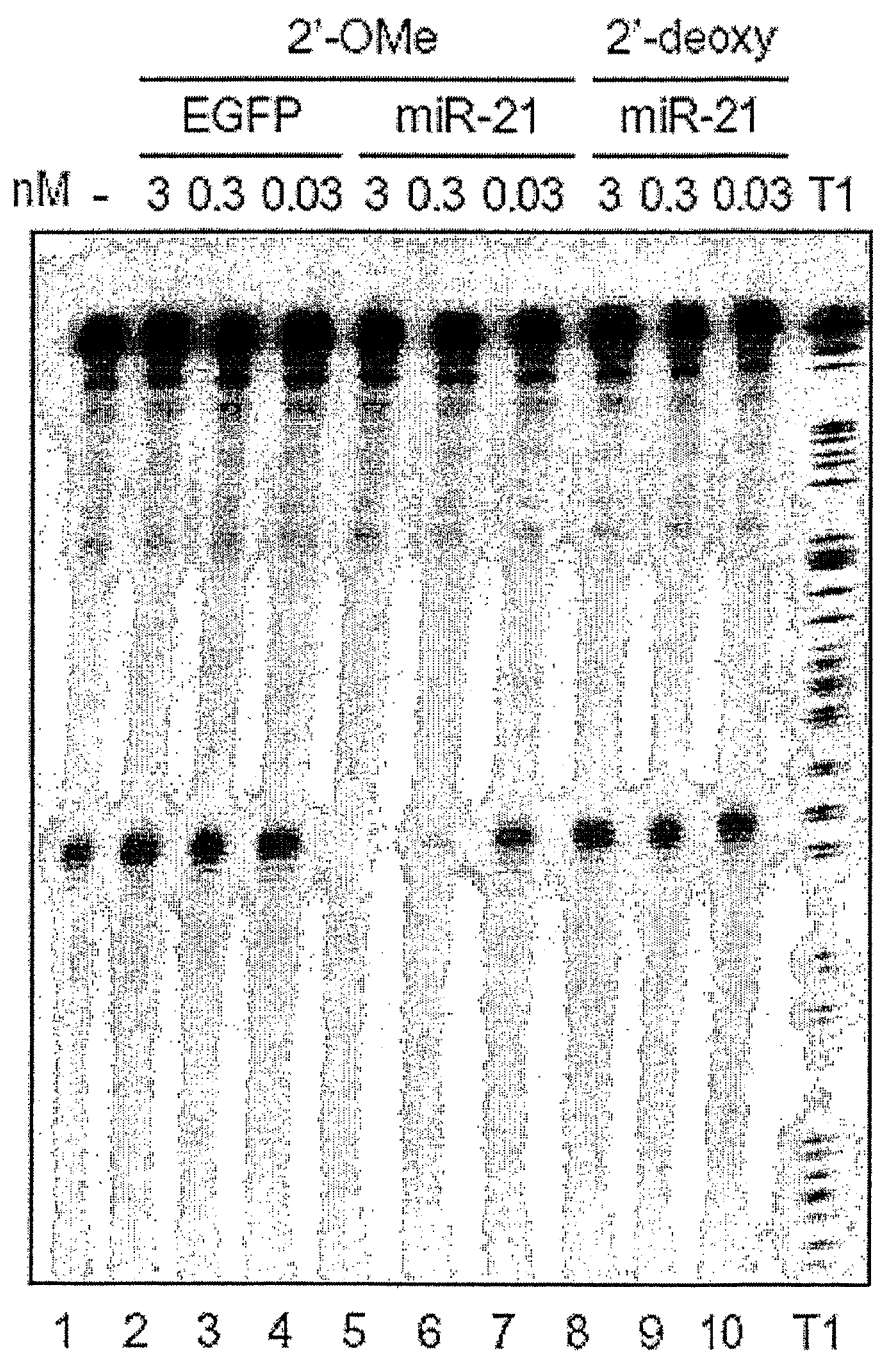
FIG. 2. Antisense 2'-O-methyl oligoribonucleotide specifically inhibit miR-21 guided cleavage activity in HeLa cell S100 cytoplasmic extracts. The black bar to the left of the RNase T1 ladder represents the region of the target RNA complementary to miR-21. Oligonucleotides complementary to miR-21 were pre-incubated in S100 extracts prior to the addition of $^{32}$P-cap-labelled cleavage substrate. Cleavage bands and T1 hydrolysis bands appear as doublets after a 1-nt slipping of the T7 RNA polymerase near the middle of the transcript indicated by the asterisk.

The invention relates to an isolated single stranded anti-microRNA molecule. The molecule comprises a minimum number of ten moieties, preferably a minimum of thirteen, more preferably a minimum of fifteen, even more preferably a minimum of 18, and most preferably a minimum of 21 moieties.

The anti-microRNA molecule comprises a maximum number of fifty moieties, preferably a maximum of forty, more preferably a maximum of thirty, even more preferably a maximum of twenty-five, and most preferably a maximum of twenty-three moieties. A suitable range of minimum and maximum number of moieties may be obtained by combining any of the above minima with any of the above maxima.

Each moiety comprises a base bonded to a backbone unit. In this specification, a base refers to any one of the nucleic acid bases present in DNA or RNA. The base can be a purine or pyrimidine. Examples of purine bases include adenine (A) and guanine (G). Examples of pyrimidine bases include thymine (T), cytosine (C) and uracil (U). Each base of the moiety forms a Watson-Crick base pair with a complementary base.

Watson-Crick base pairs as used herein refers to the hydrogen bonding interaction between, for example, the following bases: adenine and thymine (A=T); adenine and uracil (A=U); and cytosine and guanine (C≡G). The adenine can be replaced with 2,6-diaminopurine without compromising base-pairing.

The backbone unit may be any molecular unit that is able stably to bind to a base and to form an oligomeric chain. Suitable backbone units are well known to those in the art.

For example, suitable backbone units include sugar-phosphate groups, such as the sugar-phosphate groups present in ribonucleotides, deoxyribonucleotides, phosphorothioate deoxyribose groups, N'3-N'5 phosphoroamidate deoxyribose groups, 2'0-alkyl-ribose phosphate groups, 2'-O-alkyl-alkoxy ribose phosphate groups, ribose phosphate group containing a methylene bridge, 2'-Fluororibose phosphate groups, morpholino phosphoroamidate groups, cyclohexene groups, tricyclo phosphate groups, and amino acid molecules.

In one embodiment, the anti-microRNA molecule comprises at least one moiety which is a ribonucleotide moiety or a deoxyribonucleotide moiety.

In another embodiment, the anti-microRNA molecule comprises at least one moiety which confers increased nuclease resistance. The nuclease can be an exonuclease, an endonuclease, or both. The exonuclease can be a 3'→5' exonuclease or a 5'→3' exonuclease. Examples of 3'→5' human exonuclease include PNPT1, Werner syndrome helicase, RRP40, RRP41, RRP42, RRP45, and RRP46. Examples of 5'→3' exonuclease include XRN2, and FEN1. Examples of endonucleases include Dicer, Drosha, RNase4, Ribonuclease P, Ribonuclease H1, DHP1, ERCC-1 and OGG1. Examples of nucleases which function as both an exonuclease and an endonuclease include APE1 and EXO1.

An anti-microRNA molecule comprising at least one moiety which confers increased nuclease resistance means a sequence of moieties wherein at least one moiety is not recognized by a nuclease. Therefore, the nuclease resistance of the molecule is increased compared to a sequence containing only unmodified ribonucleotide, unmodified deoxyribonucleotide or both. Such modified moieties are well known in the art, and were reviewed, for example, by Kurreck, Eur. J. Biochem. 270, 1628-1644 (2003).

A modified moiety can occur at any position in the anti-microRNA molecule. For example, to protect the anti-microRNA molecule against 3'→5' exonucleases, the molecule can have at least one modified moiety at the 3' end of the molecule and preferably at least two modified moieties at the 3' end. If it is desirable to protect the molecule against 5'→3' exonuclease, the anti-microRNA molecule can have at least one modified moiety and preferably at least two modified moieties at the 5' end of the molecule. The anti-microRNA molecule can also have at least one and preferably at least two modified moieties between the 5' and 3' end of the molecule to increase resistance of the molecule to endonucleases. In one embodiment, all of the moieties are nuclease resistant.

In another embodiment, the anti-microRNA molecule comprises at least one modified deoxyribonucleotide moiety. Suitable modified deoxyribonucleotide moieties are known in the art.

A suitable example of a modified deoxyribonucleotide moiety is a phosphorothioate deoxyribonucleotide moiety. See structure 1 in FIG. 1. An anti-microRNA molecule comprising more than one phosphorothioate deoxyribonucleotide moiety is referred to as phosphorothioate (PS) DNA. See, for example, Eckstein, Antisense Nucleic Acids Drug Dev. 10, 117-121 (2000).

Another suitable example of a modified deoxyribonucleotide moiety is an N'3-N'5 phosphoroamidate deoxyribonucleotide moiety. See structure 2 in FIG. 1. An oligonucleotide molecule comprising more than one phosphoroamidate deoxyribonucleotide moiety is referred to as phosphoroamidate (NP) DNA. See, for example, Gryaznov et al., J. Am. Chem. Soc. 116, 3143-3144 (1994).

In another embodiment, the molecule comprises at least one modified ribonucleotide moiety. Suitable modified ribonucleotide moieties are known in the art.

A suitable example of a modified ribonucleotide moiety is a ribonucleotide moiety that is substituted at the 2' position. The substituents at the 2' position may, for example, be a $C_1$ to $C_4$ alkyl group. The $C_1$ to $C_4$ alkyl group may be saturated or unsaturated, and unbranched or branched. Some examples of $C_1$ to $C_4$ alkyl groups include ethyl, isopropyl, and allyl. The preferred $C_1$ to $C_4$ alkyl group is methyl. See structure 3 in FIG. 1. An oligoribonucleotide molecule comprising more than one ribonucleotide moiety that is substituted at the 2' position with a $C_1$ to $C_4$ alkyl group is referred to as a 2'-O-($C_1$-$C_4$ alkyl) RNA, e.g., 2'-O-methyl RNA (OMe RNA).

Another suitable example of a substituent at the 2' position of a modified ribonucleotide moiety is a $C_1$ to $C_4$ alkoxy-$C_1$ to $C_4$ alkyl group. The $C_1$ to $C_4$ alkoxy (alkyloxy) and $C_1$ to $C_4$ alkyl group may comprise any of the alkyl groups described above. The preferred $C_1$ to $C_4$ alkoxy-$C_1$ to $C_4$ alkyl group is methoxyethyl. See structure 4 in FIG. 1. An oligonucleotide molecule comprising more than one ribonucleotide moiety that is substituted at the 2' position. with a $C_1$ to $C_4$ alkoxy-$C_1$ to $C_4$ alkyl group is referred to as a 2'-O-($C_1$ to $C_4$ alkoxy-$C_1$ to $C_4$ alkyl) RNA, e.g., 2'-O-methoxyethyl RNA (MOE RNA).

Another suitable example of a modified ribonucleotide moiety is a ribonucleotide that has a methylene bridge between the 2'-oxygen atom and the 4'-carbon atom. See structure 5 in FIG. 1. An oligoribonucleotide molecule comprising more than one ribonucleotide moiety that has a methylene bridge between the 2'-oxygen atom and the 4'-carbon atom is referred to as locked nucleic acid (LNA). See, for example, Kurreck et al., Nucleic Acids Res. 30, 1911-1918 (2002); Elayadi et al., Curr. Opinion Invest. Drugs 2, 558-561 (2001); Ørum et al., Curr. Opinion Mol. Ther. 3, 239-243 (2001); Koshkin et al., Tetrahedron 54, 3607-3630 (1998); Obika et al., Tetrahedron Lett.39, 5401-5404 (1998). Locked nucleic acids are commercially available from Proligo (Paris, France and Boulder, Colo., USA).

Another suitable example of a modified ribonucleotide moiety is a ribonucleotide that is substituted at the 2' position with fluoro group. A modified ribonucleotide moiety having a fluoro group at the 2' position is a 2'-fluororibonucleotide moiety. Such moieties are known in the art. Molecules comprising more than one 2'-fluororibonucleotide moiety are referred to herein as 2'-fluororibo nucleic acids (FANA). See structure 7 in FIG. 1. Damha et al., J. Am. Chem. Soc. 120, 12976-12977 (1998).

In another embodiment, the anti-microRNA molecule comprises at least one base bonded to an amino acid residue. Moieties that have at least one base bonded to an amino acid residue will be referred to herein as peptide nucleic acid (PNA) moieties. Such moieties are nuclease resistance, and are known in the art. Molecules having more than one PNA moiety are referred to as peptide nucleic acids. See structure 6 in FIG. 1. Nielson, Methods Enzymol. 313, 156-164 (1999); Elayadi, et al, id.; Braasch et al., Biochemistry 41, 4503-4509 (2002), Nielsen et al., Science 254, 1497-1500 (1991).

The amino acids can be any amino acid, including natural or non-natural amino acids. Naturally occurring amino acids include, for example, the twenty most common amino acids normally found in proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivative of a naturally occurring amino acid may, for example, include the addition or one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include hydroxyl, $C_1$-$C_4$ alkoxy, amino, methylamino, dimethylamino, nitro, halo (i.e., fluoro, chloro, bromo, or iodo), or branched or unbranched $C_1$-$C_4$ alkyl, such as methyl, ethyl, n-propyl, isopropyl, butyl, isobutyl, or t-butyl.

Furthermore, other examples of non-naturally occurring amino acids which are derivatives of naturally occurring amino acids include norvaline (Nva), norleucine (Nle), and hydroxyproline (Hyp).

The amino acids can be identical or different from one another. Bases are attached to the amino acid unit by molecular linkages. Examples of linkages are methylene carbonyl, ethylene carbonyl and ethyl linkages. (Nielsen et al., *Peptide Nucleic Acids-Protocols and Applications*, Horizon Scientific Press, pages 1-19, Nielsen et al., *Science* 254: 1497-1500.)

One example of a PNA moiety is N-(2-aminoethyl)-glycine. Further examples of PNA moieties include cyclohexyl PNA, retro-inverso, phosphone, propionyl and aminoproline PNA.

PNA can be, chemically synthesized by methods known in the art, e.g. by modified Fmoc or tBoc peptide synthesis protocols. The PNA has many desirable properties, including high melting temperatures (Tm), high base-pairing specificity with nucleic acid and an uncharged molecular backbone. Additionally, the PNA does not confer RNase H sensitivity on the target RNA, and generally has good metabolic stability.

Peptide nucleic acids are also commercially available from Applied Biosystems (Foster City, Calif., USA).

In another embodiment, the anti-microRNA molecule comprises at least one morpholino phosphoroamidate nucleotide moiety. A morpholino phosphoroamidate nucleotide moiety is a modified moiety which is nuclease resistant. Such moieties are known in the art. Molecules comprising more than one morpholino phosphoroamidate nucleotide moiety are referred to as morpholino (MF) nucleic acids. See structure 8 in FIG. 1. Heasman, Dev. Biol. 243, 209-214 (2002). Morpholono oligonucleotides are commercially available from Gene Tools LLC (Corvallis, Oreg., USA).

In another embodiment, the anti-microRNA molecule comprises at least one cyclohexene nucleotide moiety. A cyclohexene nucleotide moiety is a modified moiety which is nuclease resistant. Such moieties are known in the art. Molecules comprising more than one cyclohexene nucleotide moiety are referred to as cyclohexene nucleic acids (CeNA). See structure 10 in FIG. 1. Wang et al., J. Am. Chem. Soc. 122, 8595-8602 (2000), Verbeure et al., Nucleic Acids Res. 29, 4941-4947 (2001).

In another embodiment, the anti-microRNA molecule comprises at least one tricyclo nucleotide moiety. A tricyclo nucleotide moiety is a modified moiety which is nuclease resistant. Such moieties are known in the art. Steffens et al., J. Am. Chem. Soc. 119,-11548-11549 (1-997), Renneberg et al., J. Am. Chem. Soc. 124, 5993-6002 (2002). Molecules comprising more than one tricyclo nucleotide moiety are referred to as tricyclo nucleic acids (tcDNA). See structure 9 in FIG. 1.

In another embodiment, to increase nuclease resistance of the anti-microRNA molecules of the present invention to exonucleases, inverted nucleotide caps can be attached to the 5'. end, the 3' end, or both ends of the molecule. An inverted nucleotide cap refers to a 3'→5' sequence of nucleic acids attached to the anti-microRNA molecule at the 5' and/or the 3' end. There is no limit to the maximum number of nucleotides in the inverted cap just as long as it does not interfere with binding of the anti-microRNA molecule to its target microRNA. Any nucleotide can be used in the inverted nucleotide cap. Typically, the inverted nucleotide cap is one nucleotide in length. The nucleotide for the inverted cap is generally thymine, but can be any nucleotide such as adenine, guanine, uracil, or cytosine.

Alternatively, an ethylene glycol compound and/or amino linkers can be attached to the either or both ends of the anti-microRNA molecule. Amino linkers can also be used to increase nuclease resistance of the anti-microRNA molecules to endonucleases. The table below lists some examples of amino linkers. The below listed amino linker are commercially available from TriLink Biotechnologies, San Diego, Calif.

---
2'-Deoxycytidine-5-C6 Amino Linker (3' Terminus)
2'-Deoxycytidine-5-C6 Amino Linker (5' or Internal)
3' C3 Amino Linker
3' C6 Amino Linker
3' C7 Amino Linker
5' C12 Amino Linker
5' C3 Amino Linker
5' C6 Amino Linker
C7 Internal Amino Linker
Thymidine-5-C2 Amino Linker (5' or Internal)
Thymidine-5-C6 Amino Linker (3' Terminus)
Thymidine-5-C6 Amino Linker (Internal)
---

Chimeric anti-microRNA molecules containing a mixture of any of the moieties mentioned above are also known, and may be made by methods known, in the art. See, for example, references cited above, and Wang et al, Proc. Natl. Acad. Sci. USA 96,13989-13994 (1999), Liang et al., Eur. J. Biochem. 269, 5753-5758 (2002), Lok et al., Biochemistry 41, 3457-3467 (2002), and Damha et al., J. Am. Chem. Soc. 120, 12976-12977 (2002).

The molecules of the invention comprise at least ten contiguous, preferably at least thirteen contiguous, more preferably at least fifteen contiguous, and even more preferably at least twenty contiguous bases that have the same sequence as a sequence of bases in any one of the anti-microRNA molecules shown in Tables 1-4. The anti-microRNA molecules optimally comprise the entire sequence of any one of the anti-microRNA molecule sequences shown in Tables 1-4.

For the contiguous bases mentioned above, up to thirty percent of the base pairs may be substituted by wobble base pairs. As used herein, wobble base pairs refers to either: i) substitution of a cytosine with a uracil, or 2) the substitution of a adenine with a guanine, in the sequence of the anti-microRNA molecule. These wobble base pairs are generally referred to as UG or GU wobbles. Below is a table showing the number of contiguous bases and the maximum number of wobble base pairs in the anti-microRNA molecule:

Table for Number of Wobble Bases

| | No. of Contiguous Bases | | | | | | | | | | | | |
|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Wobble Base Pairs | 3 | 3 | 3 | 3 | 4 | 4 | 4 | 5 | 5 | 5 | 6 | 6 | 6 | 6 |

Further, up to ten percent, and preferably up to five percent of the contiguous bases can be additions, deletions, mismatches or combinations thereof Additions refer to the insertion in the contiguous sequence of any moiety described above comprising any one of the bases described above. Deletions refer to the removal of any moiety present in the contiguous sequence. Mismatches refer to the substitution of one of the moieties comprising a base in the contiguous sequence with any of the above described moieties comprising a different base.

The additions, deletions or mismatches can occur anywhere in the contiguous sequence, for example, at either end of the contiguous sequence or within the contiguous sequence of the anti-microRNA molecule. If the contiguous sequence is relatively short, such as from about ten to about 15 moieties in length, preferably the additions, deletions or mismatches occur at the end of the contiguous sequence. If the contiguous sequence is relatively long, such as a minimum of sixteen contiguous sequences, then the additions, deletions, or mismatches can occur anywhere in the contiguous sequence. Below is a table showing the number of contiguous bases and the maximum number of additions, deletions, mismatches or combinations thereof:

Table for Up to 10%

| | No. of Contiguous Bases | | | | | | | | | | | | | |
|---|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Additions, Deletions and/or Mismatches | 1 | 1 | 1 | 1 | 1 | 1 | 1 | 1 | 1 | 1 | 2 | 2 | 2 | 2 |

Table for Up to 5%

| | No. of Contiguous Bases | | | | | | | | | | | | | |
|---|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Additions, Deletions and/or Mismatches | 0 | 0 | 0 | 0 | 0 | 0 | 0 | 0 | 0 | 0 | 1 | 1 | 1 | 1 |

Furthermore, no more than fifty percent, and preferably no more than thirty percent, of the contiguous moieties contain deoxyribonucleotide backbone units. Below is a table showing the number of contiguous bases and the maximum number of deoxyribonucleotide backbone units:

Table for Fifty Percent Deoxyribonucleotide Backbone Units

| | No. of Contiguous Bases | | | | | | | | | | | | | |
|---|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Deoxyribonucleotide Backbone Units | 5 | 5 | 6 | 6 | 7 | 7 | 8 | 8 | 9 | 9 | 10 | 10 | 11 | 11 |

Table for Thirty Percent Deoxyribonucleotide Backbone Units

| | No. of Contiguous Bases | | | | | | | | | | | | | |
|---|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Deoxyribonucleotide Backbone Units | 3 | 3 | 3 | 3 | 4 | 4 | 4 | 5 | 5 | 5 | 6 | 6 | 6 | 6 |

The moiety in the anti-RNA molecule at the position corresponding to position 11 of the microRNA is optionally non-complementary to a microRNA. The moiety in the anti-microRNA molecule corresponding to position 11 of the microRNA can be rendered non-complementary by an addition, deletion or mismatch as described above.

In another embodiment, if the anti-microRNA molecule comprises only unmodified moieties, then the anti-microRNA molecules comprises at least one base, in the at least ten contiguous bases, which is non-complementary to the microRNA and/or comprises an inverted nucleotide cap, ethylene glycol compound or an amino linker.

In yet another embodiment, if the at least ten contiguous bases in an anti-microRNA molecule is perfectly (i.e., 100%) complementary to ten contiguous bases in a microRNA, then the anti-microRNA molecule contains at least one modified moiety in the at least ten contiguous bases and/or comprises an inverted nucleotide cap, ethylene glycol compound or an amino linker.

As stated above, the maximum length of the anti-microRNA molecule is 50 moieties. Any number of moieties having any base sequence can be added to the contiguous base sequence. The additional moieties can be added to the 5' end, the 3' end, or to both ends of the contiguous sequence.

MicroRNA molecules are derived from genomic loci and are produced from specific microRNA genes. Mature microRNA molecules are processed from precursor transcripts that form local hairpin structures. The hairpin structures are typically cleaved by an enzyme known as Dicer, which generates one microRNA duplex. See Bartel, Cell 116, 281-297 (2004) for a review on microRNA molecules. The article by Bartel is hereby incorporated by reference.

Each strand of a microRNA is packaged in a microRNA ribonucleoprotein complex (microRNP). A microRNP in, for example, humans, also includes the proteins eIF2C2, the helicase Gemin3, and Gemin 4.

The sequence of bases in the anti-microRNA molecules of the present invention can be derived from a microRNA from any species e.g. such as a fly (e.g., *Drosophila melanogaster*), a worm (e.g., *C. elegans*). Preferably the sequence of bases is found in mammals, especially humans (*H. sapiens*), mice (e.g., *M. musculus*), and rats (*R. norvegicus*).

The anti-microRNA molecule is preferably isolated, which means that it is essentially free of other nucleic acids. Essentially free from other nucleic acids means that it is at least 90%, preferably at least 95% and, more preferably, at least 98% free of other nucleic acids.

Preferably, the molecule is essentially pure, which means that the molecules is free not only of other nucleic acids, but also of other materials used in the synthesis of the molecule, such as, for example, enzymes used in the synthesis of the molecule. The molecule is at least 90% free, preferably at least 95% free and, more preferably, at least 98% free of such materials.

The anti-microRNA molecules of the present invention are capable of inhibiting microRNP activity, preferable in a cell. Inhibiting microRNP activity refers to the inhibition of cleavage of the microRNA's target sequence or the repression of translation of the microRNA's target sequence. The method comprises introducing into the cell a single-stranded microRNA molecule.

Any anti-microRNA molecule can be used in the methods of the present invention, as long as the anti-microRNA is complementary, subject to the restrictions described above, to the microRNA present in the microRNP. Such anti-microRNAs include, for example, the anti-microRNA molecules mentioned above (see Table 1-4), and the anti-microRNAs molecules described in international PCT application number WO 03/029459 A2, the sequences of which are incorporated herein by reference.

The invention also includes any one of the microRNA molecules having the sequences as shown in Table 2. The novel microRNA molecules in Table 2 may optionally be modified as described above for anti-microRNA molecules. The other microRNA molecules in Tables 1, 3 and 4 are modified for increased nuclease resistance as described above for anti-microRNA molecules.

Utility

The anti-microRNA molecules and the microRNA molecules of the present invention have numerous in vivo, in vitro, and ex vivo applications.

For example, the anti-microRNA molecules and microRNA of the present invention may be used as a modulator of the expression of genes which are at least partially complementary to the anti-microRNA molecules and microRNA. For example, if a particular microRNA is beneficial for the survival of a cell, an appropriate isolated microRNA of the present invention may be introduced into the cell to promote survival. Alternatively, if a particular microRNA is harmful (e.g., induces apoptosis, induces cancer, etc.), an appropriate anti-microRNA molecule can be introduced into the cell in order to inhibit the activity of the microRNA and reduce the harm.

In addition, anti-microRNA molecules and/or microRNAs of-the present invention can be introduced into a cell to study the function of the microRNA. Any of the anti-microRNA molecules and/or microRNAs listed above can be introduced into a cell for studying their function. For example, a microRNA in a cell can be inhibited with a suitable anti-microRNA molecule. The function of the microRNA can be inferred by observing changes associated with inhibition of the microRNA in the cell in order to inhibit the activity of the microRNA and reduce the harm.

The cell can be any cell which expresses microRNA molecules, including the microRNA molecules listed herein. Alternatively, the cell can be any cell transfected with an expression vector containing the nucleotide sequence of a microRNA.

Examples of cells include, but are not limited to, endothelial cells, epithelial cells, leukocytes (e.g., T cells, B cells, neutrophils, macrophages, eosinophils, basophils, dendritic cells, natural killer cells and monocytes), stem cells, hemopoietic cells, embryonic cells, cancer cells.

The anti-microRNA molecules or microRNAs can be introduced into a cell by any method known to those skilled in the art. Useful delivery systems, include for example, liposomes and charged lipids. Liposomes typically encapsulate oligonucleotide molecules within their aqueous center. Charged lipids generally form lipid-oligonucleotide molecule complexes as a result of opposing charges.

These liposomes-oligonucleotide molecule complexes or lipid-oligonucleotide molecule complexes are usually internalized by endocytosis. The liposomes or charged lipids generally comprise helper lipids which disrupt the endosomal membrane and release the oligonucleotide molecules.

Other methods for introducing an anti-microRNA molecule or a microRNA into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the anti-microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., *In Antisense Technology in the Central Nervous System* (Leslie, R. A., Hunter, A. J. & Robertson, H. A., eds), pp. 147-157, Oxford University Press.

Targeting of an anti-microRNA molecule or a microRNA to a particular cell can be performed by any method known to those skilled in the art. For example, the anti-microRNA molecule or microRNA can be conjugated to an antibody or ligand specifically recognized by receptors on the cell.

The sequences of microRNA and anti-microRNA molecules are shown in Tables 1-4 below. Human sequences are indicated with the prefix "hsa." Mouse sequences are indicated with the prefix "mmu." Rat sequences are indicated with the prefix "rno." *C. elegan* sequences are indicated with the prefix "cel." Drosophila sequences are indicated with the prefix "dme."

TABLE 1

Human, Mouse and Rat microRNA and anti-microRNA sequences.

| microRNA name | microRNA sequence (5' to 3') | Anti-microRNA molecule sequence (5' to 3') |
| --- | --- | --- |
| hsa-miR-100 | SEQ ID NO. 1<br>AACCCGUAGAUCCGAACUUGUG | SEQ ID NO. 307<br>CACAAGUUCGGAUCUACGGGUU |
| hsa-miR-103 | SEQ ID NO. 2<br>AGCAGCAUUGUACAGGGCUAUG | SEQ ID NO. 308<br>CAUAGCCCUGUACAAUGCUGCU |

TABLE 1-continued

Human, Mouse and Rat microRNA and anti-microRNA sequences.

| microRNA name | microRNA sequence (5' to 3') | Anti-microRNA molecule sequence (5' to 3') |
|---|---|---|
| hsa-miR-105-5p | SEQ ID NO. 3<br>UCAAAUGCUCAGACUCCUGUGG | SEQ ID NO. 309<br>CCACAGGAGUCUGAGCAUUUGA |
| hsa-miR-106a | SEQ ID NO. 4<br>AAAAGUGCUUACAGUGCAGGUA | SEQ ID NO. 310<br>UACCUGCACUGUAAGCACUUUU |
| hsa-miR-106b | SEQ ID NO. 5<br>UAAAGUGCUGACAGUGCAGAUA | SEQ ID NO. 311<br>UAUCUGCACUGUCAGCACUUUA |
| hsa-miR-107 | SEQ ID NO. 6<br>AGCAGCAUUGUACAGGGCUAUC | SEQ ID NO. 312<br>GAUAGCCCUGUACAAUGCUGCU |
| hsa-miR-10b | SEQ ID NO. 7<br>UACCCUGUAGAACCGAAUUUGU | SEQ ID NO. 313<br>ACAAAUUCGGUUCUACAGGGUA |
| hsa-miR-128b | SEQ ID NO. 8<br>UCACAGUGAACCGGUCUCUUUC | SEQ ID NO. 314<br>GAAAGAGACCGGUUCACUGUGA |
| hsa-miR-130b | SEQ ID NO. 9<br>CAGUGCAAUGAUGAAAGGGCAU | SEQ ID NO. 315<br>AUGCCCUUUCAUCAUUGCACUG |
| hsa-miR-140-3p | SEQ ID NO. 10<br>UACCACAGGGUAGAACCACGGA | SEQ ID NO. 316<br>UCCGUGGUUCUACCCUGUGGUA |
| hsa-miR-142-5p | SEQ ID NO. 11<br>CCCAUAAAGUAGAAAGCACUAC | SEQ ID NO. 317<br>GUAGUGCUUUCUACUUUAUGGG |
| hsa-miR-151-5p | SEQ ID NO. 12<br>UCGAGGAGCUCACAGUCUAGUA | SEQ ID NO. 318<br>UACUAGACUGUGAGCUCCUCGA |
| hsa-miR-155 | SEQ ID NO. 13<br>UUAAUGCUAAUCGUGAUAGGGG | SEQ ID NO. 319<br>CCCCUAUCACGAUUAGCAUUAA |
| hsa-miR-181a | SEQ ID NO. 14<br>AACAUUCAACGCUGUCGGUGAG | SEQ ID NO. 320<br>CUCACCGACAGCGUUGAAUGUU |
| hsa-miR-181b | SEQ ID NO. 15<br>AACAUUCAUUGCUGUCGGUGGG | SEQ ID NO. 321<br>CCCACCGACAGCAAUGAAUGUU |
| hsa-miR-181c | SEQ ID NO. 16<br>AACAUUCAACCUGUCGGUGAGU | SEQ ID NO. 322<br>ACUCACCGACAGGUUGAAUGUU |
| hsa-miR-182 | SEQ ID NO. 17<br>UUUGGCAAUGGUAGAACUCACA | SEQ ID NO. 323<br>UGUGAGUUCUACCAUUGCCAAA |
| hsa-miR-183 | SEQ ID NO. 18<br>UAUGGCACUGGUAGAAUUCACU | SEQ ID NO. 324<br>AGUGAAUUCUACCAGUGCCAUA |
| hsa-miR-184 | SEQ ID NO. 19<br>UGGACGGAGAACUGAUAAGGGU | SEQ ID NO. 325<br>ACCCUUAUCAGUUCUCCGUCCA |
| hsa-miR-185 | SEQ ID NO. 20<br>UGGAGAGAAAGGCAGUUCCUGA | SEQ ID NO. 326<br>UCAGGAACUGCCUUUCUCUCCA |
| hsa-miR-186 | SEQ ID NO. 21<br>CAAAGAAUUCUCCUUUUGGGCU | SEQ ID NO. 327<br>AGCCCAAAAGGAGAAUUCUUUG |
| hsa-miR-187 | SEQ ID NO. 22<br>UCGUGUCUUGUGUUGCAGCCGG | SEQ ID NO. 328<br>CCGGCUGCAACACAAGACACGA |
| hsa-miR-188-3p | SEQ ID NO. 23<br>CUCCCACAUGCAGGGUUUGCAG | SEQ ID NO. 329<br>CUGCAAACCCUGCAUGUGGGAG |
| hsa-miR-188-5p | SEQ ID NO. 24<br>CAUCCCUUGCAUGGUGGAGGGU | SEQ ID NO. 330<br>ACCCUCCACCAUGCAAGGGAUG |
| hsa-miR-189 | SEQ ID NO. 25<br>GUGCCUACUGAGCUGAUAUCAG | SEQ ID NO. 331<br>CUGAUAUCAGCUCAGUAGGCAC |
| hsa-miR-190 | SEQ ID NO. 26<br>UGAUAUGUUUGAUAUAUUAGGU | SEQ ID NO. 332<br>ACCUAAUAUAUCAAACAUAUCA |

TABLE 1-continued

Human, Mouse and Rat microRNA and anti-microRNA sequences.

| microRNA name | microRNA sequence (5' to 3') | Anti-microRNA molecule sequence (5' to 3') |
| --- | --- | --- |
| hsa-miR-191 | SEQ ID NO. 27<br>CAACGGAAUCCCAAAAGCAGCU | SEQ ID NO. 333<br>AGCUGCUUUUGGGAUUCCGUUG |
| hsa-miR-192 | SEQ ID NO. 28<br>CUGACCUAUGAAUUGACAGCCA | SEQ ID NO. 334<br>UGGCUGUCAAUUCAUAGGUCAG |
| hsa-miR-193-3p | SEQ ID NO. 29<br>AACUGGCCUACAAAGUCCCAGU | SEQ ID NO. 335<br>ACUGGGACUUUGUAGGCCAGUU |
| hsa-miR-193-5p | SEQ ID NO. 30<br>UGGGUCUUUGCGGGCAAGAUGA | SEQ ID NO. 336<br>UCAUCUUGCCCGCAAAGACCCA |
| hsa-miR-194 | SEQ ID NO. 31<br>UGUAACAGCAACUCCAUGUGGA | SEQ ID NO. 337<br>UCCACAUGGAGUUGCUGUUACA |
| hsa-miR-195 | SEQ ID NO. 32<br>UAGCAGCACAGAAAUAUUGGCA | SEQ ID NO. 338<br>UGCCAAUAUUUCUGUGCUGCUA |
| hsa-miR-196 | SEQ ID NO. 33<br>UAGGUAGUUUCAUGUUGUUGGG | SEQ ID NO. 339<br>CCCAACAACAUGAAACUACCUA |
| hsa-miR-197 | SEQ ID NO. 34<br>UUCACCACCUUCUCCACCCAGC | SEQ ID NO. 340<br>GCUGGGUGGAGAAGGUGGUGAA |
| hsa-miR-198 | SEQ ID NO. 35<br>GGUCCAGAGGGGAGAUAGGUUC | SEQ ID NO. 341<br>GAACCUAUCUCCCCUCUGGACC |
| hsa-miR-199a-3p | SEQ ID NO. 36<br>ACAGUAGUCUGCACAUUGGUUA | SEQ ID NO. 342<br>UAACCAAUGUGCAGACUACUGU |
| hsa-miR-199a-5p | SEQ ID NO. 37<br>CCCAGUGUUCAGACUACCUGUU | SEQ ID NO. 343<br>AACAGGUAGUCUGAACACUGGG |
| hsa-miR-199b | SEQ ID NO. 38<br>CCCAGUGUUUAGACUAUCUGUU | SEQ ID NO. 344<br>AACAGAUAGUCUAAACACUGGG |
| hsa-miR-200a | SEQ ID NO. 39<br>UAACACUGUCUGGUAACGAUGU | SEQ ID NO. 345<br>ACAUCGUUACCAGACAGUGUUA |
| hsa-miR-200b | SEQ ID NO. 40<br>CUCUAAUACUGCCUGGUAAUGA | SEQ ID NO. 346<br>UCAUUACCAGGCAGUAUUAGAG |
| hsa-miR-200c | SEQ ID NO. 41<br>AAUACUGCCGGGUAAUGAUGGA | SEQ ID NO. 347<br>UCCAUCAUUACCCGGCAGUAUU |
| hsa-miR-203 | SEQ ID NO. 42<br>GUGAAAUGUUUAGGACCACUAG | SEQ ID NO. 348<br>CUAGUGGUCCUAAACAUUUCAC |
| hsa-miR-204 | SEQ ID NO. 43<br>UUCCCUUUGUCAUCCUAUGCCU | SEQ ID NO. 349<br>AGGCAUAGGAUGACAAAGGGAA |
| hsa-miR-205 | SEQ ID NO. 44<br>UCCUUCAUUCCACCGGAGUCUG | SEQ ID NO. 350<br>CAGACUCCGGUGGAAUGAAGGA |
| hsa-miR-206 | SEQ ID NO. 45<br>UGGAAUGUAAGGAAGUGUGUGG | SEQ ID NO. 351<br>CCACACACUUCCUUACAUUCCA |
| hsa-miR-208 | SEQ ID NO. 46<br>AUAAGACGAGCAAAAAGCUUGU | SEQ ID NO. 352<br>ACAAGCUUUUUGCUCGUCUUAU |
| hsa-miR-210 | SEQ ID NO. 47<br>CUGUGCGUGUGACAGCGGCUGA | SEQ ID NO. 353<br>UCAGCCGCUGUCACACGCACAG |
| hsa-miR-211 | SEQ ID NO. 48<br>UUCCCUUUGUCAUCCUUCGCCU | SEQ ID NO. 354<br>AGGCGAAGGAUGACAAAGGGAA |
| hsa-miR-212 | SEQ ID NO. 49<br>UAACAGUCUCCAGUCACGGCCA | SEQ ID NO. 355<br>UGGCCGUGACUGGAGACUGUUA |
| hsa-miR-213 | SEQ ID NO. 50<br>ACCAUCGACCGUUGAUUGUACC | SEQ ID NO. 356<br>GGUACAAUCAACGGUCGAUGGU |

TABLE 1-continued

Human, Mouse and Rat microRNA and anti-microRNA sequences.

| microRNA name | microRNA sequence (5' to 3') | Anti-microRNA molecule sequence (5' to 3') |
|---|---|---|
| hsa-miR-214 | SEQ ID NO. 51<br>ACAGCAGGCACAGACAGGCAGU | SEQ ID NO. 357<br>ACUGCCUGUCUGUGCCUGCUGU |
| hsa-miR-215 | SEQ ID NO. 52<br>AUGACCUAUGAAUUGACAGACA | SEQ ID NO. 358<br>UGUCUGUCAAUUCAUAGGUCAU |
| hsa-miR-216 | SEQ ID NO. 53<br>UAAUCUCAGCUGGCAACUGUGA | SEQ ID NO. 359<br>UCACAGUUGCCAGCUGAGAUUA |
| hsa-miR-217 | SEQ ID NO. 54<br>UACUGCAUCAGGAACUGAUUGG | SEQ ID NO. 360<br>CCAAUCAGUUCCUGAUGCAGUA |
| hsa-miR-218 | SEQ ID NO. 55<br>UUGUGCUUGAUCUAACCAUGUG | SEQ ID NO. 361<br>CACAUGGUUAGAUCAAGCACAA |
| hsa-miR-219 | SEQ ID NO. 56<br>UGAUUGUCCAAACGCAAUUCUU | SEQ ID NO. 362<br>AAGAAUUGCGUUUGGACAAUCA |
| hsa-miR-220 | SEQ ID NO. 57<br>CCACACCGUAUCUGACACUUUG | SEQ ID NO. 363<br>CAAAGUGUCAGAUACGGUGUGG |
| hsa-miR-221 | SEQ ID NO. 58<br>AGCUACAUUGUCUGCUGGGUUU | SEQ ID NO. 364<br>AAACCCAGCAGACAAUGUAGCU |
| hsa-miR-222 | SEQ ID NO. 59<br>AGCUACAUCUGGCUACUGGGUC | SEQ ID NO. 365<br>GACCCAGUAGCCAGAUGUAGCU |
| hsa-miR-223 | SEQ ID NO. 60<br>UGUCAGUUUGUCAAAUACCCCA | SEQ ID NO. 366<br>UGGGGUAUUUGACAAACUGACA |
| hsa-miR-224 | SEQ ID NO. 61<br>CAAGUCACUAGUGGUUCCGUUU | SEQ ID NO. 367<br>AAACGGAACCACUAGUGACUUG |
| hsa-miR-28-5p | SEQ ID NO. 62<br>AAGGAGCUCACAGUCUAUUGAG | SEQ ID NO. 368<br>CUCAAUAGACUGUGAGCUCCUU |
| hsa-miR-290 | SEQ ID NO. 63<br>CUCAAACUGUGGGGGCACUUUC | SEQ ID NO. 369<br>GAAAGUGCCCCCACAGUUUGAG |
| hsa-miR-296 | SEQ ID NO. 64<br>AGGGCCCCCCCUCAAUCCUGUU | SEQ ID NO. 370<br>AACAGGAUUGAGGGGGGGCCCU |
| hsa-miR-299 | SEQ ID NO. 65<br>UGGUUUACCGUCCCACAUACAU | SEQ ID NO. 371<br>AUGUAUGUGGGACGGUAAACCA |
| hsa-miR-301 | SEQ ID NO. 66<br>CAGUGCAAUAGUAUUGUCAAAG | SEQ ID NO. 372<br>CUUUGACAAUACUAUUGCACUG |
| hsa-miR-302 | SEQ ID NO. 67<br>UAAGUGCUUCCAUGUUUUGGUG | SEQ ID NO. 373<br>CACCAAAACAUGGAAGCACUUA |
| hsa-miR-30e | SEQ ID NO. 68<br>UGUAAACAUCCUUGACUGGAAG | SEQ ID NO. 374<br>CUUCCAGUCAAGGAUGUUUACA |
| hsa-miR-320 | SEQ ID NO. 69<br>AAAAGCUGGGUUGAGAGGGCGA | SEQ ID NO. 375<br>UCGCCCUCUCAACCCAGCUUUU |
| hsa-miR-321 | SEQ ID NO. 70<br>UAAGCCAGGGAUUGUGGGUUCG | SEQ ID NO. 376<br>CGAACCCACAAUCCCUGGCUUA |
| hsa-miR-322 | SEQ ID NO. 71<br>AAACAUGAAUUGCUGCUGUAUC | SEQ ID NO. 377<br>GAUACAGCAGCAAUUCAUGUUU |
| hsa-miR-323 | SEQ ID NO. 72<br>GCACAUUACACGGUCGACCUCU | SEQ ID NO. 378<br>AGAGGUCGACCGUGUAAUGUGC |
| hsa-miR-324-3p | SEQ ID NO. 73<br>CCACUGCCCCAGGUGCUGCUGG | SEQ ID NO. 379<br>CCAGCAGCACCUGGGGCAGUGG |
| hsa-miR-324-5p | SEQ ID NO. 74<br>CGCAUCCCCUAGGGCAUUGGUG | SEQ ID NO. 380<br>CACCAAUGCCCUAGGGGAUGCG |

TABLE 1-continued

Human, Mouse and Rat microRNA and anti-microRNA sequences.

| microRNA name | microRNA sequence (5' to 3') | Anti-microRNA molecule sequence (5' to 3') |
|---|---|---|
| hsa-miR-326 | SEQ ID NO. 75<br>CCUCUGGGCCCUUCCUCCAGCC | SEQ ID NO. 381<br>GGCUGGAGGAAGGGCCCAGAGG |
| hsa-miR-328 | SEQ ID NO. 76<br>CUGGCCCUCUCUGCCCUUCCGU | SEQ ID NO. 382<br>ACGGAAGGGCAGAGAGGGCCAG |
| hsa-miR-329 | SEQ ID NO. 77<br>AACACACCCAGCUAACCUUUUU | SEQ ID NO. 383<br>AAAAAGGUUAGCUGGGUGUGUU |
| hsa-miR-34a | SEQ ID NO. 78<br>UGGCAGUGUCUUAGCUGGUUGU | SEQ ID NO. 384<br>ACAACCAGCUAAGACACUGCCA |
| hsa-miR-34b | SEQ ID NO. 79<br>AGGCAGUGUCAUUAGCUGAUUG | SEQ ID NO. 385<br>CAAUCAGCUAAUGACACUGCCU |
| hsa-miR-34c | SEQ ID NO. 80<br>AGGCAGUGUAGUUAGCUGAUUG | SEQ ID NO. 386<br>CAAUCAGCUAACUACACUGCCU |
| hsa-miR-92 | SEQ ID NO. 81<br>UAUUGCACUUGUCCCGGCCUGU | SEQ ID NO. 387<br>ACAGGCCGGGACAAGUGCAAUA |
| hsa-miR-93 | SEQ ID NO. 82<br>AAAGUGCUGUUCGUGCAGGUAG | SEQ ID NO. 388<br>CUACCUGCACGAACAGCACUUU |
| hsa-miR-95 | SEQ ID NO. 83<br>UUCAACGGGUAUUUAUUGAGCA | SEQ ID NO. 389<br>UGCUCAAUAAAUACCCGUUGAA |
| hsa-miR-96 | SEQ ID NO. 84<br>UUUGGCACUAGCACAUUUUUGC | SEQ ID NO. 390<br>GCAAAAAUGUGCUAGUGCCAAA |
| hsa-miR-98 | SEQ ID NO. 85<br>UGAGGUAGUAAGUUGUAUUGUU | SEQ ID NO. 391<br>AACAAUACAACUUACUACCUCA |
| mmu-miR-106a | SEQ ID NO. 86<br>CAAAGUGCUAACAGUGCAGGUA | SEQ ID NO. 392<br>UACCUGCACUGUUAGCACUUUG |
| mmu-miR-10b | SEQ ID NO. 87<br>CCCUGUAGAACCGAAUUUGUGU | SEQ ID NO. 393<br>ACACAAAUUCGGUUCUACAGGG |
| mmu-miR-135b | SEQ ID NO. 88<br>UAUGGCUUUUCAUUCCUAUGUG | SEQ ID NO. 394<br>CACAUAGGAAUGAAAAGCCAUA |
| mmu-miR-148b | SEQ ID NO. 89<br>UCAGUGCAUCACAGAACUUUGU | SEQ ID NO. 395<br>ACAAAGUUCUGUGAUGCACUGA |
| mmu-miR-151-3p | SEQ ID NO. 90<br>CUAGACUGAGGCUCCUUGAGGA | SEQ ID NO. 396<br>UCCUCAAGGAGCCUCAGUCUAG |
| mmu-miR-155 | SEQ ID NO. 91<br>UUAAUGCUAAUUGUGAUAGGGG | SEQ ID NO. 397<br>CCCCUAUCACAAUUAGCAUUAA |
| mmu-miR-199b | SEQ ID NO. 92<br>CCCAGUGUUUAGACUACCUGUU | SEQ ID NO. 398<br>AACAGGUAGUCUAAACACUGGG |
| mmu-miR-200b | SEQ ID NO. 93<br>UAAUACUGCCUGGUAAUGAUGA | SEQ ID NO. 399<br>UCAUCAUUACCAGGCAGUAUUA |
| mmu-miR-203 | SEQ ID NO. 94<br>UGAAAUGUUUAGGACCACUAGA | SEQ ID NO. 400<br>UCUAGUGGUCCUAAACAUUUCA |
| mmu-miR-211 | SEQ ID NO. 95<br>UUCCCUUUGUCAUCCUUUGCCU | SEQ ID NO. 401<br>AGGCAAAGGAUGACAAAGGGAA |
| mmu-miR-217 | SEQ ID NO. 96<br>UACUGCAUCAGGAACUGACUGG | SEQ ID NO. 402<br>CCAGUCAGUUCCUGAUGCAGUA |
| mmu-miR-224 | SEQ ID NO. 97<br>UAAGUCACUAGUGGUUCCGUUU | SEQ ID NO. 403<br>AAACGGAACCACUAGUGACUUA |
| mmu-miR-28-3p | SEQ ID NO. 98<br>CACUAGAUUGUGAGCUGCUGGA | SEQ ID NO. 404<br>UCCAGCAGCUCACAAUCUAGUG |

TABLE 1-continued

Human, Mouse and Rat microRNA and anti-microRNA sequences.

| microRNA name | microRNA sequence (5' to 3') | Anti-microRNA molecule sequence (5' to 3') |
| --- | --- | --- |
| mmu-miR-290 | SEQ ID NO. 99<br>CUCAAACUAUGGGGGCACUUUU | SEQ ID NO. 405<br>AAAAGUGCCCCCAUAGUUUGAG |
| mmu-miR-291-3p | SEQ ID NO. 100<br>AAAGUGCUUCCACUUUGUGUGC | SEQ ID NO. 406<br>GCACACAAAGUGGAAGCACUUU |
| mmu-miR-291-5p | SEQ ID NO. 101<br>CAUCAAAGUGGAGGCCCUCUCU | SEQ ID NO. 407<br>AGAGAGGGCCUCCACUUUGAUG |
| mmu-miR-292-3p | SEQ ID NO. 102<br>AAGUGCCGCCAGGUUUUGAGUG | SEQ ID NO. 408<br>CACUCAAAACCUGGCGGCACUU |
| mmu-miR-292-5p | SEQ ID NO. 103<br>ACUCAAACUGGGGGCUCUUUUG | SEQ ID NO. 409<br>CAAAAGAGCCCCCAGUUUGAGU |
| mmu-miR-293 | SEQ ID NO. 104<br>AGUGCCGCAGAGUUUGUAGUGU | SEQ ID NO. 410<br>ACACUACAAACUCUGCGGCACU |
| mmu-miR-294 | SEQ ID NO. 105<br>AAAGUGCUUCCCUUUUGUGUGU | SEQ ID NO. 411<br>ACACACAAAAGGGAAGCACUUU |
| mmu-miR-295 | SEQ ID NO. 106<br>AAAGUGCUACUACUUUUGAGUC | SEQ ID NO. 412<br>GACUCAAAAGUAGUAGCACUUU |
| mmu-miR-297 | SEQ ID NO. 107<br>AUGUAUGUGUGCAUGUGCAUGU | SEQ ID NO. 413<br>ACAUGCACAUGCACACAUACAU |
| mmu-miR-298 | SEQ ID NO. 108<br>GGCAGAGGAGGGCUGUUCUUCC | SEQ ID NO. 414<br>GGAAGAACAGCCCUCCUCUGCC |
| mmu-miR-300 | SEQ ID NO. 109<br>UAUGCAAGGGCAAGCUCUCUUC | SEQ ID NO. 415<br>GAAGAGAGCUUGCCCUUGCAUA |
| mmu-miR-31 | SEQ ID NO. 110<br>AGGCAAGAUGCUGGCAUAGCUG | SEQ ID NO. 416<br>CAGCUAUGCCAGCAUCUUGCCU |
| mmu-miR-322 | SEQ ID NO. 111<br>AAACAUGAAGCGCUGCAACACC | SEQ ID NO. 417<br>GGUGUUGCAGCGCUUCAUGUUU |
| mmu-miR-325 | SEQ ID NO. 112<br>CCUAGUAGGUGCUCAGUAAGUG | SEQ ID NO. 418<br>CACUUACUGAGCACCUACUAGG |
| mmu-miR-326 | SEQ ID NO. 113<br>CCUCUGGGCCCUUCCUCCAGUC | SEQ ID NO. 419<br>GACUGGAGGAAGGGCCCAGAGG |
| mmu-miR-330 | SEQ ID NO. 114<br>GCAAAGCACAGGGCCUGCAGAG | SEQ ID NO. 420<br>CUCUGCAGGCCCUGUGCUUUGC |
| mmu-miR-331 | SEQ ID NO. 115<br>GCCCCUGGGCCUAUCCUAGAAC | SEQ ID NO. 421<br>GUUCUAGGAUAGGCCCAGGGGC |
| mmu-miR-337 | SEQ ID NO. 116<br>UUCAGCUCCUAUAUGAUGCCUU | SEQ ID NO. 422<br>AAGGCAUCAUAUAGGAGCUGAA |
| mmu-miR-338 | SEQ ID NO. 117<br>UCCAGCAUCAGUGAUUUUGUUG | SEQ ID NO. 423<br>CAACAAAAUCACUGAUGCUGGA |
| mmu-miR-339 | SEQ ID NO. 118<br>UCCCUGUCCUCCAGGAGCUCAC | SEQ ID NO. 424<br>GUGAGCUCCUGGAGGACAGGGA |
| mmu-miR-340 | SEQ ID NO. 119<br>UCCGUCUCAGUUACUUUAUAGC | SEQ ID NO. 425<br>GCUAUAAAGUAACUGAGACGGA |
| mmu-miR-341 | SEQ ID NO. 120<br>UCGAUCGGUCGGUCGGUCAGUC | SEQ ID NO. 426<br>GACUGACCGACCGACCGAUCGA |
| mmu-miR-342 | SEQ ID NO. 121<br>UCUCACACAGAAAUCGCACCCG | SEQ ID NO. 427<br>CGGGUGCGAUUUCUGUGUGAGA |
| mmu-miR-344 | SEQ ID NO. 122<br>UGAUCUAGCCAAAGCCUGACUG | SEQ ID NO. 428<br>CAGUCAGGCUUUGGCUAGAUCA |

TABLE 1-continued

Human, Mouse and Rat microRNA and anti-microRNA sequences.

| microRNA name | microRNA sequence (5' to 3') | Anti-microRNA molecule sequence (5' to 3') |
|---|---|---|
| mmu-miR-345 | SEQ ID NO. 123<br>UGCUGACCCCUAGUCCAGUGCU | SEQ ID NO. 429<br>AGCACUGGACUAGGGGUCAGCA |
| mmu-miR-346 | SEQ ID NO. 124<br>UGUCUGCCCGAGUGCCUGCCUC | SEQ ID NO. 430<br>GAGGCAGGCACUCGGGCAGACA |
| mmu-miR-34b | SEQ ID NO. 125<br>UAGGCAGUGUAAUUAGCUGAUU | SEQ ID NO. 431<br>AAUCAGCUAAUUACACUGCCUA |
| mmu-miR-350 | SEQ ID NO. 126<br>UUCACAAAGCCCAUACACUUUC | SEQ ID NO. 432<br>GAAAGUGUAUGGGCUUUGUGAA |
| mmu-miR-351 | SEQ ID NO. 127<br>UCCCUGAGGAGCCCUUUGAGCC | SEQ ID NO. 433<br>GGCUCAAAGGGCUCCUCAGGGA |
| mmu-miR-7b | SEQ ID NO. 128<br>UGGAAGACUUGUGAUUUUGUUG | SEQ ID NO. 434<br>CAACAAAAUCACAAGUCUUCCA |
| mmu-miR-92 | SEQ ID NO. 129<br>UAUUGCACUUGUCCCGGCCUGA | SEQ ID NO. 435<br>UCAGGCCGGGACAAGUGCAAUA |
| mmu-miR-93 | SEQ ID NO. 130<br>CAAAGUGCUGUUCGUGCAGGUA | SEQ ID NO. 436<br>UACCUGCACGAACAGCACUUUG |
| rno-miR-327 | SEQ ID NO. 131<br>CCUUGAGGGGCAUGAGGGUAGU | SEQ ID NO. 437<br>ACUACCCUCAUGCCCCUCAAGG |
| rno-miR-333 | SEQ ID NO. 132<br>GUGGUGUGCUAGUUACUUUUGG | SEQ ID NO. 438<br>CCAAAAGUAACUAGCACACCAC |
| rno-miR-335 | SEQ ID NO. 133<br>UCAAGAGCAAUAACGAAAAAUG | SEQ ID NO. 439<br>CAUUUUUCGUUAUUGCUCUUGA |
| rno-miR-336 | SEQ ID NO. 134<br>UCACCCUUCCAUAUCUAGUCUC | SEQ ID NO. 440<br>GAGACUAGAUAUGGAAGGGUGA |
| rno-miR-343 | SEQ ID NO. 135<br>UCUCCCUCCGUGUGCCCAGUAU | SEQ ID NO. 441<br>AUACUGGGCACACGGAGGGAGA |
| rno-miR-347 | SEQ ID NO. 136<br>UGUCCCUCUGGGUCGCCCAGCU | SEQ ID NO. 442<br>AGCUGGGCGACCCAGAGGGACA |
| rno-miR-349 | SEQ ID NO. 137<br>CAGCCCUGCUGUCUUAACCUCU | SEQ ID NO. 443<br>AGAGGUUAAGACAGCAGGGCUG |
| rno-miR-352 | SEQ ID NO. 138<br>AGAGUAGUAGGUUGCAUAGUAC | SEQ ID NO. 444<br>GUACUAUGCAACCUACUACUCU |

TABLE 2

Novel Human microRNA and anti-microRNA sequences.

| microRNA name | microRNA sequence (5' to 3') | Anti-microRNA molecule sequence (5' to 3') |
|---|---|---|
| hsa-miR-361 | SEQ ID NO. 139<br>UUAUCAGAAUCUCCAGGGGUAC | SEQ ID NO. 445<br>GUACCCCUGGAGAUUCUGAUAA |
| hsa-miR-362 | SEQ ID NO. 140<br>AAUCCUUGGAACCUAGGUGUGA | SEQ ID NO. 446<br>UCACACCUAGGUUCCAAGGAUU |
| hsa-miR-363 | SEQ ID NO. 141<br>AUUGCACGGUAUCCAUCUGUAA | SEQ ID NO. 447<br>UUACAGAUGGAUACCGUGCAAU |
| hsa-miR-364 | SEQ ID NO. 142<br>CGGCGGGGACGGCGAUUGGUCC | SEQ ID NO. 448<br>GGACCAAUCGCCGUCCCCGCCG |
| hsa-miR-365 | SEQ ID NO. 143<br>UAAUGCCCCUAAAAAUCCUUAU | SEQ ID NO. 449<br>AUAAGGAUUUUUAGGGGCAUUA |

TABLE 2-continued

Novel Human microRNA and anti-microRNA sequences.

| microRNA name | microRNA sequence (5' to 3') | Anti-microRNA molecule sequence (5' to 3') |
|---|---|---|
| hsa-miR-366 | SEQ ID NO. 144<br>UAACUGGUUGAACAACUGAACC | SEQ ID NO. 450<br>GGUUCAGUUGUUCAACCAGUUA |

TABLE 3

*C. elegans* microRNA and anti-microRNA sequences.

| microRNA name | microRNA sequence (5' to 3') | Anti-microRNA molecule sequence (5' to 3') |
|---|---|---|
| Cel-let-7 | SEQ ID NO. 145<br>UGAGGUAGUAGGUUGUAUAGUU | SEQ ID NO. 451<br>AACUAUACAACCUACUACCUCA |
| CeL-lin-4 | SEQ ID NO. 146<br>UCCCUGAGACCUCAAGUGUGAG | SEQ ID NO. 452<br>CUCACACUUGAGGUCUCAGGGA |
| Cel-miR-1 | SEQ ID NO. 147<br>UGGAAUGUAAAGAAGUAUGUAG | SEQ ID NO. 453<br>CUACAUACUUCUUUACAUUCCA |
| Cel-miR-2 | SEQ ID NO. 148<br>UAUCACAGCCAGCUUUGAUGUG | SEQ ID NO. 454<br>CACAUCAAAGCUGGCUGUGAUA |
| Cel-miR-34 | SEQ ID NO. 149<br>AGGCAGUGUGGUUAGCUGGUUG | SEQ ID NO. 455<br>CAACCAGCUAACCACACUGCCU |
| Cel-miR-35 | SEQ ID NO. 150<br>UCACCGGGUGGAAACUAGCAGU | SEQ ID NO. 456<br>ACUGCUAGUUUCCACCCGGUGA |
| Cel-miR-36 | SEQ ID NO. 151<br>UCACCGGGUGAAAAUUCGCAUG | SEQ ID NO. 457<br>CAUGCGAAUUUUCACCCGGUGA |
| Cel-miR-37 | SEQ ID NO. 152<br>UCACCGGGUGAACACUUGCAGU | SEQ ID NO. 458<br>ACUGCAAGUGUUCACCCGGUGA |
| Cel-miR-38 | SEQ ID NO. 153<br>UCACCGGGAGAAAAACUGGAGU | SEQ ID NO. 459<br>ACUCCAGUUUUUCUCCCGGUGA |
| Cel-miR-39 | SEQ ID NO. 154<br>UCACCGGGUGUAAAUCAGCUUG | SEQ ID NO. 460<br>CAAGCUGAUUUACACCCGGUGA |
| Cel-miR-40 | SEQ ID NO. 155<br>UCACCGGGUGUACAUCAGCUAA | SEQ ID NO. 461<br>UUAGCUGAUGUACACCCGGUGA |
| Cel-miR-41 | SEQ ID NO. 156<br>UCACCGGGUGAAAAAUCACCUA | SEQ ID NO. 462<br>UAGGUGAUUUUUCACCCGGUGA |
| Cel-miR-42 | SEQ ID NO. 157<br>CACCGGGUUAACAUCUACAGAG | SEQ ID NO. 463<br>CUCUGUAGAUGUUAACCCGGUG |
| Cel-miR-43 | SEQ ID NO. 158<br>UAUCACAGUUUACUUGCUGUCG | SEQ ID NO. 464<br>CGACAGCAAGUAAACUGUGAUA |
| Cel-miR-44 | SEQ ID NO. 159<br>UGACUAGAGACACAUUCAGCUU | SEQ ID NO. 465<br>AAGCUGAAUGUGUCUCUAGUCA |
| Cel-miR-45 | SEQ ID NO. 160<br>UGACUAGAGACACAUUCAGCUU | SEQ ID NO. 466<br>AAGCUGAAUGUGUCUCUAGUCA |
| Cel-miR-46 | SEQ ID NO. 161<br>UGUCAUGGAGUCGCUCUCUUCA | SEQ ID NO. 467<br>UGAAGAGAGCGACUCCAUGACA |
| Cel-miR-47 | SEQ ID NO. 162<br>UGUCAUGGAGGCGCUCUCUUCA | SEQ ID NO. 468<br>UGAAGAGAGCGCCUCCAUGACA |
| Cel-miR-48 | SEQ ID NO. 163<br>UGAGGUAGGCUCAGUAGAUGCG | SEQ ID NO. 469<br>CGCAUCUACUGAGCCUACCUCA |
| Cel-miR-49 | SEQ ID NO. 164<br>AAGCACCACGAGAAGCUGCAGA | SEQ ID NO. 470<br>UCUGCAGCUUCUCGUGGUGCUU |

TABLE 3-continued

*C. elegans* microRNA and anti-microRNA sequences.

| microRNA name | microRNA sequence (5' to 3') | Anti-microRNA molecule sequence (5' to 3') |
|---|---|---|
| Cel-miR-50 | SEQ ID NO. 165<br>UGAUAUGUCUGGUAUUCUUGGG | SEQ ID NO. 471<br>CCCAAGAAUACCAGACAUAUCA |
| Cel-miR-51 | SEQ ID NO. 166<br>UACCCGUAGCUCCUAUCCAUGU | SEQ ID NO. 472<br>ACAUGGAUAGGAGCUACGGGUA |
| Cel-miR-52 | SEQ ID NO. 167<br>CACCCGUACAUAUGUUUCCGUG | SEQ ID NO. 473<br>CACGGAAACAUAUGUACGGGUG |
| Cel-miR-53 | SEQ ID NO. 168<br>CACCCGUACAUUUGUUUCCGUG | SEQ ID NO. 474<br>CACGGAAACAAAUGUACGGGUG |
| Cel-miR-54 | SEQ ID NO. 169<br>UACCCGUAAUCUUCAUAAUCCG | SEQ ID NO. 475<br>CGGAUUAUGAAGAUUACGGGUA |
| Cel-miR-55 | SEQ ID NO. 170<br>UACCCGUAUAAGUUUCUGCUGA | SEQ ID NO. 476<br>UCAGCAGAAACUUAUACGGGUA |
| Cel-miR-56 | SEQ ID NO. 171<br>UACCCGUAAUGUUUCCGCUGAG | SEQ ID NO. 477<br>CUCAGCGGAAACAUUACGGGUA |
| Cel-miR-57 | SEQ ID NO. 172<br>UACCCUGUAGAUCGAGCUGUGU | SEQ ID NO. 478<br>ACACAGCUCGAUCUACAGGGUA |
| Cel-miR-58 | SEQ ID NO. 173<br>UGAGAUCGUUCAGUACGGCAAU | SEQ ID NO. 479<br>AUUGCCGUACUGAACGAUCUCA |
| Cel-miR-59 | SEQ ID NO. 174<br>UCGAAUCGUUUAUCAGGAUGAU | SEQ ID NO. 480<br>AUCAUCCUGAUAAACGAUUCGA |
| Cel-miR-60 | SEQ ID NO. 175<br>UAUUAUGCACAUUUCUAGUUC | SEQ ID NO. 481<br>GAACUAGAAAAUGUGCAUAAUA |
| Cel-miR-61 | SEQ ID NO. 176<br>UGACUAGAACCGUUACUCAUCU | SEQ ID NO. 482<br>AGAUGAGUAACGGUUCUAGUCA |
| Cel-miR-62 | SEQ ID NO. 177<br>UGAUAUGUAAUCUAGCUUACAG | SEQ ID NO. 483<br>CUGUAAGCUAGAUUACAUAUCA |
| Cel-miR-63 | SEQ ID NO. 178<br>AUGACACUGAAGCGAGUUGGAA | SEQ ID NO. 484<br>UUCCAACUCGCUUCAGUGUCAU |
| Cel-miR-64 | SEQ ID NO. 179<br>UAUGACACUGAAGCGUUACCGA | SEQ ID NO. 485<br>UCGGUAACGCUUCAGUGUCAUA |
| Cel-miR-65 | SEQ ID NO. 180<br>UAUGACACUGAAGCGUAACCGA | SEQ ID NO. 486<br>UCGGUUACGCUUCAGUGUCAUA |
| Cel-miR-66 | SEQ ID NO. 181<br>CAUGACACUGAUUAGGGAUGUG | SEQ ID NO. 487<br>CACAUCCCUAAUCAGUGUCAUG |
| Cel-miR-67 | SEQ ID NO. 182<br>UCACAACCUCCUAGAAAGAGUA | SEQ ID NO. 488<br>UACUCUUUCUAGGAGGUUGUGA |
| Cel-miR-68 | SEQ ID NO. 183<br>UCGAAGACUCAAAAGUGUAGAC | SEQ ID NO. 489<br>GUCUACACUUUUGAGUCUUCGA |
| Cel-miR-69 | SEQ ID NO. 184<br>UCGAAAAUUAAAAAGUGUAGAA | SEQ ID NO. 490<br>UUCUACACUUUUUAAUUUUCGA |
| Cel-miR-70 | SEQ ID NO. 185<br>UAAUACGUCGUUGGUGUUUCCA | SEQ ID NO. 491<br>UGGAAACACCAACGACGUAUUA |
| Cel-miR-71 | SEQ ID NO. 186<br>UGAAAGACAUGGGUAGUGAACG | SEQ ID NO. 492<br>CGUUCACUACCCAUGUCUUUCA |
| Cel-miR-72 | SEQ ID NO. 187<br>AGGCAAGAUGUUGGCAUAGCUG | SEQ ID NO. 493<br>CAGCUAUGCCAACAUCUUGCCU |
| Cel-miR-73 | SEQ ID NO. 188<br>UGGCAAGAUGUAGGCAGUUCAG | SEQ ID NO. 494<br>CUGAACUGCCUACAUCUUGCCA |

TABLE 3-continued

*C. elegans* microRNA and anti-microRNA sequences.

| microRNA name | microRNA sequence (5' to 3') | Anti-microRNA molecule sequence (5' to 3') |
|---|---|---|
| Cel-miR-74 | SEQ ID NO. 189<br>UGGCAAGAAAUGGCAGUCUACA | SEQ ID NO. 495<br>UGUAGACUGCCAUUUCUUGCCA |
| Cel-miR-75 | SEQ ID NO. 190<br>UUAAAGCUACCAACCGGCUUCA | SEQ ID NO. 496<br>UGAAGCCGGUUGGUAGCUUUAA |
| Cel-miR-76 | SEQ ID NO. 191<br>UUCGUUGUUGAUGAAGCCUUGA | SEQ ID NO. 497<br>UCAAGGCUUCAUCAACAACGAA |
| Cel-miR-77 | SEQ ID NO. 192<br>UUCAUCAGGCCAUAGCUGUCCA | SEQ ID NO. 498<br>UGGACAGCUAUGGCCUGAUGAA |
| Cel-miR-78 | SEQ ID NO. 193<br>UGGAGGCCUGGUUGUUUGUGCU | SEQ ID NO. 499<br>AGCACAAACAACCAGGCCUCCA |
| Cel-miR-79 | SEQ ID NO. 194<br>AUAAAGCUAGGUUACCAAAGCU | SEQ ID NO. 500<br>AGCUUUGGUAACCUAGCUUUAU |
| Cel-miR-227 | SEQ ID NO. 195<br>AGCUUUCGACAUGAUUCUGAAC | SEQ ID NO. 501<br>GUUCAGAAUCAUGUCGAAAGCU |
| Cel-miR-80 | SEQ ID NO. 196<br>UGAGAUCAUUAGUUGAAAGCCG | SEQ ID NO. 502<br>CGGCUUUCAACUAAUGAUCUCA |
| Cel-miR-81 | SEQ ID NO. 197<br>UGAGAUCAUCGUGAAAGCUAGU | SEQ ID NO. 503<br>ACUAGCUUUCACGAUGAUCUCA |
| Cel-miR-82 | SEQ ID NO. 198<br>UGAGAUCAUCGUGAAAGCCAGU | SEQ ID NO. 504<br>ACUGGCUUUCACGAUGAUCUCA |
| Cel-miR-83 | SEQ ID NO. 199<br>UAGCACCAUAUAAAUUCAGUAA | SEQ ID NO. 505<br>UUACUGAAUUUAUAUGGUGCUA |
| Cel-miR-84 | SEQ ID NO. 200<br>UGAGGUAGUAUGUAAUAUUGUA | SEQ ID NO. 506<br>UACAAUAUUACAUACUACCUCA |
| Cel-miR-85 | SEQ ID NO. 201<br>UACAAAGUAUUUGAAAAGUCGU | SEQ ID NO. 507<br>ACGACUUUUCAAAUACUUUGUA |
| Cel-miR-86 | SEQ ID NO. 202<br>UAAGUGAAUGCUUUGCCACAGU | SEQ ID NO. 508<br>ACUGUGGCAAAGCAUUCACUUA |
| Cel-miR-87 | SEQ ID NO. 203<br>GUGAGCAAAGUUUCAGGUGUGC | SEQ ID NO. 509<br>GCACACCUGAAACUUUGCUCAC |
| Cel-miR-90 | SEQ ID NO. 204<br>UGAUAUGUUGUUUGAAUGCCCC | SEQ ID NO. 510<br>GGGGCAUUCAAACAACAUAUCA |
| Cel-miR-124 | SEQ ID NO. 205<br>UAAGGCACGCGGUGAAUGCCAC | SEQ ID NO. 511<br>GUGGCAUUCACCGCGUGCCUUA |
| Cel-miR-228 | SEQ ID NO. 206<br>AAUGGCACUGCAUGAAUUCACG | SEQ ID NO. 512<br>CGUGAAUUCAUGCAGUGCCAUU |
| Cel-miR-229 | SEQ ID NO. 207<br>AAUGACACUGGUUAUCUUUUCC | SEQ ID NO. 513<br>GGAAAAGAUAACCAGUGUCAUU |
| Cel-miR-230 | SEQ ID NO. 208<br>GUAUUAGUUGUGCGACCAGGAG | SEQ ID NO. 514<br>CUCCUGGUCGCACAACUAAUAC |
| Cel-miR-231 | SEQ ID NO. 209<br>UAAGCUCGUGAUCAACAGGCAG | SEQ ID NO. 515<br>CUGCCUGUUGAUCACGAGCUUA |
| Cel-miR-232 | SEQ ID NO. 210<br>UAAAUGCAUCUUAACUGCGGUG | SEQ ID NO. 516<br>CACCGCAGUUAAGAUGCAUUUA |
| Cel-miR-233 | SEQ ID NO. 211<br>UUGAGCAAUGCGCAUGUGCGGG | SEQ ID NO. 517<br>CCCGCACAUGCGCAUUGCUCAA |
| Cel-miR-234 | SEQ ID NO. 212<br>UUAUUGCUCGAGAAUACCCUUU | SEQ ID NO. 518<br>AAAGGGUAUUCUCGAGCAAUAA |

TABLE 3-continued

C. elegans microRNA and anti-microRNA sequences.

| microRNA name | microRNA sequence (5' to 3') | Anti-microRNA molecule sequence (5' to 3') |
| --- | --- | --- |
| Cel-miR-235 | SEQ ID NO. 213<br>UAUUGCACUCUCCCCGGCCUGA | SEQ ID NO. 519<br>UCAGGCCGGGGAGAGUGCAAUA |
| Cel-miR-236 | SEQ ID NO. 214<br>UAAUACUGUCAGGUAAUGACGC | SEQ ID NO. 520<br>GCGUCAUUACCUGACAGUAUUA |
| Cel-miR-237 | SEQ ID NO. 215<br>UCCCUGAGAAUUCUCGAACAGC | SEQ ID NO. 521<br>GCUGUUCGAGAAUUCUCAGGGA |
| Cel-miR-238 | SEQ ID NO. 216<br>UUUGUACUCCGAUGCCAUUCAG | SEQ ID NO. 522<br>CUGAAUGGCAUCGGAGUACAAA |
| Cel-miR-239a | SEQ ID NO. 217<br>UUUGUACUACACAUAGGUACUG | SEQ ID NO. 523<br>CAGUACCUAUGUGUAGUACAAA |
| Cel-miR-239b | SEQ ID NO. 218<br>UUUGUACUACACAAAAGUACUG | SEQ ID NO. 524<br>CAGUACUUUUGUGUAGUACAAA |
| Cel-miR-240 | SEQ ID NO. 219<br>UACUGGCCCCCAAAUCUUCGCU | SEQ ID NO. 525<br>AGCGAAGAUUUGGGGGCCAGUA |
| Cel-miR-241 | SEQ ID NO. 220<br>UGAGGUAGGUGCGAGAAAUGAC | SEQ ID NO. 526<br>GUCAUUUCUCGCACCUACCUCA |
| Cel-miR-242 | SEQ ID NO. 221<br>UUGCGUAGGCCUUUGCUUCGAG | SEQ ID NO. 527<br>CUCGAAGCAAAGGCCUACGCAA |
| Cel-miR-243 | SEQ ID NO. 222<br>CGGUACGAUCGCGGCGGGAUAU | SEQ ID NO. 528<br>AUAUCCCGCCGCGAUCGUACCG |
| Cel-miR-244 | SEQ ID NO. 223<br>UCUUUGGUUGUACAAAGUGGUA | SEQ ID NO. 529<br>UACCACUUUGUACAACCAAAGA |
| Cel-miR-245 | SEQ ID NO. 224<br>AUUGGUCCCCUCCAAGUAGCUC | SEQ ID NO. 530<br>GAGCUACUUGGAGGGGACCAAU |
| Cel-miR-246 | SEQ ID NO. 225<br>UUACAUGUUUCGGGUAGGAGCU | SEQ ID NO. 531<br>AGCUCCUACCCGAAACAUGUAA |
| Cel-miR-247 | SEQ ID NO. 226<br>UGACUAGAGCCUAUUCUCUUCU | SEQ ID NO. 532<br>AGAAGAGAAUAGGCUCUAGUCA |
| Cel-miR-248 | SEQ ID NO. 227<br>UACACGUGCACGGAUAACGCUC | SEQ ID NO. 533<br>GAGCGUUAUCCGUGCACGUGUA |
| Cel-miR-249 | SEQ ID NO. 228<br>UCACAGGACUUUUGAGCGUUGC | SEQ ID NO. 534<br>GCAACGCUCAAAAGUCCUGUGA |
| Cel-miR-250 | SEQ ID NO. 229<br>UCACAGUCAACUGUUGGCAUGG | SEQ ID NO. 535<br>CCAUGCCAACAGUUGACUGUGA |
| Cel-miR-251 | SEQ ID NO. 230<br>UUAAGUAGUGGUGCCGCUCUUA | SEQ ID NO. 536<br>UAAGAGCGGCACCACUACUUAA |
| Cel-miR-252 | SEQ ID NO. 231<br>UAAGUAGUAGUGCCGCAGGUAA | SEQ ID NO. 537<br>UUACCUGCGGCACUACUACUUA |
| Cel-miR-253 | SEQ ID NO. 232<br>CACACCUCACUAACACUGACCA | SEQ ID NO. 538<br>UGGUCAGUGUUAGUGAGGUGUG |
| Cel-miR-254 | SEQ ID NO. 233<br>UGCAAAUCUUUCGCGACUGUAG | SEQ ID NO. 539<br>CUACAGUCGCGAAAGAUUUGCA |
| Cel-miR-256 | SEQ ID NO. 234<br>UGGAAUGCAUAGAAGACUGUAC | SEQ ID NO. 540<br>GUACAGUCUUCUAUGCAUUCCA |
| Cel-miR-257 | SEQ ID NO. 235<br>GAGUAUCAGGAGUACCCAGUGA | SEQ ID NO. 541<br>UCACUGGGUACUCCUGAUACUC |
| Cel-miR-258 | SEQ ID NO. 236<br>GGUUUUGAGAGGAAUCCUUUUA | SEQ ID NO. 542<br>UAAAAGGAUUCCUCUCAAAACC |

TABLE 3-continued

C. elegans microRNA and anti-microRNA sequences.

| microRNA name | microRNA sequence (5' to 3') | Anti-microRNA molecule sequence (5' to 3') |
|---|---|---|
| Cel-miR-259 | SEQ ID NO. 237<br>AGUAAAUCUCAUCCUAAUCUGG | SEQ ID NO. 543<br>CCAGAUUAGGAUGAGAUUUACU |
| Cel-miR-260 | SEQ ID NO. 238<br>GUGAUGUCGAACUCUUGUAGGA | SEQ ID NO. 544<br>UCCUACAAGAGUUCGACAUCAC |
| Cel-miR-261 | SEQ ID NO. 239<br>UAGCUUUUUAGUUUUCACGGUG | SEQ ID NO. 545<br>CACCGUGAAAACUAAAAGCUA |
| Cel-miR-262 | SEQ ID NO. 240<br>GUUUCUCGAUGUUUUCUGAUAC | SEQ ID NO. 546<br>GUAUCAGAAAACAUCGAGAAAC |
| Cel-miR-264 | SEQ ID NO. 241<br>GGCGGGUGGUUGUUGUUAUGGG | SEQ ID NO. 547<br>CCCAUAACAACAACCACCCGCC |
| Cel-miR-265 | SEQ ID NO. 242<br>UGAGGGAGGAAGGGUGGUAUUU | SEQ ID NO. 548<br>AAAUACCACCCUUCCUCCCUCA |
| Cel-miR-266 | SEQ ID NO. 243<br>AGGCAAGACUUUGGCAAAGCUU | SEQ ID NO. 549<br>AAGCUUUGCCAAAGUCUUGCCU |
| Cel-miR-267 | SEQ ID NO. 244<br>CCCGUGAAGUGUCUGCUGCAAU | SEQ ID NO. 550<br>AUUGCAGCAGACACUUCACGGG |
| Cel-miR-268 | SEQ ID NO. 245<br>GGCAAGAAUUAGAAGCAGUUUG | SEQ ID NO. 551<br>CAAACUGCUUCUAAUUCUUGCC |
| Cel-miR-269 | SEQ ID NO. 246<br>GGCAAGACUCUGGCAAAACUUG | SEQ ID NO. 552<br>CAAGUUUUGCCAGAGUCUUGCC |
| Cel-miR-270 | SEQ ID NO. 247<br>GGCAUGAUGUAGCAGUGGAGAU | SEQ ID NO. 553<br>AUCUCCACUGCUACAUCAUGCC |
| Cel-miR-271 | SEQ ID NO. 248<br>UCGCCGGGUGGGAAAGCAUUCG | SEQ ID NO. 554<br>CGAAUGCUUUCCCACCCGGCGA |
| Cel-miR-272 | SEQ ID NO. 249<br>UGUAGGCAUGGGUGUUUGGAAG | SEQ ID NO. 555<br>CUUCCAAACACCCAUGCCUACA |
| Cel-miR-273 | SEQ ID NO. 250<br>UGCCCGUACUGUGUCGGCUGCU | SEQ ID NO. 556<br>AGCAGCCGACACAGUACGGGCA |

TABLE 4

Drosophila microRNA and anti-microRNA sequences.

| microRNA name | microRNA sequence (5' to 3') | Anti-microRNA molecule sequence (5' to 3') |
|---|---|---|
| Dme-miR-263a | SEQ ID NO. 251<br>GUUAAUGGCACUGGAAGAAUUC | SEQ ID NO. 557<br>GAAUUCUUCCAGUGCCAUUAAC |
| Dme-miR-184 | SEQ ID NO. 252<br>UGGACGGAGAACUGAUAAGGGC | SEQ ID NO. 558<br>GCCCUUAUCAGUUCUCCGUCCA |
| Dme-miR-274 | SEQ ID NO. 253<br>UUUUGUGACCGACACUAACGGG | SEQ ID NO. 559<br>CCCGUUAGUGUCGGUCACAAAA |
| Dme-miR-275 | SEQ ID NO. 254<br>UCAGGUACCUGAAGUAGCGCGC | SEQ ID NO. 560<br>GCGCGCUACUUCAGGUACCUGA |
| Dme-miR-92a | SEQ ID NO. 255<br>CAUUGCACUUGUCCCGGCCUAU | SEQ ID NO. 561<br>AUAGGCCGGGACAAGUGCAAUG |
| Dme-miR-219 | SEQ ID NO. 256<br>UGAUUGUCCAAACGCAAUUCUU | SEQ ID NO. 562<br>AAGAAUUGCGUUUGGACAAUCA |
| Dme-miR-276a | SEQ ID NO. 257<br>UAGGAACUUCAUACCGUGCUCU | SEQ ID NO. 563<br>AGAGCACGGUAUGAAGUUCCUA |

TABLE 4-continued

Drosophila microRNA and anti-microRNA sequences.

| microRNA name | microRNA sequence (5' to 3') | Anti-microRNA molecule sequence (5' to 3') |
| --- | --- | --- |
| Dme-miR-277 | SEQ ID NO. 258<br>UAAAUGCACUAUCUGGUACGAC | SEQ ID NO. 564<br>GUCGUACCAGAUAGUGCAUUUA |
| Dme-miR-278 | SEQ ID NO. 259<br>UCGGUGGGACUUUCGUCCGUUU | SEQ ID NO. 565<br>AAACGGACGAAAGUCCCACCGA |
| Dme-miR-133 | SEQ ID NO. 260<br>UUGGUCCCCUUCAACCAGCUGU | SEQ ID NO. 566<br>ACAGCUGGUUGAAGGGGACCAA |
| Dme-miR-279 | SEQ ID NO. 261<br>UGACUAGAUCCACACUCAUUAA | SEQ ID NO. 567<br>UUAAUGAGUGUGGAUCUAGUCA |
| Dme-miR-33 | SEQ ID NO. 262<br>AGGUGCAUUGUAGUCGCAUUGU | SEQ ID NO. 568<br>ACAAUGCGACUACAAUGCACCU |
| Dme-miR-280 | SEQ ID NO. 263<br>UGUAUUUACGUUGCAUAUGAAA | SEQ ID NO. 569<br>UUUCAUAUGCAACGUAAAUACA |
| Dme-miR-281 | SEQ ID NO. 264<br>UGUCAUGGAAUUGCUCUCUUUG | SEQ ID NO. 570<br>CAAAGAGAGCAAUUCCAUGACA |
| Dme-miR-282 | SEQ ID NO. 265<br>AAUCUAGCCUCUACUAGGCUUU | SEQ ID NO. 571<br>AAAGCCUAGUAGAGGCUAGAUU |
| Dme-miR-283 | SEQ ID NO. 266<br>UAAAUAUCAGCUGGUAAUUCUG | SEQ ID NO. 572<br>CAGAAUUACCAGCUGAUAUUUA |
| Dme-miR-284 | SEQ ID NO. 267<br>UGAAGUCAGCAACUUGAUUCCA | SEQ ID NO. 573<br>UGGAAUCAAGUUGCUGACUUCA |
| Dme-miR-34 | SEQ ID NO. 268<br>UGGCAGUGUGGUUAGCUGGUUG | SEQ ID NO. 574<br>CAACCAGCUAACCACACUGCCA |
| Dme-miR-124 | SEQ ID NO. 269<br>UAAGGCACGCGGUGAAUGCCAA | SEQ ID NO. 575<br>UUGGCAUUCACCGCGUGCCUUA |
| Dme-miR-79 | SEQ ID NO. 270<br>UAAAGCUAGAUUACCAAAGCAU | SEQ ID NO. 576<br>AUGCUUUGGUAAUCUAGCUUUA |
| Dme-miR-276b | SEQ ID NO. 271<br>UAGGAACUUAAUACCGUGCUCU | SEQ ID NO. 577<br>AGAGCACGGUAUUAAGUUCCUA |
| Dme-miR-210 | SEQ ID NO. 272<br>UUGUGCGUGUGACAGCGGCUAU | SEQ ID NO. 578<br>AUAGCCGCUGUCACACGCACAA |
| Dme-miR-285 | SEQ ID NO. 273<br>UAGCACCAUUCGAAAUCAGUGC | SEQ ID NO. 579<br>GCACUGAUUUCGAAUGGUGCUA |
| Dme-miR-100 | SEQ ID NO. 274<br>AACCCGUAAAUCCGAACUUGUG | SEQ ID NO. 580<br>CACAAGUUCGGAUUUACGGGUU |
| Dme-miR-92b | SEQ ID NO. 275<br>AAUUGCACUAGUCCCGGCCUGC | SEQ ID NO. 581<br>GCAGGCCGGGACUAGUGCAAUU |
| Dme-miR-286 | SEQ ID NO. 276<br>UGACUAGACCGAACACUCGUGC | SEQ ID NO. 582<br>GCACGAGUGUUCGGUCUAGUCA |
| Dme-miR-287 | SEQ ID NO. 277<br>UGUGUUGAAAAUCGUUUGCACG | SEQ ID NO. 583<br>CGUGCAAACGAUUUUCAACACA |
| Dme-miR-87 | SEQ ID NO. 278<br>UUGAGCAAAAUUUCAGGUGUGU | SEQ ID NO. 584<br>ACACACCUGAAAUUUUGCUCAA |
| Dme-miR-263b | SEQ ID NO. 279<br>CUUGGCACUGGGAGAAUUCACA | SEQ ID NO. 585<br>UGUGAAUUCUCCCAGUGCCAAG |
| Dme-miR-288 | SEQ ID NO. 280<br>UUUCAUGUCGAUUUCAUUUCAU | SEQ ID NO. 586<br>AUGAAAUGAAAUCGACAUGAAA |
| Dme-miR-289 | SEQ ID NO. 281<br>UAAAUAUUUAAGUGGAGCCUGC | SEQ ID NO. 587<br>GCAGGCUCCACUUAAAUAUUUA |
| Dme-bantam | SEQ ID NO. 282<br>UGAGAUCAUUUUGAAAGCUGAU | SEQ ID NO. 588<br>AUCAGCUUUCAAAAUGAUCUCA |

TABLE 4-continued

Drosophila microRNA and anti-microRNA sequences.

| microRNA name | microRNA sequence (5' to 3') | Anti-microRNA molecule sequence (5' to 3') |
| --- | --- | --- |
| Dme-miR-303 | SEQ ID NO. 283<br>UUUAGGUUUCACAGGAAACUGG | SEQ ID NO. 589<br>CCAGUUUCCUGUGAAACCUAAA |
| Dme-miR-31b | SEQ ID NO. 284<br>UGGCAAGAUGUCGGAAUAGCUG | SEQ ID NO. 590<br>CAGCUAUUCCGACAUCUUGCCA |
| Dme-miR-304 | SEQ ID NO. 285<br>UAAUCUCAAUUUGUAAAUGUGA | SEQ ID NO. 591<br>UCACAUUUACAAAUUGAGAUUA |
| Dme-miR-305 | SEQ ID NO. 286<br>AUUGUACUUCAUCAGGUGCUCU | SEQ ID NO. 592<br>AGAGCACCUGAUGAAGUACAAU |
| Dme-miR-9c | SEQ ID NO. 287<br>UCUUUGGUAUUCUAGCUGUAGA | SEQ ID NO. 593<br>UCUACAGCUAGAAUACCAAAGA |
| Dme-miR-306 | SEQ ID NO. 288<br>UCAGGUACUUAGUGACUCUCAA | SEQ ID NO. 594<br>UUGAGAGUCACUAAGUACCUGA |
| Dme-miR-9b | SEQ ID NO. 289<br>UCUUUGGUGAUUUUAGCUGUAU | SEQ ID NO. 595<br>AUACAGCUAAAAUCACCAAAGA |
| Dme-miR-125 | SEQ ID NO. 290<br>UCCCUGAGACCCUAACUUGUGA | SEQ ID NO. 596<br>UCACAAGUUAGGGUCUCAGGGA |
| Dme-miR-307 | SEQ ID NO. 291<br>UCACAACCUCCUUGAGUGAGCG | SEQ ID NO. 597<br>CGCUCACUCAAGGAGGUUGUGA |
| Dme-miR-308 | SEQ ID NO. 292<br>AAUCACAGGAUUAUACUGUGAG | SEQ ID NO. 598<br>CUCACAGUAUAAUCCUGUGAUU |
| dme-miR-31a | SEQ ID NO. 293<br>UGGCAAGAUGUCGGCAUAGCUG | SEQ ID NO. 599<br>CAGCUAUGCCGACAUCUUGCCA |
| dme-miR-309 | SEQ ID NO. 294<br>GCACUGGGUAAAGUUUGUCCUA | SEQ ID NO. 600<br>UAGGACAAACUUUACCCAGUGC |
| dme-miR-310 | SEQ ID NO. 295<br>UAUUGCACACUUCCCGGCCUUU | SEQ ID NO. 601<br>AAAGGCCGGGAAGUGUGCAAUA |
| dme-miR-311 | SEQ ID NO. 296<br>UAUUGCACAUUCACCGGCCUGA | SEQ ID NO. 602<br>UCAGGCCGGUGAAUGUGCAAUA |
| dme-miR-312 | SEQ ID NO. 297<br>UAUUGCACuUGAGACGGCCUGA | SEQ ID NO. 603<br>UCAGGCCGUCUCAAGUGCAAUA |
| dme-miR-313 | SEQ ID NO. 298<br>UAUUGCACUUUUCACAGCCCGA | SEQ ID NO. 604<br>UCGGGCUGUGAAAAGUGCAAUA |
| dme-miR-314 | SEQ ID NO. 299<br>UAUUCGAGCCAAUAAGUUCGG | SEQ ID NO. 605<br>CCGAACUUAUUGGCUCGAAUA |
| dme-miR-315 | SEQ ID NO. 300<br>UUUUGAUUGUUGCUCAGAAAGC | SEQ ID NO. 606<br>GCUUUCUGAGCAACAAUCAAAA |
| dme-miR-316 | SEQ ID NO. 301<br>UGUCUUUUUCCGCUUACUGGCG | SEQ ID NO. 607<br>CGCCAGUAAGCGGAAAAAGACA |
| dme-miR-317 | SEQ ID NO. 302<br>UGAACACAGCUGGUGGUAUCCA | SEQ ID NO. 608<br>UGGAUACCACCAGCUGUGUUCA |
| dme-miR-318 | SEQ ID NO. 303<br>UCACUGGGCUUUGUUUAUCUCA | SEQ ID NO. 609<br>UGAGAUAAACAAAGCCCAGUGA |
| dme-miR-2c | SEQ ID NO. 304<br>UAUCACAGCCAGCUUUGAUGGG | SEQ ID NO. 610<br>CCCAUCAAAGCUGGCUGUGAUA |
| Dme-miR-iab45p | SEQ ID NO. 305<br>ACGUAUACUGAAUGUAUCCUGA | SEQ ID NO. 611<br>UCAGGAUACAUUCAGUAUACGU |
| Dme-miR-iab43p | SEQ ID NO. 306<br>CGGUAUACCUUCAGUAUACGUA | SEQ ID NO. 612<br>UACGUAUACUGAAGGUAUACCG |

EXAMPLES

Example 1

Materials and Methods

Oligonucleotide Synthesis

MiR-21 were synthesized using 5'-silyl, 2'-ACE phosphoramidites (Dharmacon, Lafayette, Colo., USA) on 0.2 µmol synthesis columns using a modified ABI 394 synthesizer (Foster City, Calif., USA) (Scaringe, Methods Enzymol. 317, 3-18 (2001) and Scaringe, Methods 23, 206-217 (2001)). The phosphate methyl group was removed by flushing the column with 2 ml of 0.2 M 2-carbamoyl-2-cyanoethylene-1, 1-dithiolate trihydrate in DMF/water (98:2 v/v) for 30 min at room temperature. The reagent was removed and the column rinsed with 10 ml water followed by 10 ml acetonitrile. The oligonucleotide was cleaved and eluted from the solid support by flushing with 1.6 ml of 40% aqueous methylamine over 2 min, collected in a screwcap vial and incubated for 10 min at 55° C. Subsequently, the base-treated oligonucleotide was dried down in an Eppendorf concentrator to remove methylamine and water. The residue was dissolved -in sterile 2'-deprotection buffer (400 µl of 100 mM acetate-TEMED, pH3.8, for a 0.2 µmol scale synthesis) and incubated for 30 minutes at 60° C. to remove the 2' ACE group. The oligoribonucleotide was precipitated from the acetate-TEMED solution by adding 24 µl 5 M NaCl and 1.2 ml of absolute ethanol.

2'-O-Methyl oligoribonucleotides were synthesized using 5'-DMT, 2'-O-methyl phosphoramidites (Proligo, Hamburg, Germany) on 1 µmol synthesis columns loaded with 3'-aminomodifier (TFA) C7 lcaa control pore glass support (Chemgenes, Mass., USA). The aminolinker was added in order to also use the oligonucleotides for conjugation to amino group reactive reagents, such as biotin succinimidyl esters. The synthesis products were deprotected for 16 h at 55° C. in 30% aqueous ammonia and then precipitated by the addition of 12 ml absolute 1-butanol. The fall-length product was then gel-purified using a denaturing 20% polyacrylamide gel. 2'-Deoxyoligonucleotides were prepared using 0.2 µmol scale synthesis and standard DNA synthesis reagents (Proligo, Hamburg, Germany).

The sequences of the 2'-O-methyl oligoribonucleotides were 5'-GUCAACAUCAGUCUGAUAAGCUAL (L, 3' aminolinker) for 2'-OMe miR-21(SEQ ID NO. 613), and 5'-AAGGCAAGCUGACCCUGAAGUL for EGFP 2'-OMe antisense (SEQ ID NO. 614), 5'-UGAAGUCCCAGUCGAACGGAAL for EGFP 2'-OMe reverse (SEQ ID NO. 615); the sequence of chimeric 2'-OMe/DNA oligonucleotides was 5'-GTCAACATCAGTCTGATAAGCTAGCL for 2'-deoxy miR-21(underlined, 2'-OMe residues)(SEQ ID NO. 616), and 5'-AAGGCAAGCTGACCCTGAAGTGCGL for EGFP 2'-deoxy antisense (SEQ ID NO. 617).

The miR-21 cleavage substrate was prepared by PCR-based extension of the partially complementary synthetic DNA oligonucleotides 5'-GAACAATTGCTTTTACAGATGCACATATCGAGGTGAACATCACG-TACGTCAACATCAGTCTGATA AGCTATCGGTTG-GCAGAAGCTAT (SEQ ID NO. 618) and 5'-GGCATAAAGAATTGAA-GAGAGTTTTCACTGCATACGACGATTCT-GTGATTTGTATTCAGCCCATAT CGTTTCATAGCTTCT-GCCAACCGA (SEQ ID NO. 619). The extended dsDNA was then used as template for a new PCR with primers 5'-TAATACGACTCACTATAGAACAATTGCTTTTACAG (SEQ ID NO. 620) and 5'-ATTTAGGTGACACTATAG-GCATAAAGAATTGAAGA (SEQ ID NO. 621) to introduce the T7 and SP6 promoter sequences for in vitro transcription. The PCR product was ligated into pCR2.1-TOPO (Invitrogen). Plasmids isolated from sequence-verified clones were used as templates for PCR to produce sufficient template for run-off in vitro transcription reactions using phage RNA polymerases (Elbashir et al., EMBO 20, 6877-6888(2001)). $^{32}$P-Cap-labelling was performed as reported (Martinez et al., Cell 110, 563-574(2002)).

Plasmids

Plasmids pEGFP-S-21 and pEGFP-A-21 were generated by T4 DNA ligation of preannealed oligodeoxynucleotides 5'-GGCCTCAACATCAGTCTGATAAGCTAGGTACCT (SEQ ID NO. 622) and 5'-GGCCAGGTACCTAGCTTAT-CAGACTGATGTTGA (SEQ ID NO. 623)into NotI digested pEGFP-N-1(Clontech). The plasmid pHcRed-C1 was from Clontech.

HeLa Extracts and miR-21 Quantification

HeLa cell extracts were prepared as described (Dignam et al., Nucleic Acid Res. 11 1475-1489 (1983)). $5 \times 10^9$ cells from HeLa suspension cultures were collected by centrifugation and washed with PBS (pH7.4). The cell pellet (approx. 15 ml) was re-suspended in two times of its volume with 10 mM KCl/1.5 mM $MgCl_2$/0.5 mM dithiothreitol/10 mM HEPES-KOH (pH 7.9) and homogenized by douncing. The nuclei were then removed by centrifugation of the cell lysate at 1000 g for 10 min. The supernatant was spun in an ultracentrifuge for 1 h at 10,5000 g to obtain the cytoplasmic S100 extract. The concentration of KCl of the S100 extract was subsequently raised to 100 mM by the addition of 1 M KCl. The extract was then supplemented with 10% glycerol and frozen in liquid nitrogen.

280 µg of total RNA was isolated from 1 ml of S100 extract using the acidic guanidinium thiocyanate-phenol-chloroform extraction method (Chomczynski et al., Anal. Biochem. 162, 156-159 (1987)). A calibration curve for miR-21 Northern signals was produced by loading increasing amounts (10 to 30000 pg) of synthetically made miR-21 (Lim et al. et al., Genes & Devel. 17, 991-1008 (2003)). Northern blot analysis was performed as described using 30 µg of total RNA per well (Lagos-Quintana et al., Science 294, 853-858 (2001)).

In vitro miRNA Cleavage and Inhibition Assay

2'-O-Methyl oligoribonucleotides or 2'-deoxyoligonucleotides were pre-incubated with HeLa S100 at 30° C. for 20 min prior to the addition of the cap-labeled miR-21 target RNA. The concentration of the reaction components were 5 nM target RNA, 1 mM ATP, 0.2 mM GTP, 10 U/ml RNasin (Promega) and 50% HeLa S100 extract in a final reaction volume of 25 µl. The reaction time was 1.5 h at 30° C. The reaction was stopped by addition of 200 µl of 300 mM NaCl/ 25 mM EDTA/20% w/v SDS/200 mM Tris HCl (pH7.5). Subsequently, proteinase K was added to a final concentration of 0.6 mg/ml and the sample was incubated for 15 min at 65° C. After phenol/chloroform extraction, the-RNA was ethanol-precipitated and separated on a 6% denaturing polyacrylamide gel. Radioactivity was detected by phosphorimaging.

Cell Culture and Transfection

HeLa S3 and HeLa S3/GFP were grown in 5% CO2 at 37° C. in Dulbecco's modified Eagle's medium (DMEM) supplemented with 10% fetal bovine serum (FBS), 100 unit/ml penicillin, and 100 µg/ml streptomycin. One day before transfection, 105 cells were plated in 500 µl DMEM containing 10% FBS per well of a 24-well plate. Plasmid and plasmid/oligonucleotide transfection was carried out with Lipofectamine2000 (Invitrogen). 0.2 μg pEGFP or its derivatives were cotransfected with 0.3 μg pHcRed with or without 10 pmol of 2'-O-methyl oligoribonucleotide or 10 pmol of 2'-deoxyoligonucleotide per well. Fluorescent cell images were recorded on a Zeiss Axiovert 200 inverted fluorescence microscope (Plan-Apochromat 10×0.45) equipped with Chroma Technology Corp. filter sets 41001 (EGFP) and 41002c (HcRed) and AxioVision 3.1 software.

Example 2

MicroRNA-21 Cleavage of Target RNA

In order to assess the ability of modified oligonucleotides to specifically interfere with miRNA function, we used our previously described mammalian biochemical system developed for assaying RISC activity (Martinez et al., Cell 100, 563-574 (2002)). Zamore and colleagues (Hutvágner et al., Science 297, 2056-2050 (2002)) showed that crude cytoplasmic cell lysates and eIF2C2 immunoprecipitates prepared from these lysates contain let-7 RNPs that specifically cleave let-7-complementary target RNAs. We previously reported that in HeLa cells, numerous miRNAs are expressed including several let-7 miRNA variants (Lagos-Quintana et al., Science 294, 853-858 (2001)).

To assess if other HeLa cell miRNAs are also engaged in RISC like miRNPs we examined the cleavage of a 32P-cap-labelled substrate RNA with a complementary site to the highly expressed miR-21 (Lagos-Quintana et al., Science 294, 853-858 (2001); Mourelatos et al., Genes & Dev. 16, 720-728 (2002)). Sequence-specific target RNA degradation was readily observed and appeared to be approximately 2- to 5-fold more effective than cleavage of a similar let-7 target RNA (FIG. 2A, lane 1, and data not shown). We therefore decided to interfere with miR-21 guided target RNA cleavage.

Example 3

Anti MicroRNA-21 2'-O-methyl Oligoribonucleotide Inhibited MicroRNA-21-Induced Cleavage of Target RNA A 24-nucleotide 2'-O-methyl oligoribonucleotide that contained a 3' C7 aminolinker and was complementary to the longest form of the miR-21 was synthesized. The aminolinker was introduced in order to enable post-synthetic conjugation of non-nucleotidic residues such as biotin.

Increasing concentrations of anti miR-21 2'-O-methyl oligoribonucleotide and a control 2'-O-methyl oligoribonucleotide cognate to an EGFP sequence were added to the S100 extract 20 min prior to the addition of 32P-cap-labelled substrate. We determined the concentration of miR-21 in the S100 extract by quantitative Northern blotting to be 50 pM (Lim et al., Genes & Devel. 17,-991-1008 (2003)).

The control EGFP oligonucleotide did not interfere with miR-21 cleavage even at the highest applied concentration (FIG. 2A, lanes 2-3). In contrast, the activity of miR-21 was completely blocked at a concentration of only 3 nM (FIG. 2A, lane 5), and a concentration of 0.3 nM showed a substantial 60%-70% reduction of cleavage activity (FIG. 2, lane 6) At a concentration of 0.03 nM, the cleavage activity of miR-21 was not affected when compared to the lysate alone (FIG. 2, lane 1,7).

Antisense 2'-deoxyoligonucleotides (approximately 90% DNA molecules) at concentrations identical to those of 2'-O-methyl oligoribonucleotides, we could not detect blockage of miR-21 induced cleavage (FIG. 2A, lanes 8-10). The 2'-deoxynucleotides used in this study were protected-against 3'-exonucleases by the addition of three 2'-O-methyl ribonucleotide residues.

Example 4

Anti MicroRNA-21 2'-O-methyl Oligoribonucleotide Inhibited MicroRNA-21-Induced Cleavage of Target RNA In Vitro In order to monitor the activity of miR-21 in HeLa cells, we constructed reporter plasmids that express EGFP mRNA that contains in its 3' UTR a 22-nt sequence complementary to miR-21 (pEGFP-S-21) or in sense orientation to miR-21 (p-EGFP-A-21). Endogenous miRNAs have previously been shown to act like siRNAs by cleaving reporter mRNAs carrying sequences perfectly complementary to miRNA. To monitor transfection efficiency and specific interference with the EGFP indicator plasmids, the far-red fluorescent protein encoding plasmid pHcRed-C1 was cotransfected.

Figure 3:
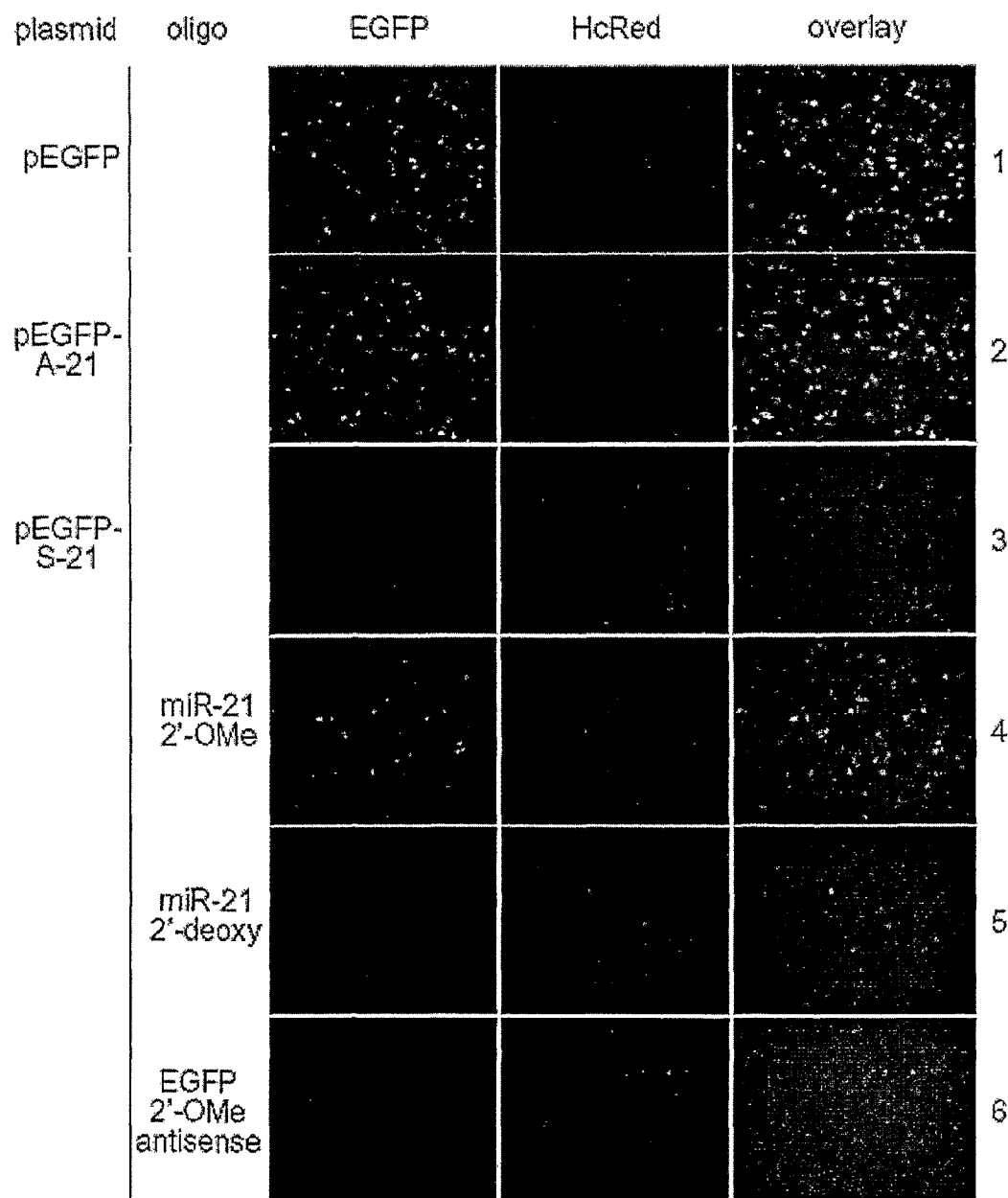
FIG. 3. Antisense 2'-O-methyl oligoribonucleotides interfere with endogenous miR-21 RNP cleavage in HeLa cells. HeLa cells were transfected with pHcRed and pEGFP or its derivatives, with or without inhibitory or control oligonucleotides. EGFP and HcRed protein fluorescence were excited and recorded individually by fluorescence microscopy 24 h after transfection. Co-expression of co-transfected reporter plasmids was documented by superimposing of the fluorescence images in the right panel.

Expression of EGFP was observed in HeLa cells transfected with pEGFP and pEGFP-A-21 (FIG. 3, rows 1 and 2), but not from those transfected with pEGFP-S-21 (FIG. 3, row 3). However, expression of EGFP from pEGFP-S-21 was restored upon cotransfection with anti miR-21 2'-O-methyl oligoribonucleotide (FIG. 3, row 4). Consistent with our above observation, the 2'-deoxy anti miR-21 oligonucleotide showed no effect (FIG. 3, row 5). Similarly, cotransfection of the EGFP 2'-O-methyl oligoribonucleotide in sense orientation with respect to the EGFP mRNA (or antisense to EGFP guide siRNA) had no effect (FIG. 3,row 6).

We have demonstrated that miRNP complexes can be effectively and sequence-specifically inhibited with 2'-O-methyl oligoribonucleotides antisense to the guide strand positioned in the RNA silencing complex.

What we claim is:

1. An isolated molecule comprising a maximum of fifty moieties, wherein each moiety comprises a base bonded to a backbone unit said molecule comprising the microRNA molecule identified in SEQ ID NO: 139 or its corresponding anti-micro RNA molecule identified in SEQ ID NO: 445.

2. A molecule according to claim 1, wherein the molecule is modified for increased nuclease resistance.

3. The molecule according to claim 1, wherein at least one of the moieties is a modified ribonucleotide moiety.

4. The molecule according to claim 3, wherein the modified ribonucleotide is substituted at the 2' position.

5. The molecule according to claim 4, wherein the substituent at the 2' position is a $C_1$ to $C_4$ alkyl group.

6. The molecule according to claim 5, wherein the alkyl group is methyl.

7. The molecule according to claim 5, wherein the alkyl group is allyl.

8. The molecule according to claim 4, wherein the substituent at the 2' position is a $C_1$ to $C_4$ alkoxy-$C_1$ to $C_4$ alkyl group.

9. The molecule according to claim 8, wherein the $C_1$ to $C_4$ alkoxy-$C_1$ to $C_4$ alkyl group is methoxyethyl.

10. The molecule according to claim 1, wherein at least one of the moieties is a 2'-fluororibonucleotide moiety.

11. The molecule according to claim 3, wherein the modified ribonucleotide has a methylene bridge between the 2'-oxygen atom and the 4'-carbon atom.

12. The molecule according to claim 1, wherein the molecule comprises at least one modified moiety on the 5' end.

13. The molecule according to claim 1, wherein the molecule comprises at least two modified moieties at the 5' end.

14. The molecule according to claim 1, wherein the molecule comprises at least one modified moiety on the 3' end.

15. The molecule according to claim 1, wherein the molecule comprises at least two modified moieties at the 3' end.

16. The molecule according to claim 1, wherein the molecule comprises at least two modified moieties at the 5' end and at least two modified moieties at the 3' end.

17. The molecule according to claim 1, wherein the molecule comprises a nucleotide cap at the 5' end, the 3' end or both.

18. The molecule according to claim 1, wherein the molecule consists of the microRNA molecule identified in SEQ ID NO: 139.

19. The molecule according to claim 1, wherein the molecule consists of the anti-micro RNA molecule identified in SEQ ID NO: 445.

* * * * *